US012717227B2

(12) United States Patent
Shimizu et al.

(10) Patent No.: US 12,717,227 B2
(45) Date of Patent: Aug. 25, 2026

(54) COMPOUND, POLYMERIZABLE COMPOSITION, POLYMER, HOLOGRAPHIC RECORDING MEDIUM, OPTICAL MATERIAL, AND OPTICAL COMPONENT

(71) Applicant: MITSUBISHI CHEMICAL CORPORATION, Tokyo (JP)

(72) Inventors: Takanori Shimizu, Tokyo (JP); Akiko Yabe, Tokyo (JP); Shuji Yamashita, Tokyo (JP); Takashi Ohtani, Tokyo (JP); Tatsuya Ishikawa, Tokyo (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 784 days.

(21) Appl. No.: 17/744,795

(22) Filed: May 16, 2022

(65) Prior Publication Data

US 2022/0283497 A1 Sep. 8, 2022

Related U.S. Application Data

(63) Continuation of application No. PCT/JP2020/042609, filed on Nov. 16, 2020.

(30) Foreign Application Priority Data

Nov. 19, 2019 (JP) ................................ 2019-208980

(51) Int. Cl.
*G03H 1/02* (2006.01)
*C07D 277/66* (2006.01)
(Continued)

(52) U.S. Cl.
CPC ........... *G03F 7/001* (2013.01); *C07D 277/66* (2013.01); *C07D 333/76* (2013.01);
(Continued)

(58) Field of Classification Search
None
See application file for complete search history.

(56) References Cited

U.S. PATENT DOCUMENTS 7,045,558 B2 5/2006 Chisholm et al.
7,101,618 B2 9/2006 Coggio et al.
(Continued)

FOREIGN PATENT DOCUMENTS

JP H06-220131 A 8/1994
JP 2000007741 A 1/2000
(Continued)

OTHER PUBLICATIONS

Office Action issued Jul. 2, 2024 in corresponding Chinese Patent Application No. 202080075618.8 (with machine English translation), 13 pages.

(Continued)

*Primary Examiner* — Martin J Angebranndt
(74) *Attorney, Agent, or Firm* — Element IP, PLC

(57) ABSTRACT

A compound represented by the following formula (1):

(1)

(Continued)

[wherein $R^1$ represents a hydrogen atom or a methyl group; $R^2$ represents an aromatic ring group optionally having a substituent or an alkyl group substituted with an aromatic ring group optionally having a substituent; $X^1$ represents a (thio)ester bond, a (thio)carbonate bond, a (thio)amide bond, a (thio)urethane bond, a (thio)urea bond, a (thio)ether bond, oxygen, sulfur, or a nitrogen atom optionally having a substituent; $X^2$ represents oxygen, sulfur, or a nitrogen atom optionally having a substituent; A represents a divalent group optionally having a substituent; L represents an (m+1)-valent linking group optionally having a substituent; m represents an integer of 1 to 3; and n represents 0 or 1].

15 Claims, 1 Drawing Sheet

(51) Int. Cl.

| | |
|---|---|
| ***C07D 333/76*** | (2006.01) |
| ***C07D 339/08*** | (2006.01) |
| ***C08F 20/38*** | (2006.01) |
| ***G03F 1/04*** | (2006.01) |
| ***G03F 7/00*** | (2006.01) |
| *G03H 1/04* | (2006.01) |

(52) U.S. Cl.

CPC ............ *C07D 339/08* (2013.01); *C08F 20/38* (2013.01); *G03H 1/02* (2013.01); *G03H 1/0402* (2013.01); *G03H 2001/0439* (2013.01); *G03H 2260/12* (2013.01)

(56) References Cited

U.S. PATENT DOCUMENTS

| | | | | |
|---|---|---|---|---|
| 7,173,778 | B2 | 2/2007 | Jing et al. | |
| 7,267,850 | B2 | 9/2007 | Coggio et al. | |
| 7,271,283 | B2 | 9/2007 | Chisholm et al. | |
| 7,332,217 | B2 | 2/2008 | Coggio et al. | |
| 7,491,441 | B2 | 2/2009 | Pokorny et al. | |
| 2005/0049325 | A1 | 3/2005 | Chisholm et al. | |
| 2005/0049376 | A1 | 3/2005 | Chisholm et al. | |
| 2005/0249940 | A1 | 11/2005 | Klun et al. | |
| 2005/0249942 | A1 | 11/2005 | Coggio et al. | |
| 2005/0249956 | A1 | 11/2005 | Jing et al. | |
| 2005/0249957 | A1 | 11/2005 | Jing et al. | |
| 2006/0147702 | A1 | 7/2006 | Pokorny et al. | |
| 2006/0251885 | A1 | 11/2006 | Coggio et al. | |
| 2007/0014018 | A1 | 1/2007 | Wheatley et al. | |
| 2007/0237948 | A1 | 10/2007 | Coggio et al. | |
| 2007/0285778 | A1 | 12/2007 | Walker et al. | |
| 2007/0285779 | A1 | 12/2007 | Walker et al. | |
| 2010/0087564 | A1* | 4/2010 | Weiser | G03F 7/027 522/90 |
| 2011/0092612 | A1* | 4/2011 | Miki | G03C 1/73 549/17 |
| 2012/0219884 | A1* | 8/2012 | Weiser | G03F 7/027 430/2 |
| 2013/0252140 | A1* | 9/2013 | Facke | G03F 7/027 430/2 |
| 2019/0171160 | A1* | 6/2019 | Hagen | B32B 27/00 |
| 2020/0355997 | A1* | 11/2020 | Lane | G03F 7/038 |
| 2021/0080826 | A1* | 3/2021 | Tanaka | C08G 18/4825 |
| 2021/0116805 | A1* | 4/2021 | Shimizu | C08G 18/285 |
| 2024/0018137 | A1* | 1/2024 | Yamashita | C07D 417/14 |
| 2024/0233765 | A1* | 7/2024 | Otsu | G11B 7/24044 |
| 2025/0206731 | A1* | 6/2025 | Yamashita | G02B 27/02 |

FOREIGN PATENT DOCUMENTS

| | | | | |
|---|---|---|---|---|
| JP | 2005133071 | A | | 5/2005 |
| JP | 2008094987 | A | | 4/2008 |
| JP | 2008527413 | A | | 7/2008 |
| JP | 2012082387 | A | | 4/2012 |
| JP | 2013095833 | A | | 5/2013 |
| JP | 2016222566 | A | | 12/2016 |
| JP | 2017014213 | A | | 1/2017 |
| JP | 2017509722 | A | | 4/2017 |
| JP | 2021024842 | A | * | 2/2021 |

OTHER PUBLICATIONS

"The Novel Photocurable Network: Urea-tetraacrylate/thiol System" Journal of Photopolymer Science and Technology, vol. 23, No. 1 (2010), pp. 121-124 (4 pages).

Extended European search report in corresponding application EP 20890168.6 issued May 8, 2023 (6 pages).

International Search Report issued Dec. 12, 2020 in PCT/JP2020/042609 (with English translation), 7 pages.

Combined Chinese Office Action and Search Report issued Sep. 23, 2023 in Chinese Patent Application No. 202080075618.8 (with machine English translation), 20 pages.

Office Action issued Mar. 23, 2024 in corresponding Chinese Patent Application No. 202080075618.8 (with machine English translation), 14 pages.

Office Action issued Feb. 21, 2023 in Japanese Patent Application No. 2021-558366 (with English translation), 11 pages.

Office Action issued May 27, 2026, in corresponding European Patent Application No. 20890168.6, 5 pages.

* cited by examiner

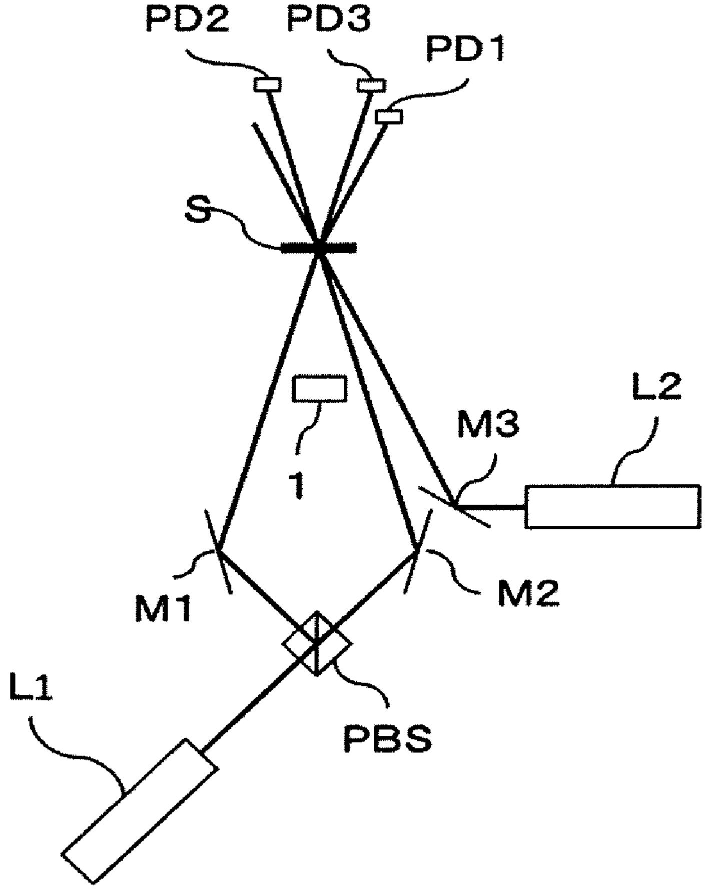
PD2
PD3
PD1
S
1
M3
L2
M1
M2
L1
PBS

COMPOUND, POLYMERIZABLE COMPOSITION, POLYMER, HOLOGRAPHIC RECORDING MEDIUM, OPTICAL MATERIAL, AND OPTICAL COMPONENT

TECHNICAL FIELD

The present invention relates to a compound having a high refractive index and good polymerizability and a polymerizable composition containing the compound. The present invention also relates to a holographic recording medium, an optical material, and an optical component that use the polymerizable composition or a polymer thereof.

BACKGROUND ART

Glass has often been used for optical components. For example, as for optical lenses with the same focal length, a lens produced using a high-refractive index material can have a smaller thickness, and this is advantageous in that the weight of the lens can be reduced and that the design flexibility of an optical path increases. High-refractive index optical lenses are also effective in reducing size of optical imaging devices and increasing their resolution and angle of view.

In recent years, highly transparent plastics are receiving attention as optical materials alternative to glass. Plastic materials have advantages over glass in that they can be easily reduced in weight, that their mechanical strength can be easily improved, and that they can be easily shaped. With the development of peripheral technologies, there is an increasing demand for plastic optical materials with improved performance. For example, materials for optical lens applications are required to be easily polymerized (have easy polymerizability), have good curability, and form polymerized products with a high refractive index (high-refractive index polymerized products).

Various resins have been developed for the purpose of improving their refractive index. Examples of such a resin include o-phenylphenol EO-modified acrylate (PTL 1) and 9,9-bis[4-(2-acryloyloxyethoxy)phenyl]fluorene (PTL 2). Various compounds having molecular structures obtained by modifying these compounds have been developed as homopolymers and copolymers and studied in order to improve their refractive index (PTL 3 and PTL 4).

9,9-Bis[4-(2-acryloyloxyethoxy)phenyl]fluorene is often used as high-refractive index acrylate. However, its viscosity is relatively high, and the refractive index of the monomer is about 1.62, which is not sufficiently high (PTL 5).

One way to increase the refractive index is to introduce an aromatic ring, and introducing a sulfur atom into a molecule is also effective. For example, PTL 6 describes a diacrylate monomer having a pentaerythritol skeleton and including 1 to 2 naphthylthio groups per molecule, and the refractive index of the monomer is 1.62 to 1.65.

PTL 7 describes an acrylate compound having a glycerin skeleton and including two benzothiazole rings per molecule, and the refractive index of the acrylate compound is 1.63.

The above compounds are not sufficient for applications that require an ultrahigh refractive index higher than 1.65.

To further increase the capacity and density of optical recording mediums, holographic optical recording mediums have been developed in which information is recorded as a hologram by changing the refractive index of a recording layer according to the distribution of light intensity caused by light interference. Moreover, it has recently been contemplated that holographic recording mediums developed for memory applications are applied to optical element applications such as light guide plates for AR (augmented reality) glasses.

PTL 8 relates to an optical material used for holographic recording mediums and describes, as an ultrahigh refractive index compound, a pentaerythritol-type (meth)acrylate compound having three aromatic rings. It is stated that a structure in which a (meth)acrylic group is bonded directly to the pentaerythritol skeleton is used in order to obtain a high refractive index. However, with this structure, sufficient polymerizability is not obtained due to steric hindrance around the (meth)acrylic group, and holographic recording characteristics may be low.

PTL 1: JP2013-95833A
PTL 2: JP2000-7741A
PTL 3: JP2008-94987A
PTL 4: JP2012-82387A
PTL 5: JP6-220131A
PTL 6: JP2008-527413A
PTL 7: JP2005-133071A
PTL 8: JP2017-14213A

SUMMARY OF INVENTION

It is an object of the present invention to provide an easily polymerizable high-refractive index compound useful as an optical material or an optical component.

Solution to Problem

The present inventors have found that a pentaerythritol-type compound having a structure including three aromatic rings and bonded to a polymerizable group through a specific linking group is an easily polymerizable high-refractive index compound and that a polymerizable composition and a polymer using this compound have a high refractive index, and thus the inventors have arrived at the invention.

The present invention is summarized as follows.

[1] A compound represented by the following formula (1):

[Chem. 1]

(1)

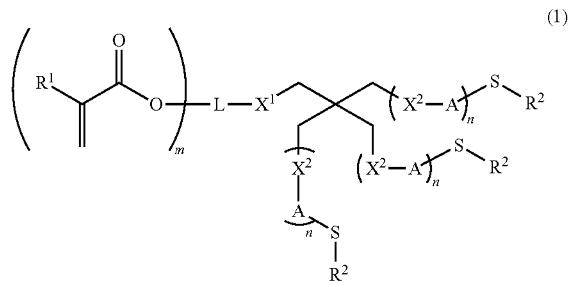

In the formula, $R^1$ represents a hydrogen atom or a methyl group; $R^2$ represents an aromatic ring group optionally having a substituent or an alkyl group substituted with an aromatic ring group optionally having a substituent; $X^1$ represents a (thio)ester bond, a (thio)carbonate bond, a (thio)amide bond, a (thio)urethane bond, a (thio)urea bond, a (thio)ether bond, oxygen, sulfur, or a nitrogen atom optionally having a substituent; $X^2$ represents oxygen, sulfur, or a nitrogen atom optionally having a substituent; A represents a divalent group optionally having a substituent;

L represents an (m+1)-valent linking group optionally having a substituent; m represents an integer of 1 to 3; and n represents 0 or 1.

[2] The compound according to [1], wherein n is 0.

[3] The compound according to [1] or [2], wherein L is a hydrocarbon group having 1 to 8 carbon atoms and optionally having a substituent.

[4] The compound according to [3], wherein L is an aliphatic hydrocarbon group having 1 to 8 carbon atoms and optionally having a substituent.

[5] The compound according to [4], wherein L is a chain aliphatic hydrocarbon group having 1 to 8 carbon atoms and optionally having a substituent.

[6] The compound according to any one of [1] to [5], wherein $R^2$ is a fused aromatic heterocyclic group optionally having a substituent or an aromatic hydrocarbon group having a fused heterocyclic group as a substituent.

[7] The compound according to [6], wherein $R^2$ is a sulfur-containing fused aromatic heterocyclic group or an aromatic hydrocarbon group having a sulfur-containing fused heterocyclic group as a substituent.

[8] The compound according to [7], wherein $R^2$ is a dibenzothiophenyl group, a benzothiazolyl group, a thianthrenyl group, or an aromatic hydrocarbon group having a dibenzothiophenyl group, a benzothiazolyl group, or a thianthrenyl group as a substituent.

[9] A polymerizable composition comprising: the compound according to any one of [1] to [8]; and a polymerization initiator.

[10] A holographic recording medium comprising the polymerizable composition according to [9].

[11] A polymer obtained by polymerizing the polymerizable composition according to [9],

[12] An optical material comprising the polymer according to [11].

[13] An optical component comprising the polymer according to [11].

[14] A large-capacity memory comprising the holographic recording medium according to [10].

[15] An optical element obtained by recording a hologram in the holographic recording medium according to [10].

[16] An AR glass comprising the optical element according to [15].

Advantageous Effects of Invention

The present invention provides an easily polymerizable high-refractive index compound useful as an optical material. This compound is particularly useful as a reactive compound used for hard coat layers of optical lenses and optical members and for holographic recording mediums.

The use of the compound of the invention allows an optical material and an optical component having high diffraction efficiency, high light transmittance, and a small shrinkage factor to be achieved.

BRIEF DESCRIPTION OF DRAWING

FIG. 1 is a schematic illustration showing the outline of the structure of a device used for holographic recording.

DESCRIPTION OF EMBODIMENTS

Embodiments of the present invention will next be described specifically. The present invention is not limited to the following embodiments and can be modified variously within the scope of the invention.

In the present invention, a "(thio)ester bond" is a generic term for an ester bond and a thioester bond. A "(thio) carbonate bond" is a generic term for a carbonate bond and a thiocarbonate bond. A "(thio)amide bond" is a generic term for an amide bond and a thioamide bond. A "(thio)urethane bond" is a generic term for a urethane bond and a thiourethane bond. A "(thio)urea bond" is a generic term for a urea bond and a thiourea bond. A "(thio)ether bond" is a generic term for an ether bond and a thioether bond.

In the present invention, "(meth)acrylate" is a generic term for acrylate and methacrylate. A "(meth)acrylic group" is a generic term for an acrylic group and a methacrylic group. "(Meth)acrylic acid" is a generic term for acrylic acid and methacrylic acid.

In the present invention, the phrase "a group optionally having a substituent" means that the group may have one or more substituents.

1. Compound of Invention

The compound of the present invention is a compound represented by the following formula (1) and having a (meth)acrylic group that is a polymerizable functional group.

[Chem. 2]

(1)

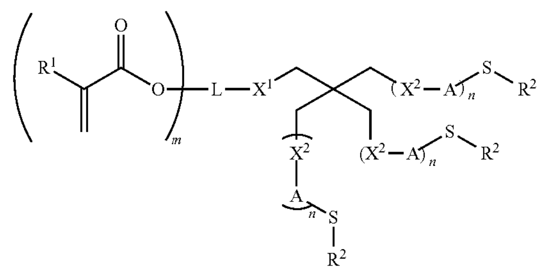

[wherein $R^1$ represents a hydrogen atom or a methyl group. $R^2$ represents an aromatic ring group optionally having a substituent or an alkyl group substituted with an aromatic ring group optionally having a substituent. $X^1$ represents a (thio)ester bond, a (thio)carbonate bond, a (thio)amide bond, (thio)urethane bond, a (thio)urea bond, a (thio)ether bond, oxygen, sulfur, or a nitrogen atom optionally having a substituent. $X^2$ represents oxygen, sulfur, or a nitrogen atom optionally having a substituent. A represents a divalent group optionally having a substituent. L represents an (m+1)-valent linking group optionally having a substituent. m represents an integer of 1 to 3. n represents 0 or 1.]

1-1. $R^1$ in Formula (1)

$R^1$ represents a hydrogen atom or a methyl group. To obtain a compound with higher polymerizability, $R^2$ is preferably a hydrogen atom.

When m in formula (1) is 2 or 3 and a plurality of $R^1$s are present, the plurality of $R^1$s may be the same or different.

1-2. $R^2$ in Formula (1)

$R^2$ represents an aromatic ring group optionally having a substituent or an alkyl group substituted with an aromatic ring group optionally having a substituent. The aromatic ring contained in $R^2$ may be a fused ring.

The aromatic rings that can be contained in $R^2$ are broadly classified into an aromatic hydrocarbon ring and an aromatic heterocycle. The alkyl group substituted with an aromatic ring group optionally having a substituent is an aralkyl or heteroaralkyl group optionally having a substituent in the aromatic ring.

Examples of the aromatic hydrocarbon ring include groups such as a benzene ring, a naphthalene ring, an anthracene ring, a phenanthrene ring, a perylene ring, a tetracene ring, a pyrene ring, a benzpyrene ring, a chrysene ring, a biphenylene ring, a triphenylene ring, an acenaphthene ring, a fluoranthene ring, and a fluorene ring. Examples of the aromatic heterocycle include: aromatic heterocycles including one heteroatom such as a furan ring, a benzofuran ring, a dibenzofuran ring, a naphthofuran ring, a benzonaphthofuran ring, a dinaphthofuran ring, a thiophene ring, a benzothiophene ring, a dibenzothiophene ring, a naphthothiophene ring, a benzonaphthothiophene ring, a dinaphthothiophene ring, a pyrrole ring, an indole ring, a carbazole ring, a pyridine ring, a quinoline ring, and an isoquinoline ring; aromatic heterocycles including two or more heteroatoms such as an imidazole ring, a triazole ring, a tetrazole ring, an oxazole ring, a triazole ring, a pyridazine ring, a pyrimidine ring, a pyrazine ring, a triazine ring, and a thiadiazole ring; and rings each including two or three fused rings including an aromatic heterocycle having two or more heteroatoms such as a benzoxazole ring, a thienooxazole ring, a thiazolooxazole ring, an oxazolooxazole ring, an oxazoloimidazole ring, an oxazolopyridine ring, an oxazolopyridazine ring, an oxazolopyrimidine ring, an oxazolopyrazine ring, a naphthooxazole ring, a quinolinooxazole ring, a dioxazolopyrazine ring, a phenoxazine ring, a benzothiazole ring, a furothiazole ring, a thienothiazole ring, a thiazolothiazole ring, a thiazoloimidazole ring, a thienothiadiazole ring, a thiazolothiadiazole ring, a thiazolopyridine ring, a thiazolopyridazine ring, a thiazolopyrimidine ring, a thiazolopyrazine ring, a naphthothiazole ring, a quinolinothiazole ring, a thianthrene ring, and a phenothiazine ring. Each of these ring structures may be bonded to a heteroatom at any position and may have any substituent.

Examples of the aralkyl group include a benzyl group, a 2-phenylethyl group, and a naphthylmethyl group. Examples of the heteroaralkyl group include a furylmethyl group, a thienylmethyl group, and a benzothienylmethyl group. Each of these groups may have any substituent.

From the viewpoint of imparting a low water absorption rate, $R^2$ is preferably an aromatic hydrocarbon group and more preferably a naphthyl group, an anthracenyl group, or a fluorenyl group.

From the viewpoint of obtaining a high-refractive index compound, $R^2$ is preferably a fused aromatic ring group optionally having a substituent or an aromatic heterocyclic group optionally having a substituent and more preferably a fused aromatic group including two or three fused rings including an aromatic heterocycle having a heteroatom.

The aromatic heterocyclic group is preferably a sulfur-containing aromatic heterocyclic group because a high refractive index can be obtained. The sulfur-containing aromatic heterocyclic group has at least a sulfur atom as a heteroatom included in the aromatic heterocycle. The sulfur-containing aromatic heterocyclic group may have, in addition to the sulfur atom, an oxygen atom or a nitrogen atom as a heteroatom and may have an oxygen atom and a nitrogen atom as heteroatoms.

From the viewpoint of avoiding coloration and obtaining sufficient solubility, the number of heteroatoms included in the sulfur-containing aromatic heterocyclic group is preferably 1 to 3 and more preferably 1 to 2.

Examples of the sulfur-containing aromatic heterocycle in the sulfur-containing aromatic heterocyclic group include: aromatic heterocycles including one sulfur atom such as a thiophene ring, a benzothiophene ring, a dibenzothiophene ring, a benzonaphthothiophene ring, a dinaphthothiophene ring, a thiopyran ring, a naphthothiophene ring, a dinaphthothiophene ring, and a dibenzothiopyran ring; aromatic heterocycles including two or more sulfur atoms such as a thianthrene ring; and aromatic heterocycles including two or more types of heteroatoms such as a thiazole ring, an isothiazole ring, a benzothiazole ring, a naphthothiazole ring, a phenothiazine ring, a thiazoloimidazole ring, a thiazolopyridine ring, a thiazolopyridazine ring, a thiazolopyrimidine ring, a dioxazolopyrazine ring, a thiazolopyrazine ring, a thiazolooxazole ring, a dibenzobenzothiophene ring, a thienooxazole ring, a thienothiadiazole ring, and a thiazolothiadiazole ring. The sulfur-containing aromatic heterocycle may be a monocycle or may be a fused ring. From the viewpoint of increasing the refractive index, the sulfur-containing aromatic heterocycle is preferably a fused ring. The number of rings forming the fused ring is preferably 2 to 8, more preferably 2 to 6, and still more preferably 2 to 5 in terms of availability of raw materials and ease of synthesis.

Among the above rings, a benzothiazole ring, a dibenzothiophene ring, a benzothiophene ring, a benzonaphthothiophene ring, a dinaphthothiophene ring, and a thianthrene ring are preferred in terms of low colorability and obtaining a high refractive index, and a benzothiazole ring, a dibenzothiophene ring, and a thianthrene ring are more preferred.

$R^2$ may have a substituent. Examples of the substituent that $R^2$ may have include halogen atoms such as chlorine, bromine, and iodine, an alkyl group having 1 to 8 carbon atoms, an alkenyl group having 2 to 8 carbon atoms, an alkoxyl group having 1 to 8 carbon atoms, a phenyl group, a mesityl group, a tolyl group, a naphthyl group, a cyano group, an acetyloxy group, an alkylcarbonyloxy group having 2 to 9 carbon atoms, an alkoxycarbonyl group having 2 to 9 carbon atoms, a sulfamoyl group, an alkylsulfamoyl group having 2 to 9 carbon atoms, an alkylcarbonyl group having 2 to 9 carbon atoms, a phenethyl group, a hydroxyethyl group, an acetylamido group, a dialkylaminoethyl group to which an alkyl group having 1 to 4 carbon atoms is bonded, a trifluoromethyl group, an alkylthio group having 1 to 8 carbon atoms, an arylthio group having 6 to 10 carbon atoms, and a nitro group.

Of these, an alkyl group having 1 to 8 carbon atoms, an alkoxyl group having 1 to 8 carbon atoms, a cyano group, an acetyloxy group, an alkylcarbonyloxy group having 2 to 8 carbon atoms, a sulfamoyl group, an alkylsulfamoyl group having 2 to 9 carbon atoms, a nitro group are preferred.

$R^2$ may have an aromatic heterocyclic group as a substituent.

The definition of the aromatic heterocyclic group that $R^2$ may have as a substituent is the same as that for $R^2$ described above. From the viewpoint of improving the refractive index, the aromatic heterocyclic group is preferably a sulfur-containing aromatic heterocyclic group. Specifically, the sulfur-containing aromatic heterocycle is preferably a benzothiazole ring, a dibenzothiophene ring, a benzothiophene ring, a benzonaphthothiophene ring, a dinaphthothiophene ring, or a thianthrene ring and more preferably a benzothiazole ring, a dibenzothiophene ring, or a thianthrene ring.

Specific examples of the aromatic ring group having a substituent include: aromatic hydrocarbon groups having a substituent such as a biphenyl group, a benzylphenyl group, a phenoxyphenyl group, a binaphthyl group, a methylthionaphthyl group, a benzothiazolylphenyl group, a benzoxazolylphenyl group, and a dibenzothiophenylphenyl group; aromatic heterocycles having a substituent such as a methoxycarbonylfuryl group, a methylthiothiophene group, a nitrocarbazole group, a methylbenzoxazole group, a methylbenzothiazole group, a methoxybenzothiazole group, and a chlorobenzothiazole group; and aralkyl groups having a substituent such as a biphenylmethyl group, a naphthylthioethyl group, and a fluorenylmethyl group.

1-3. $X^1$ in Formula (1)

$X^1$ represents a (thio)ester bond, a (thio)carbonate bond, a (thio)amide bond, a (thio)urethane bond, a (thio)urea bond, a (thio)ether bond, oxygen, sulfur, or a nitrogen atom optionally having a substituent. No particular limitation is imposed on the group with which the nitrogen atom may be substituted. Preferred examples of such a group include: alkyl groups having 1 to 8 carbon atoms such as a methyl group and an ethyl group; and aromatic hydrocarbon groups such as a phenyl group and a naphthyl group.

From the viewpoint of facilitating the synthesis of the compound of formula (1) and reducing the viscosity, $X^1$ is selected from oxygen, sulfur, and a nitrogen atom optionally having a substituent and is selected preferably from oxygen and a sulfur atom. In particular, an oxygen atom may be used because the compound of formula (1) can be produced from relatively low-cost pentaerythritoltribromide.

From the viewpoint of improving the polymerizability of the compound of the present invention, $X^1$ is preferably an ester bond, a carbonate bond, an amide bond, a urethane bond, a urea bond, or an ether bond and more preferably an amide bond, a urethane bond, or a urea bond.

For the purpose of increasing the refractive index of the compound of the present invention, $X^1$ may be selected from a thioester bond, a thiocarbonate bond, a thioamide bond, a thiourethane bond, a thiourea bond, and a thioether bond.

1-4. $X^2$ in Formula (1)

$X^2$ represents oxygen, sulfur, or a nitrogen atom optionally having a substituent. No particular limitation is imposed on the group with which the nitrogen atom may be substituted. Preferred examples of such a group include: alkyl groups having 1 to 8 carbon atoms such as a methyl group and an ethyl group; and aromatic hydrocarbon groups such as a phenyl group and a naphthyl group.

$X^2$ is preferably an oxygen or sulfur atom from the viewpoint of reducing the water absorption rate of the compound of the invention to a low level and more preferably a sulfur atom that imparts a high refractive index to the compound of the invention.

1-5. A in Formula (1)

A represents a divalent group optionally having a substituent.

The divalent group is a an optionally branched divalent organic group and is preferably an optionally branched divalent organic group having 1 to 8 carbon atoms and more preferably an ethylidene group, a propylidene group, a methylene group, an ethylene group, a propylene group, a 2-hydroxypropylene group, an oxopropylene group, an oxobutylene group, a 3-oxapentylene group, a cyclohexylene group, a phenylene group, or a xylylene group and particularly preferably a methylene group, an ethylene group, a propylene group, or a 2-hydroxypropylene group. When the number of carbon atoms in A is 8 or less, the refractive index of the compound of the invention is high, and its viscosity is low. Moreover, the processability of the compound tends to be improved.

Exampled of the optional substituent on A include halogen atoms such as chlorine, bromine, and iodine, a hydroxy group, a mercapto group, an alkyl group having 1 to 8 carbon atoms, an alkenyl group having 2 to 8 carbon atoms, an alkoxyl group having 1 to 8 carbon atoms, a phenyl group, a mesityl group, a tolyl group, a naphthyl group, a cyano group, an acetyloxy group, an alkylcarbonyloxy group having 2 to 9 carbon atoms, an alkoxycarbonyl group having 2 to 9 carbon atoms, a sulfamoyl group, an alkylsulfamoyl group having 2 to 9 carbon atoms, an alkylcarbonyl group having 2 to 9 carbon atoms, a phenethyl group, a hydroxyethyl group, an acetylamido group, a dialkylaminoethyl group to which alkyl groups having 1 to 4 carbon atoms are bonded, a trifluoromethyl group, an alkylthio group having 1 to 8 carbon atoms, an arylthio group having 6 to 10 carbon atoms, and a nitro group.

Of these, an alkyl group having 1 to 8 carbon atoms, an alkoxyl group having 1 to 8 carbon atoms, a cyano group, an acetyloxy group, an alkylcarbonyloxy group having 2 to 8 carbon atoms, a sulfamoyl group, an alkylsulfamoyl group having 2 to 9 carbon atoms, a phenyl group, and a naphthyl group are preferred.

1-6. m and n in Formula (1)

m represents an integer of 1 to 3. m is preferably 1 or 2 and more preferably 1 because the refractive index of the compound of the invention tends to be high.

n represents 0 or 1. As n increases, the molecular weight of the compound increases. In this case, the viscosity of the polymerizable composition of the invention increases, and its processability may decrease. Therefore, n is preferably 0. When n is 0, the refractive index of the compound of the invention tends to further increase.

1-7. L in Formula (1)

L is an (m+1)-valent linking group optionally having a substituent and can be selected appropriately according to the intended purpose of the compound of the invention.

L used can be selected appropriately from linear, branched, and cyclic linking groups. From the viewpoint of reducing steric hindrance around the (meth)acrylic group(s) in the compound of the invention, L is preferably linear.

Examples of the chain linking group included in L when m=1 include a methylene group, an ethylene group, a 1,3-propylene group, a 1,2-propylene group, a butylene group, a 2-hydroxypropylene group, an oxoethylene group, an oxopropylene group, an oxobutylene group, an oxohexylene group, an oxoheptylene group, a 3-oxapentylene group, $—CH_2CH_2NHC(O)—$, $—CH_2CH_2OCH_2CH_2NHC(O)—$, $—CH_2CH_2NHC(O)—$, $—CH_2CH_2SCH_2CH_2—$, $—CH_2CH_2NHC(S)—$, $—CH_2CH_2OCH_2CH_2NHC(S)—$, $—CH_2CH_2SCH_2CH_2NHC(S)—$, and $—CH_2CH_2NHC(S)—$, and any combination thereof may be used. When m=2 or 3, any hydrogen atom in the chain compound may be replaced with a (meth)acryloyl group, or the chain compound may be bonded to a (meth)acryloyl group through a branch structure.

Examples of the optional substituent on L include halogen atoms (a chlorine atom, a bromine atom, and an iodine atom), a hydroxy group, a mercapto group, an alkyl group having 1 to 8 carbon atoms, an alkenyl group having 2 to 8 carbon atoms, an alkoxy group having 1 to 8 carbon atoms, a phenyl group, a mesityl group, a tolyl group, a naphthyl group, a cyano group, an acetyloxy group, an alkylcarbonyloxy group having 2 to 9 carbon atoms, an alkoxycarbonyl group having 2 to 9 carbon atoms, a sulfamoyl group, an alkylsulfamoyl group having 2 to 9 carbon atoms, an alkylcarbonyl group having 2 to 9 carbon atoms, a phenethyl group, a hydroxyethyl group, an acetylamido group, a dialkylaminoethyl group to which alkyl groups having 1 to 4 carbon atoms are bonded, a trifluoromethyl group, an alkylthio group having 1 to 8 carbon atoms, an arylthio group having 6 to 10 carbon atoms, and a nitro group.

In terms of allowing the compound of the invention to have sufficient solubility in various mediums and avoiding coloration, L is preferably an aliphatic hydrocarbon group.

In this case, the number of carbon atoms in the aliphatic hydrocarbon group represented by L is preferably 1 to 8 (excluding the number of carbon atoms in a substituent) because a reduction in the refractive index of the compound of the invention and an increase in the viscosity of the polymerizable composition of the invention can be prevented. In terms of reducing the steric hindrance described above, the aliphatic hydrocarbon group is preferably linear.

A cyclic linking group may be selected as L for the purpose of increasing the refractive index of the compound of the invention. In this case, L may have a monocyclic structure or a fused ring structure, and the number of rings forming L is preferably 1 to 4, more preferably 1 to 3, and still more preferably 1 to 2. Each ring included in L is not necessary to have aromaticity. However, to keep the size of L in the molecule small and maintain the high refractive index, L is preferably an aromatic hydrocarbon ring. Examples of the aromatic hydrocarbon ring included in L include a benzene ring, an indene ring, a naphthalene ring, an azulene ring, a fluorene ring, an acenaphthylene ring, an anthracene ring, a phenanthrene ring, and a pyrene ring.

For the purpose of improving the polymerizability of the compound of the invention, at least one of an ester bond, a carbonate bond, an amide bond, a urethane bond, a urea bond, and an ether bond may be used for L. In this case, any of an amide bond, a urethane bond, and a urea bond is more preferred.

For the purpose of improving the refractive index of the compound of the invention, any of a thioester bond, a thiocarbonate bond, a thioamide bond, a thiourethane bond, a thiourea bond, and a thioether bond may be used for L.

1-8. Molecular Weight

From the viewpoint of reducing the viscosity of the compound of the invention to a low level and keeping the processability good, the molecular weight of the compound is preferably 2000 or lower and more preferably 1500 or lower. In terms of reducing the shrinkage factor during polymerization, the molecular weight of the compound of the invention is preferably 400 or more, more preferably 500 or more, and still more preferably 550 or more.

1-9. Water Solubility

Preferably, the compound of the invention is insoluble in water in order to improve its storage stability and prevent deformation due to moisture absorption after curing. The term "insoluble in water" means that the water solubility under the conditions of 25° C. and 1 atm is generally 0.1% by mass or less, preferably 0.02% by mass or less, and more preferably 0.01% by mass or less. When the compound has a certain degree of water solubility, the effect of improving dispersibility in water or a polar solvent during polymerization and the effect of improving the adhesion to a substrate are obtained. Therefore, in this case, the solubility in water is preferably 0.1% by mass or more and more preferably 1% mass or more.

In the present invention, water solubility suitable for the intended purpose and application can be set by appropriately selecting the structure of the compound represented by formula (1).

1-10. Relation Between Molecular Structure and Physical Properties

In the high-refractive index compound of the invention, $R^2$s each having an aromatic ring are introduced into three of the four molecular chains of the quaternary carbon in the pentaerythritol skeleton. The three aromatic rings in $R^2$s are disposed at appropriate intermolecular distances with sulfur atoms interposed therebetween. Therefore, the compound (monomer) before the polymerization reaction has high solubility in various mediums including organic solvents. However, in the polymer of the compound obtained by the polymerization reaction, the aromatic rings of different molecules are disposed close to each other, so that the aromatic ring density increases locally. Therefore, the polymer can have a high refractive index.

As described above, to allow the polymer to have a high refractive index, it is necessary that the polymerization reaction proceed sufficiently.

In the compound of the invention, the highly refractive moieties introduced into the pentaerythritol skeleton and the (meth)acrylic groups that are polymerizable groups are linked through an appropriate linking group L. This allows the steric hindrance around the polymerizable groups to be reduced, and high polymerizability and a high refractive index can be achieved simultaneously.

In the compound of the invention represented by formula (1), a linking structure such as L, A, $X^1$, or $X^2$ may be interposed between the pentaerythritol skeleton and the (meth)acryl moiety or each $SR^2$ moiety, and the presence of the linking structure allows the physical properties of the compound of the invention to be adjusted according to its intended application.

The compound of the invention has the pentaerythritol skeleton including chemically stable quaternary carbon and is therefore thermally and chemically stable in all stages such as synthesis, processing, and storage.

1-11. Exemplary Compounds

Specific examples of the compound of the invention represented by formula (1) are exemplified below. The present invention is not limited to these compounds so long as they do not depart from the scope of the invention.

Specific examples of the compound represented by formula (1) when m=1 and n=0 are as follow.

[Chem. 3]

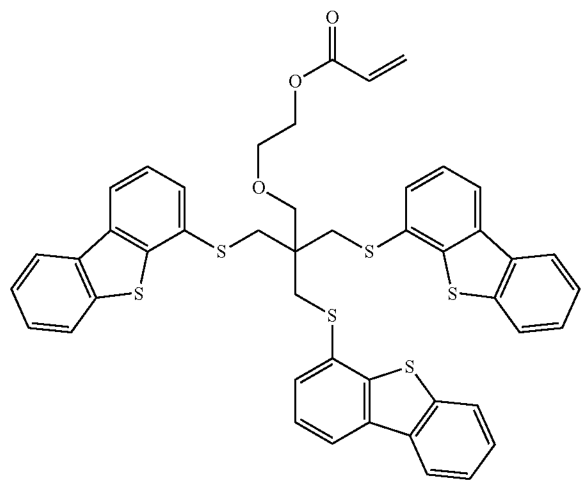

-continued
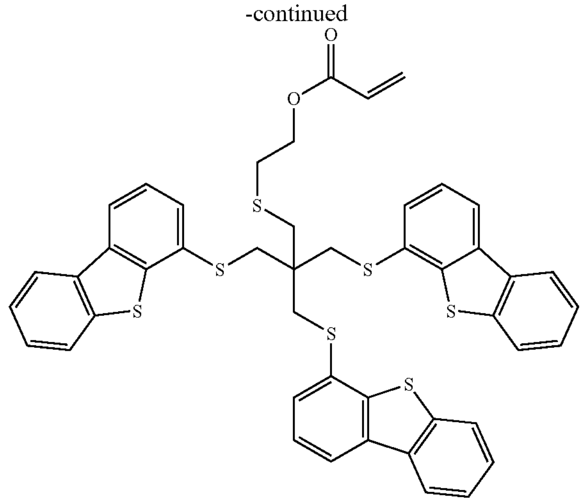
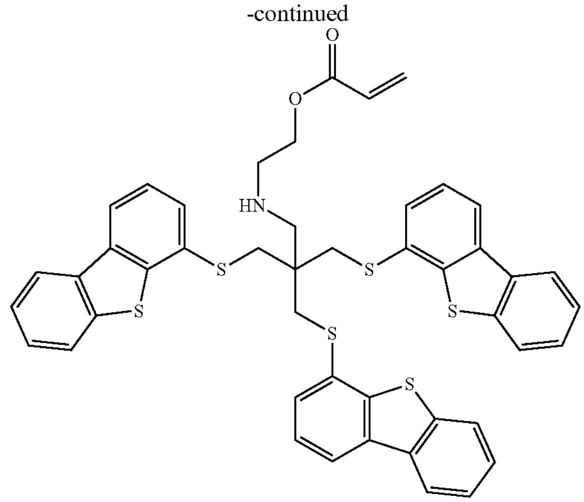
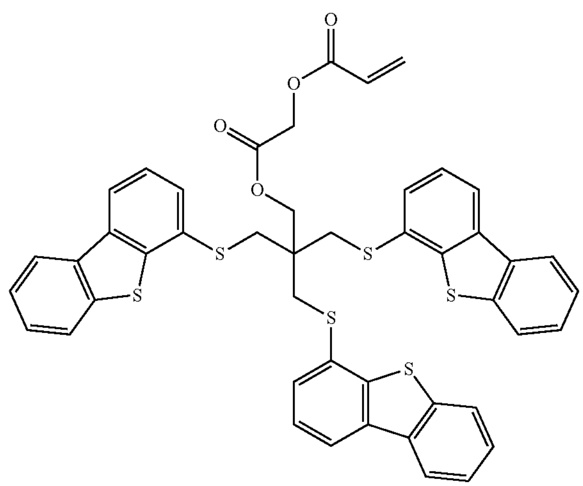
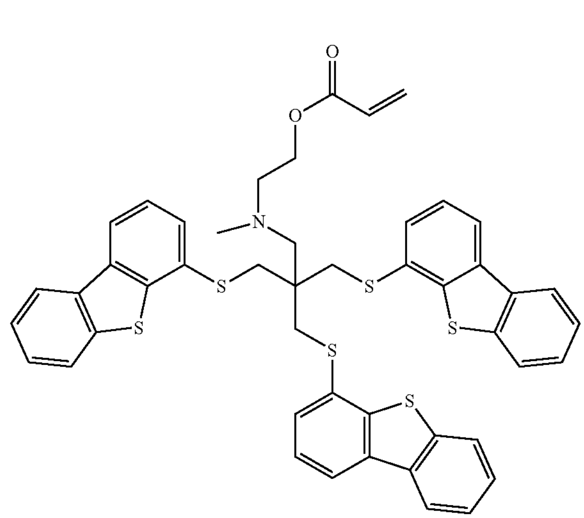
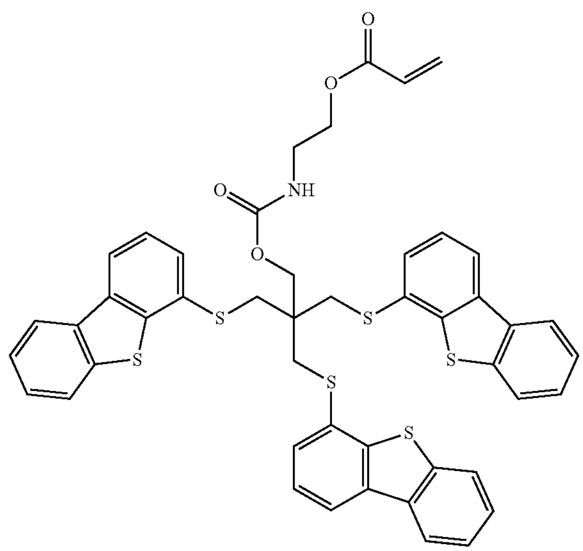
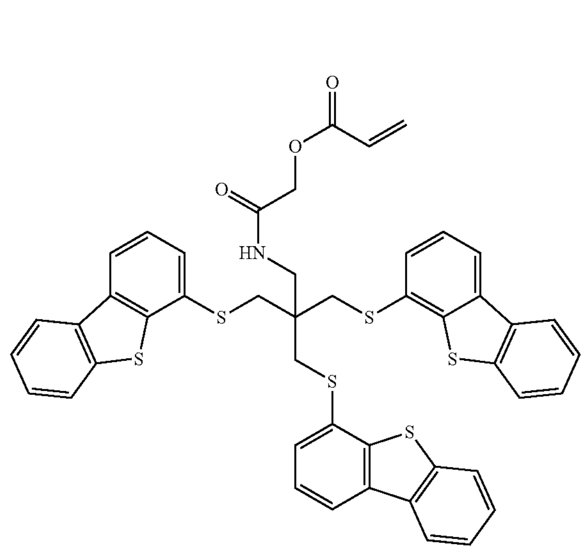
-continued -continued
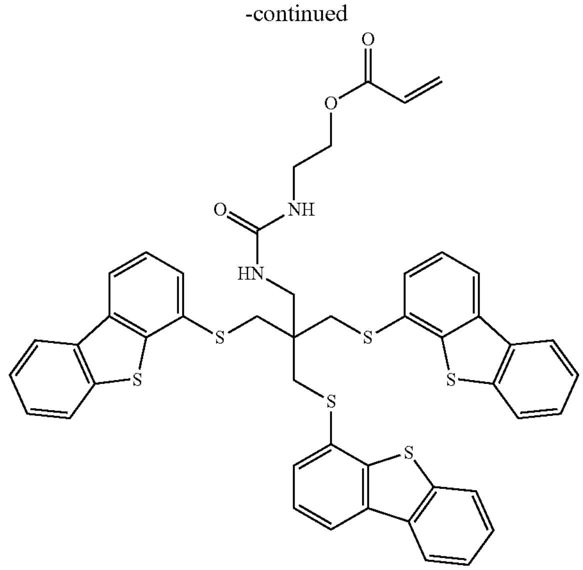
[Chem. 4]
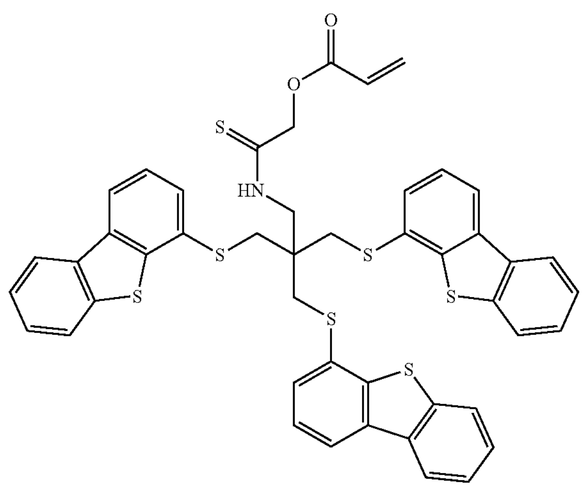
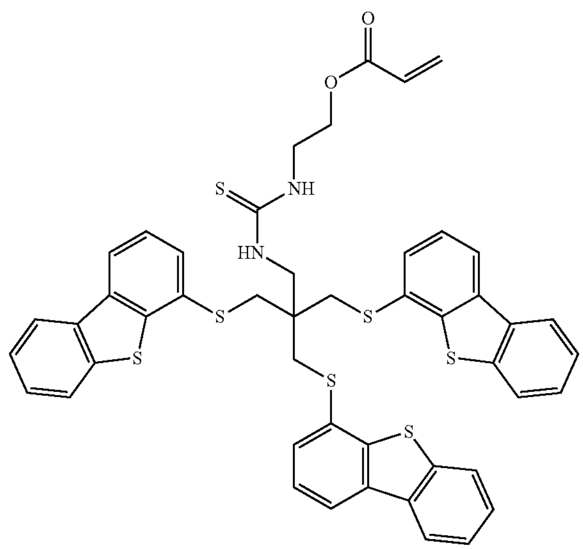
-continued
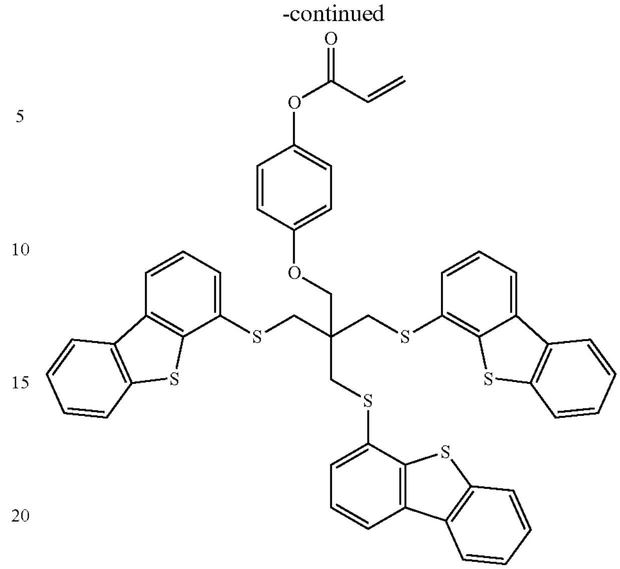
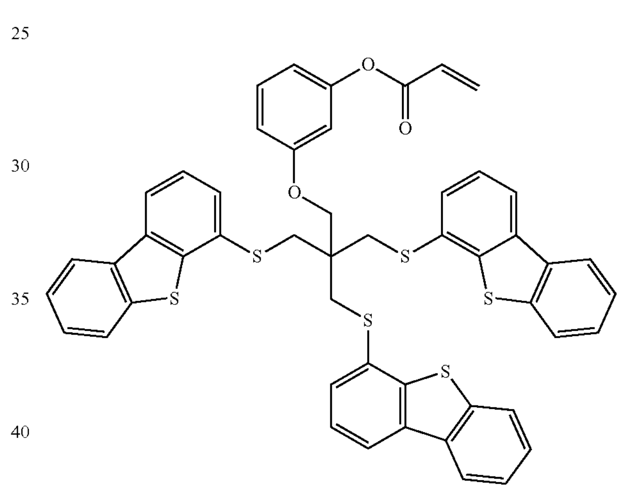
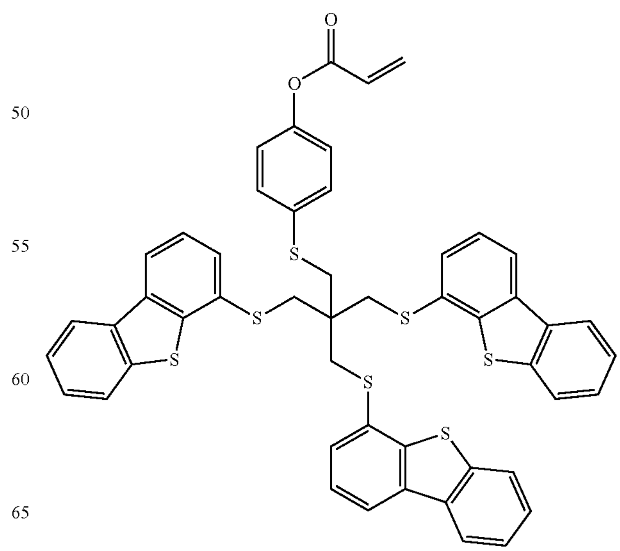

-continued
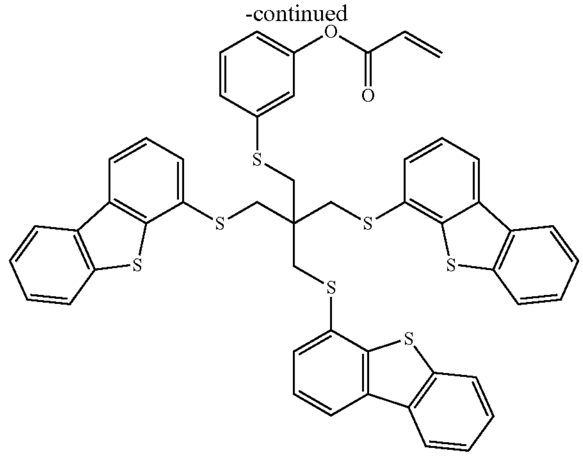
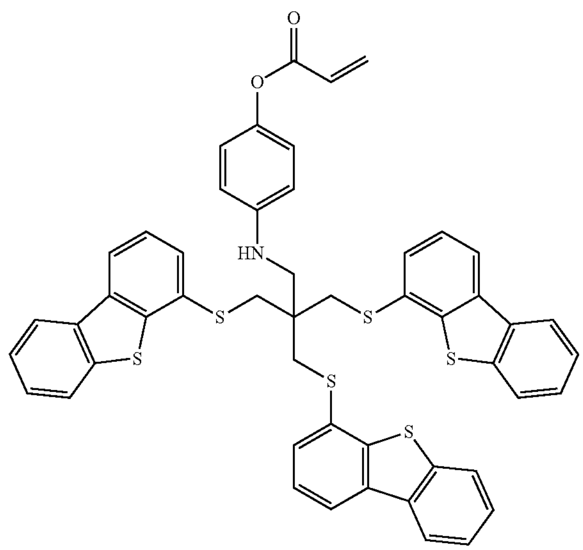
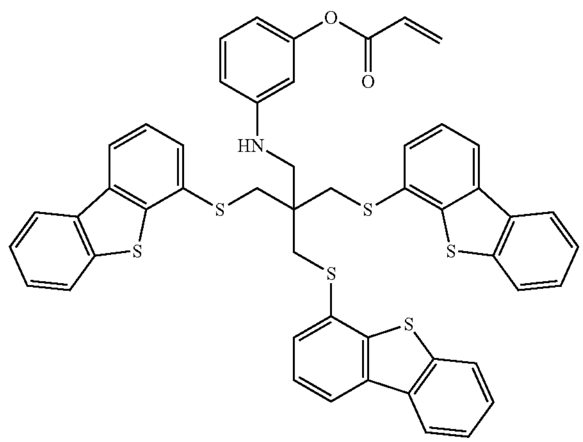
-continued
[Chem. 5]
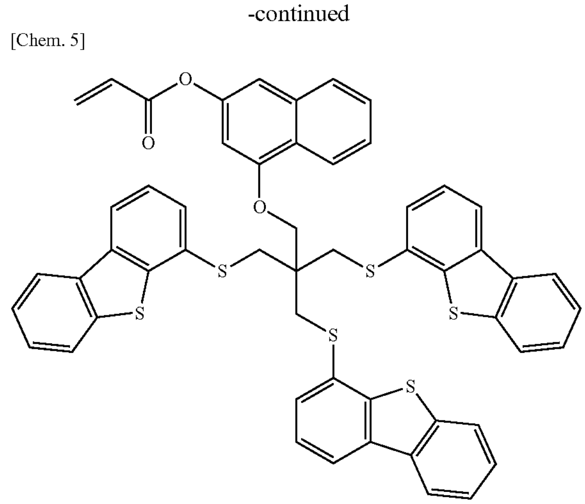
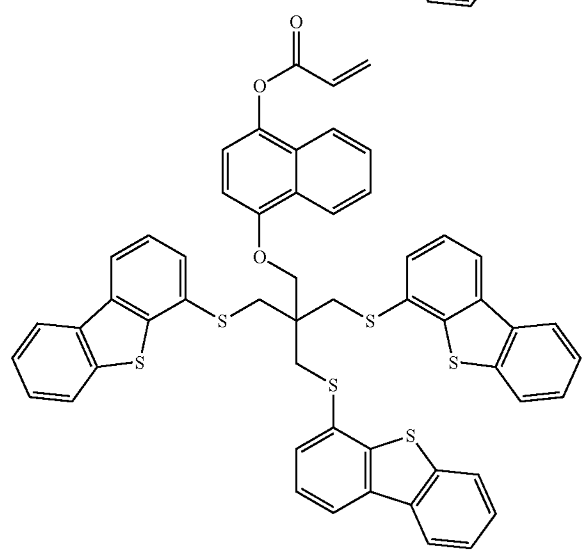
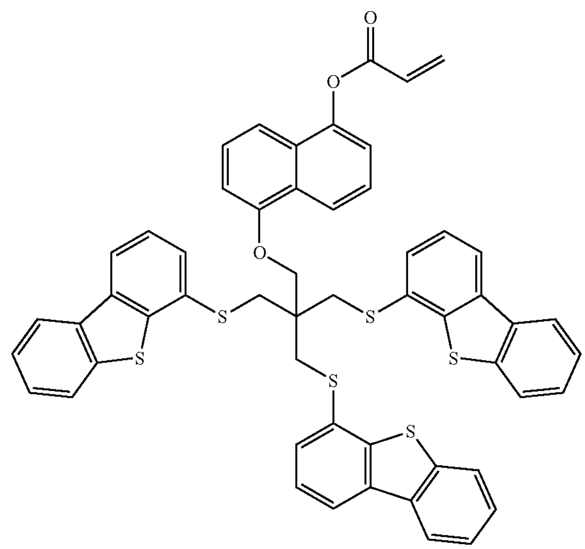

-continued
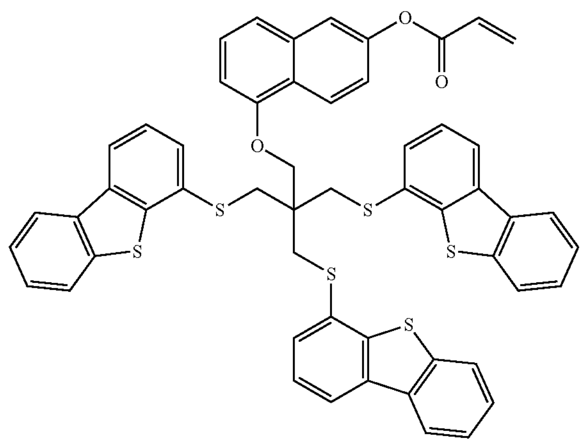
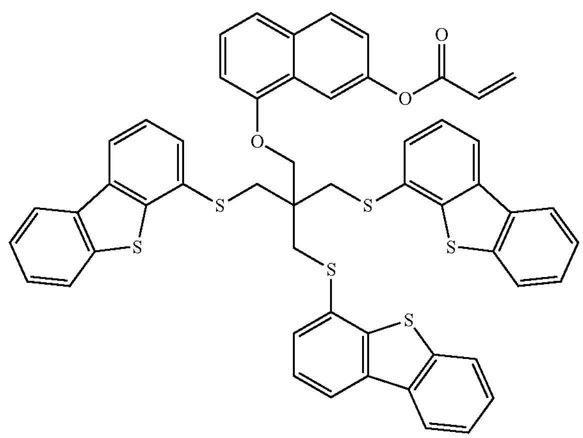
-continued
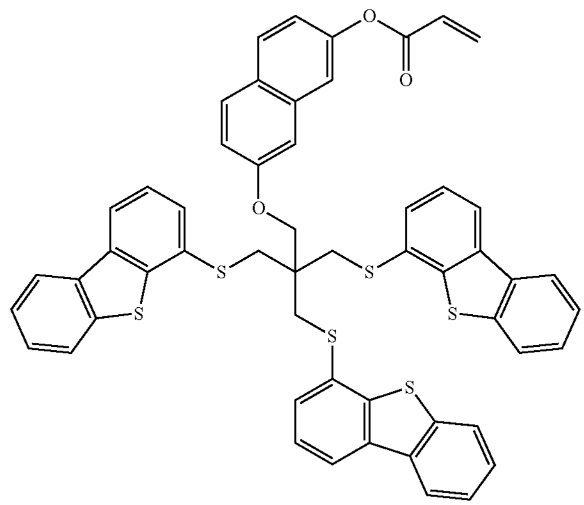
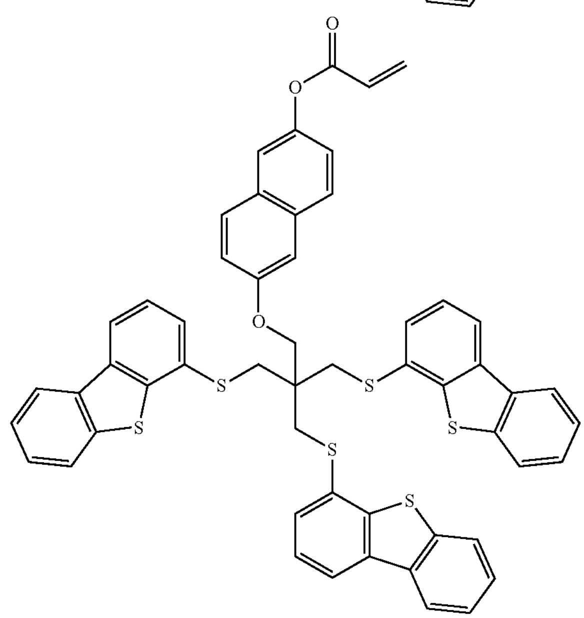
[Chem. 6]
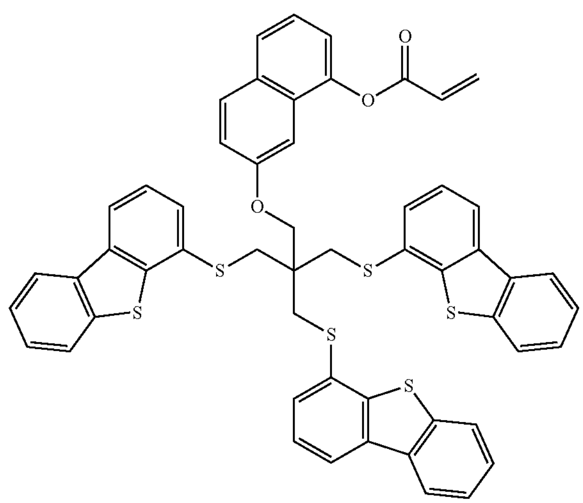
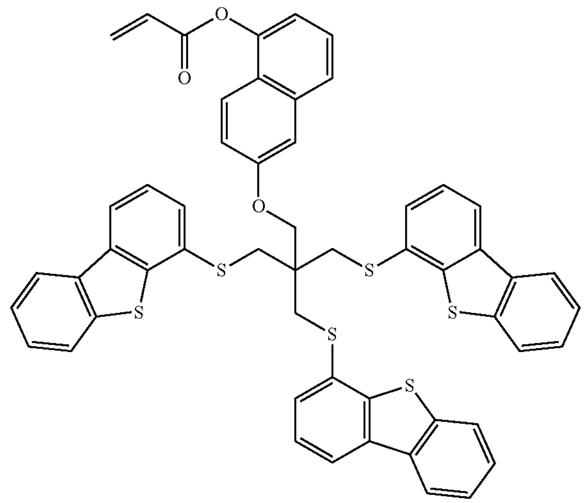

-continued
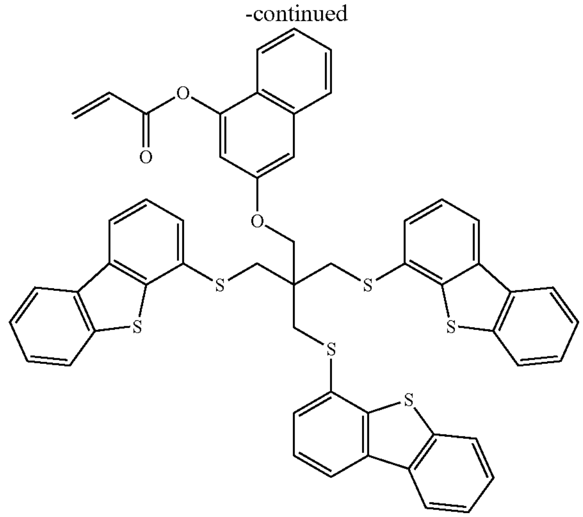
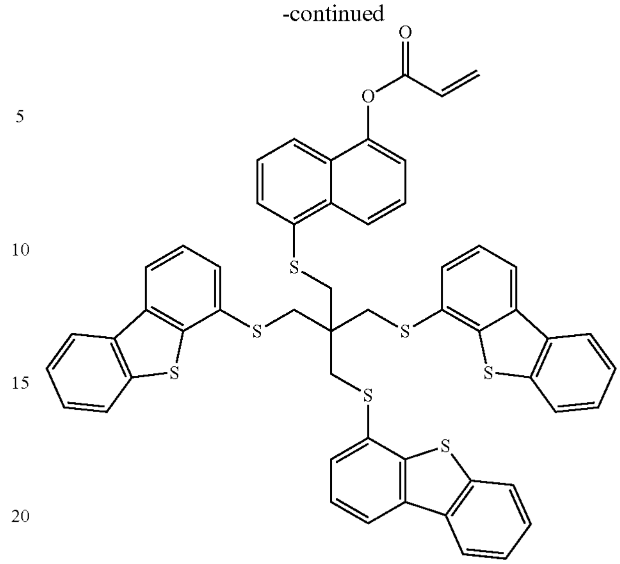
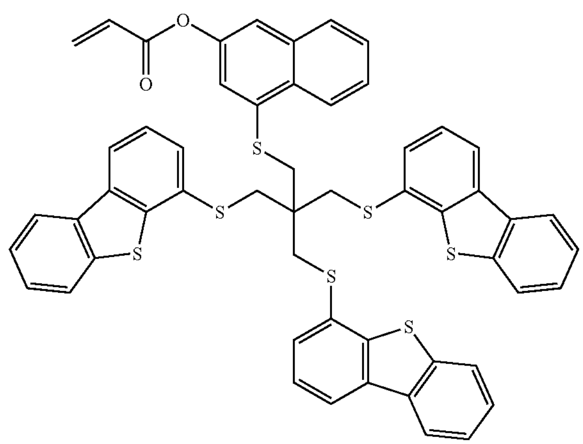
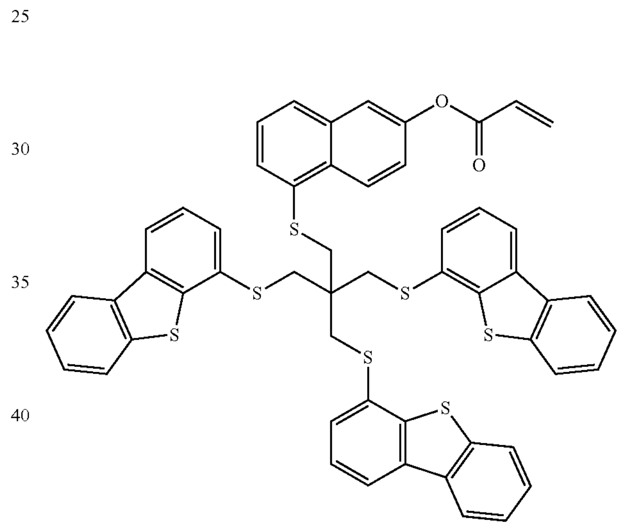
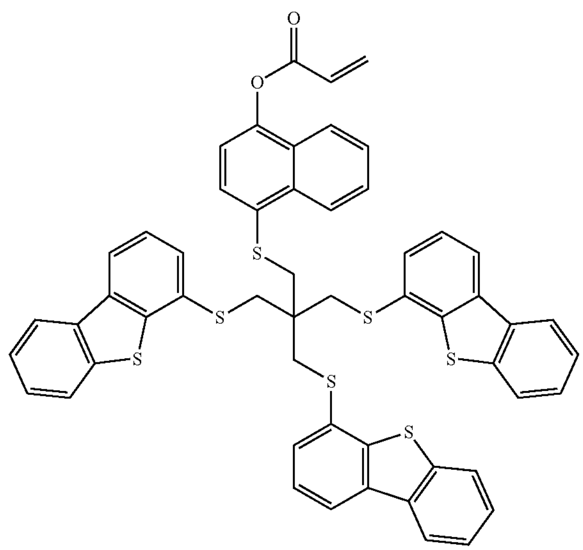
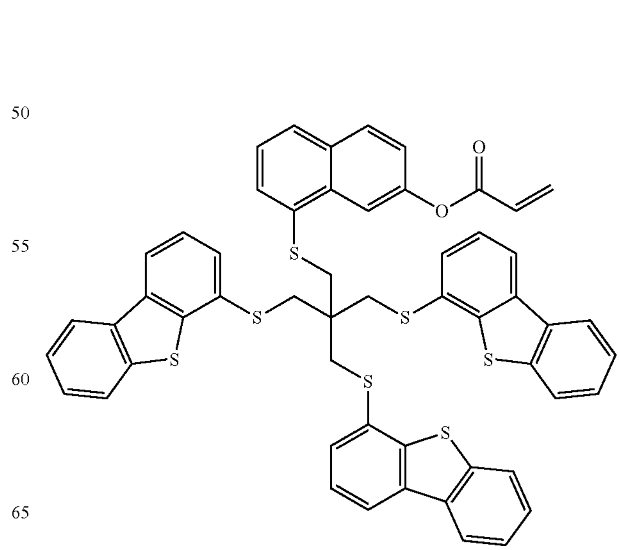
-continued -continued
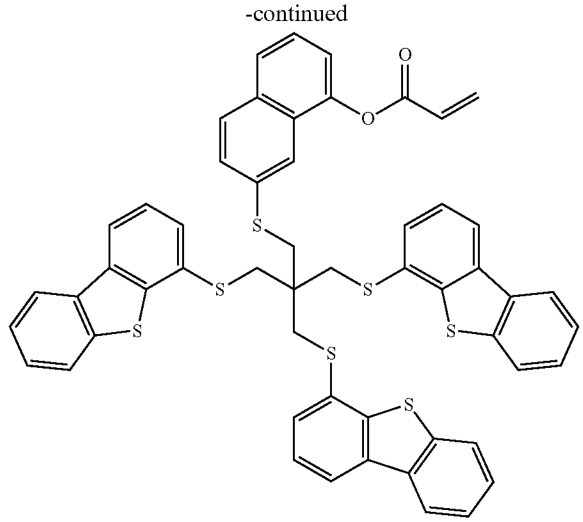
[Chem. 7]
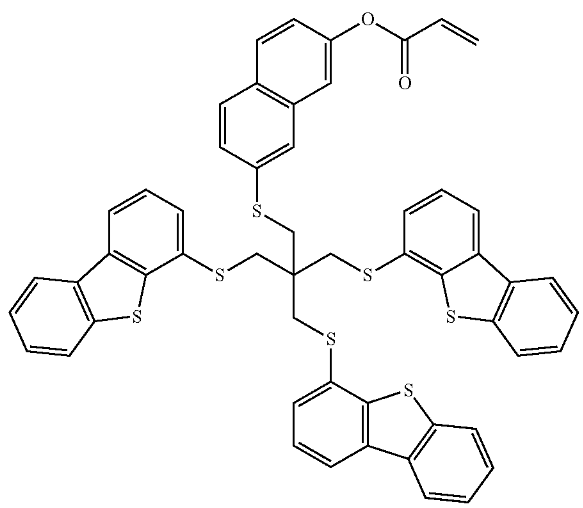
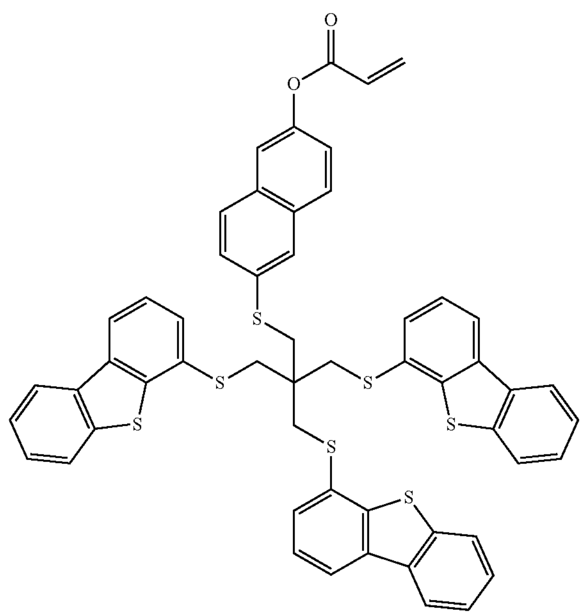
-continued
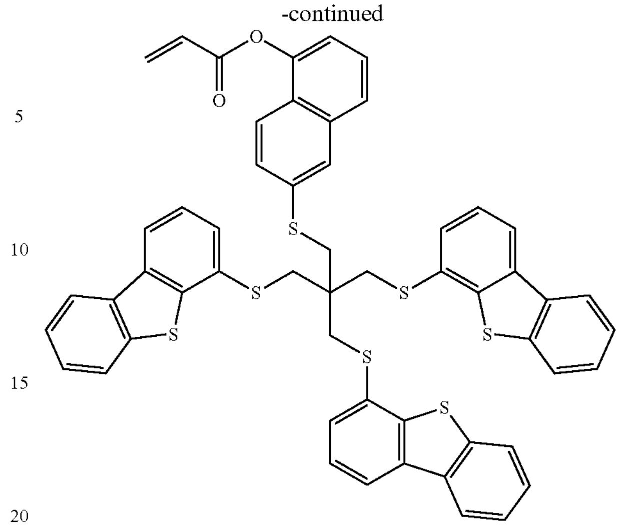
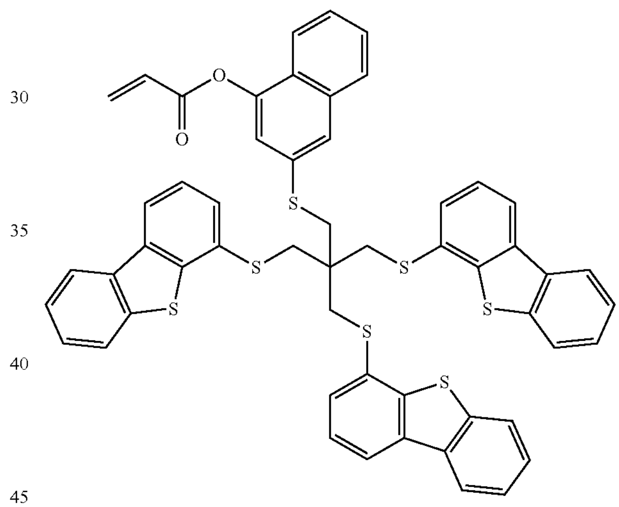
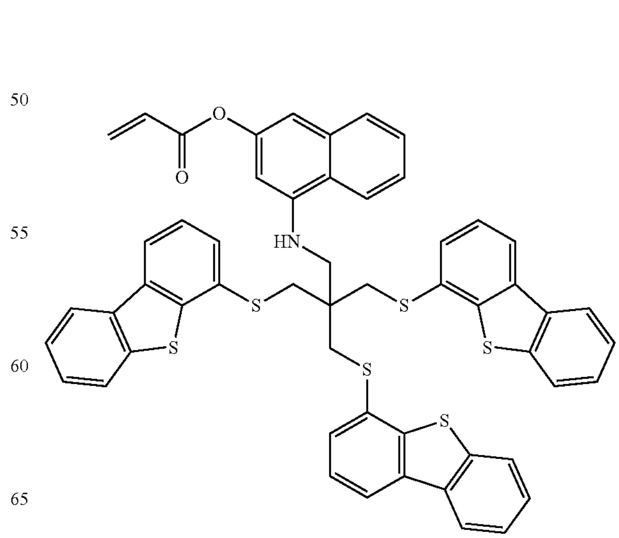
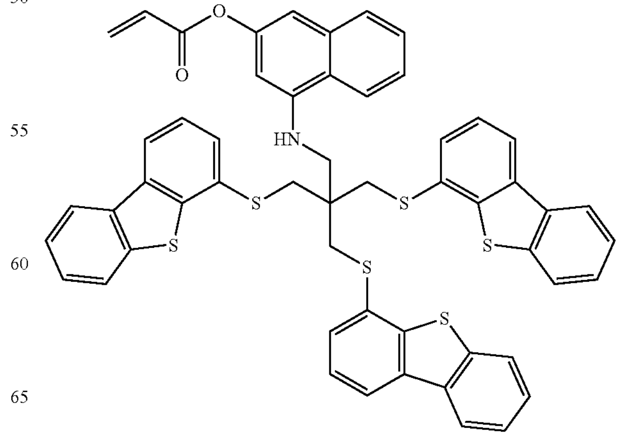
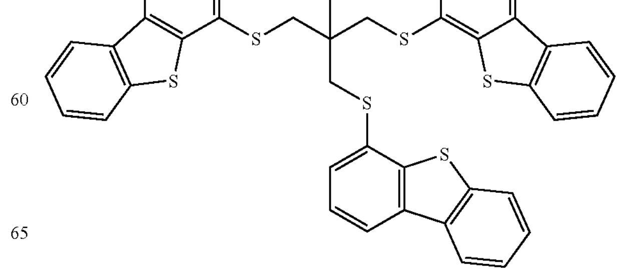
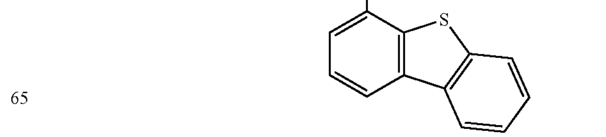

-continued
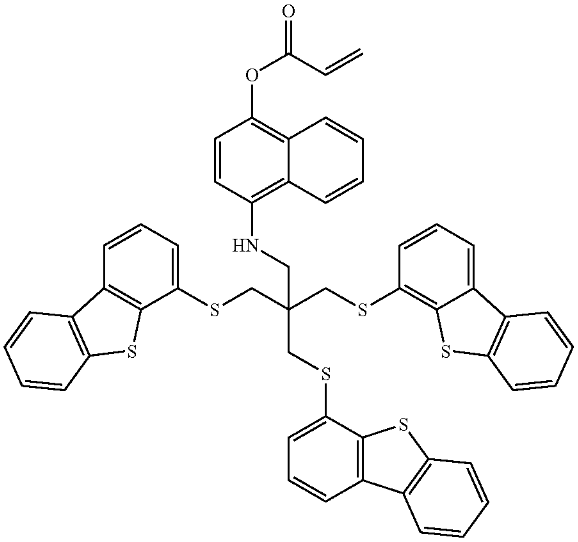
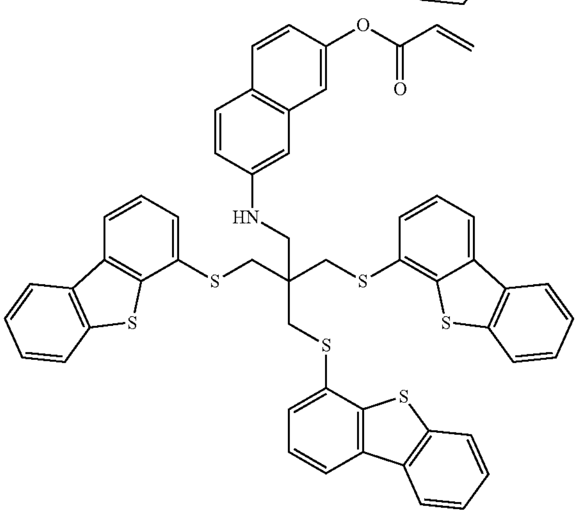
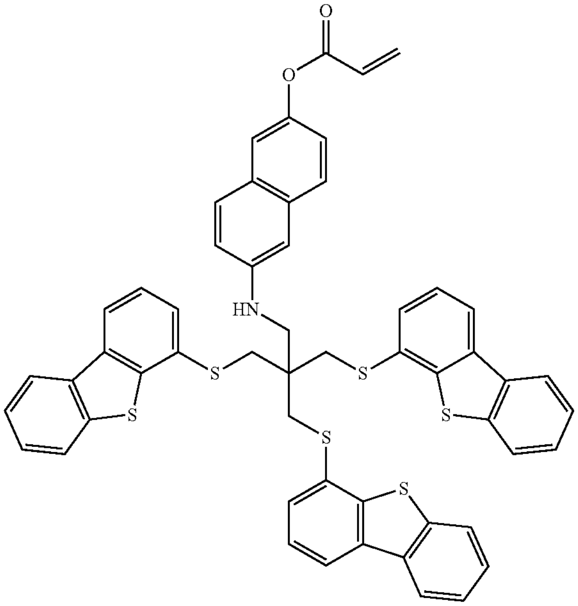
-continued
[Chem. 8]
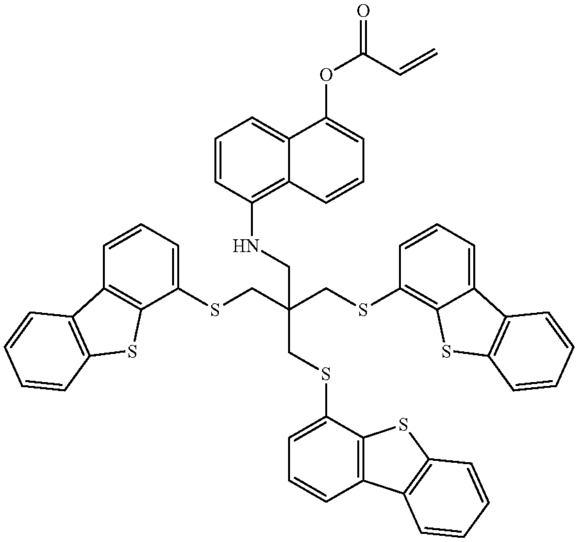
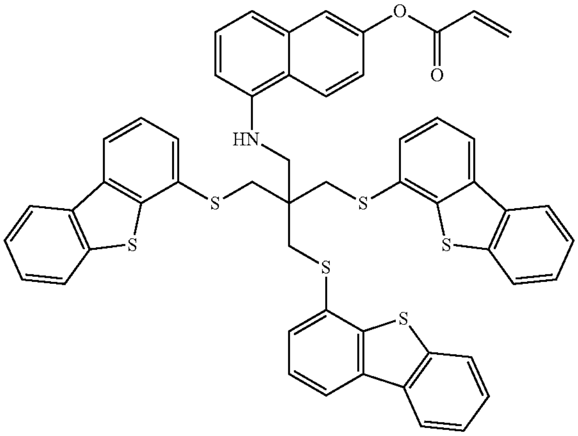
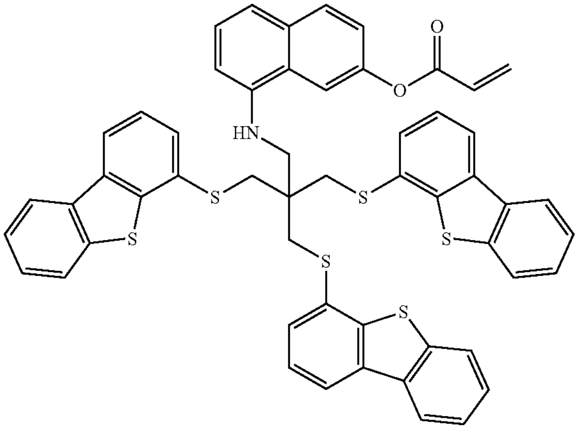

-continued
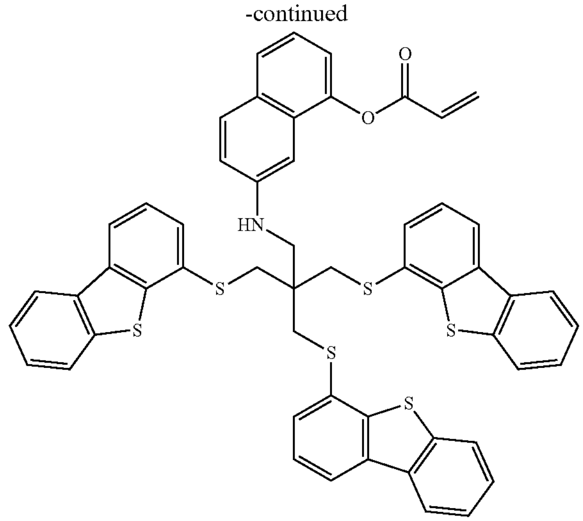
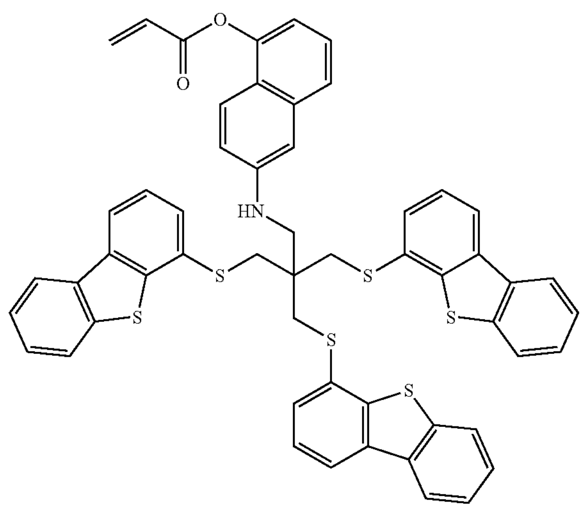
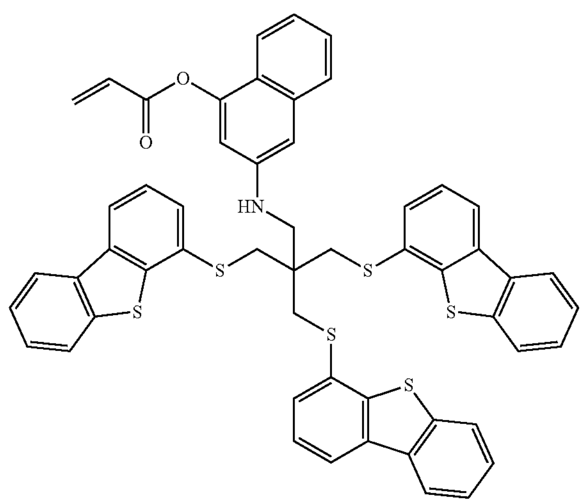
-continued
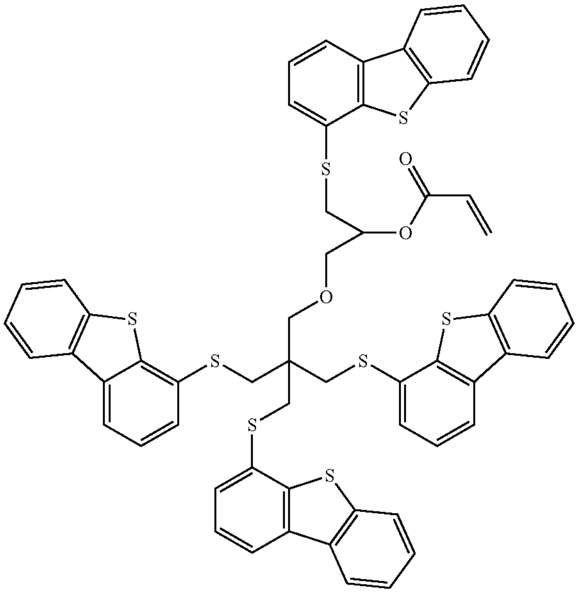
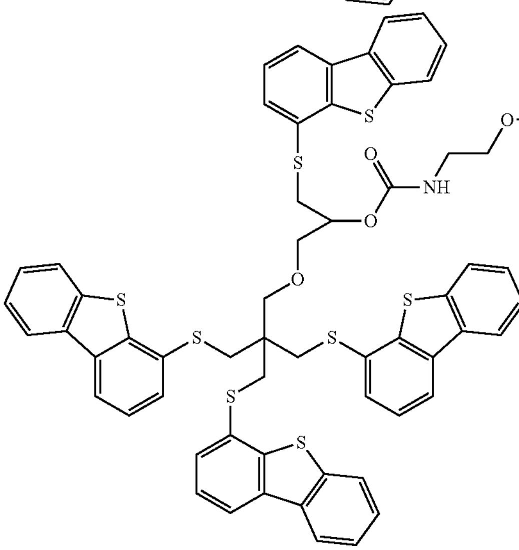
[Chem. 9]
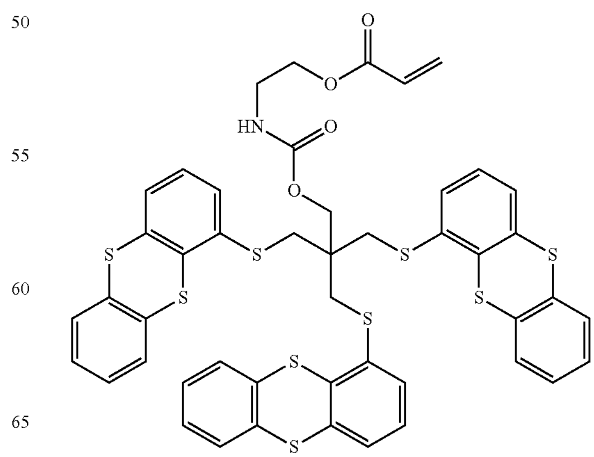

-continued
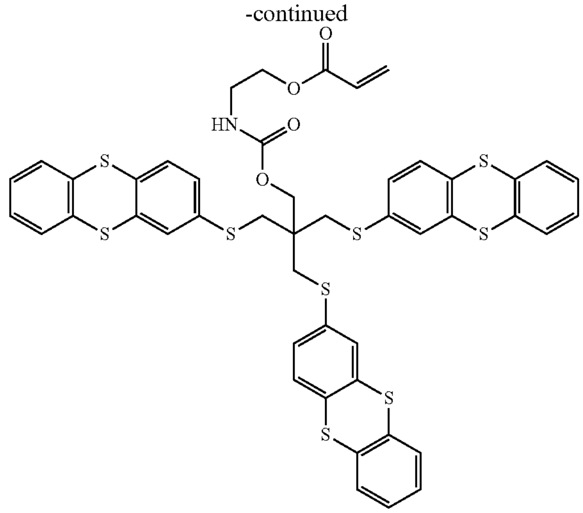
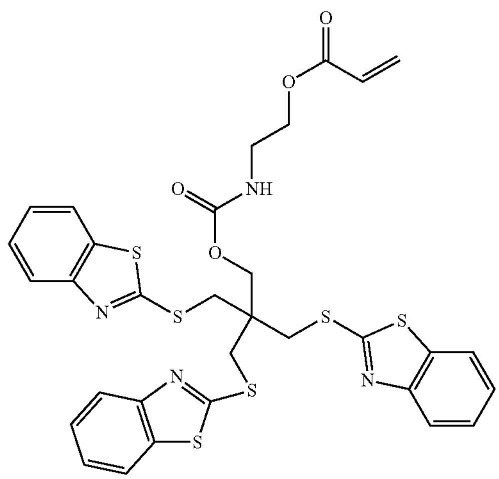
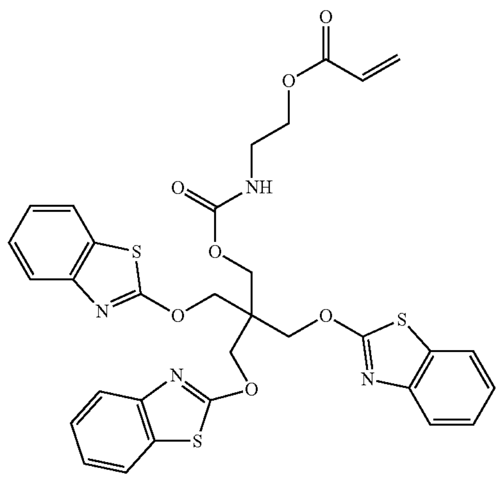
-continued
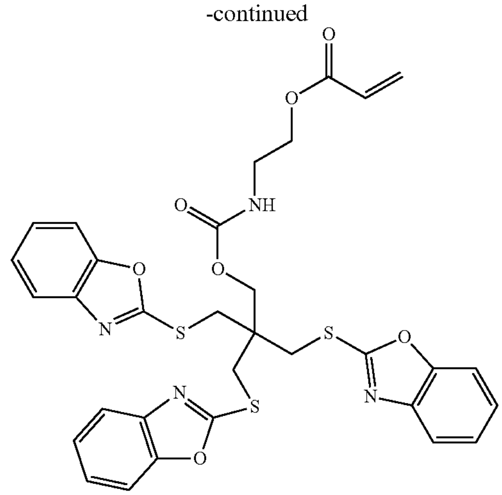
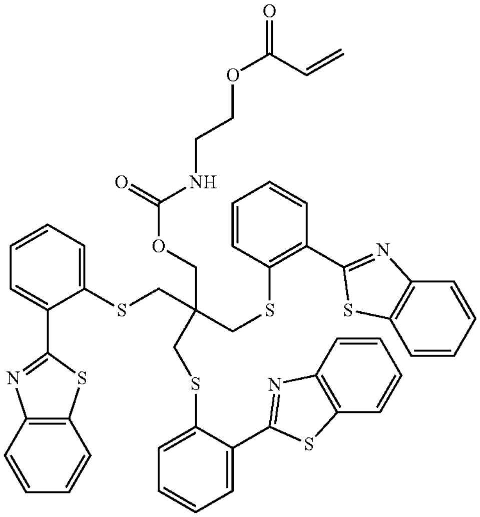
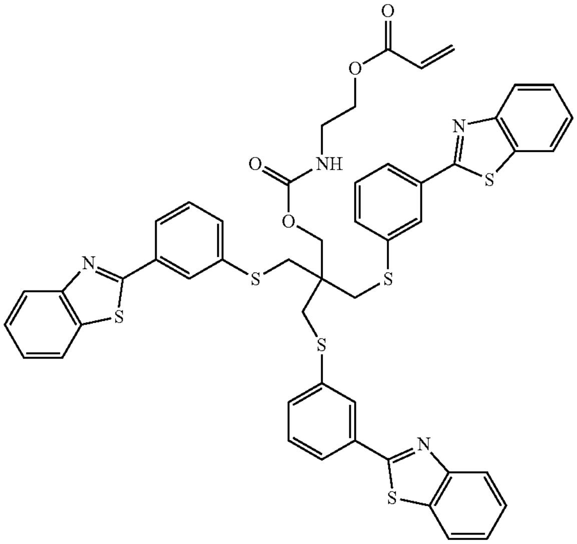

-continued
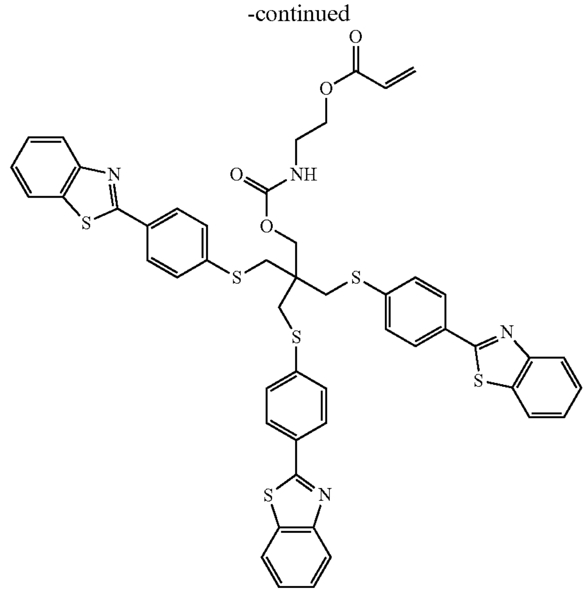
[Chem. 10]
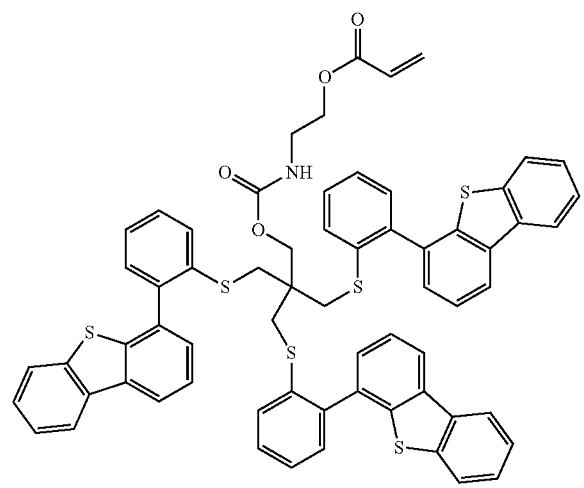
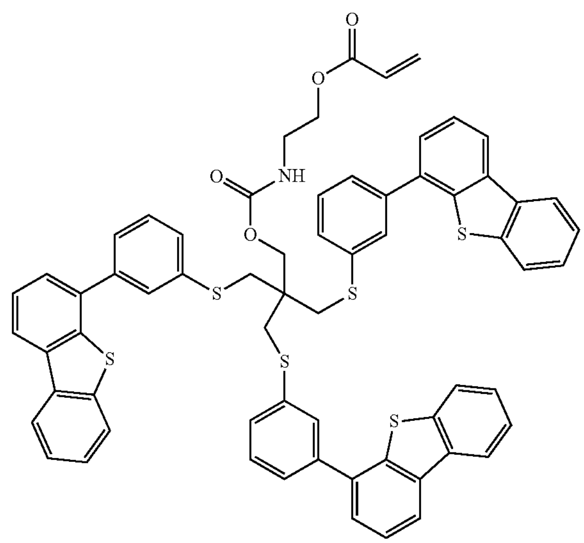
-continued
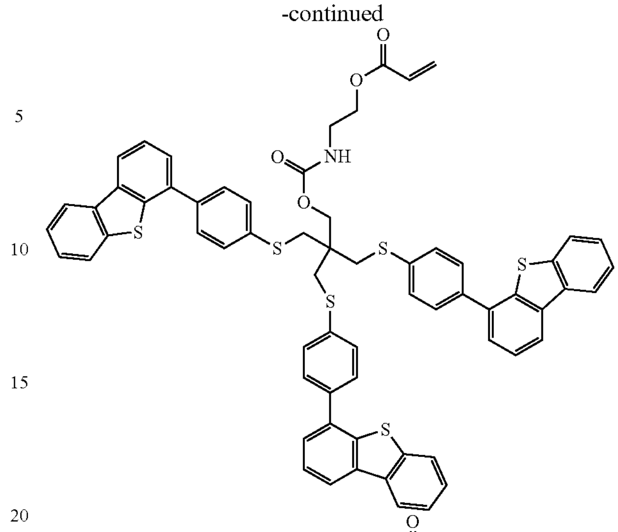
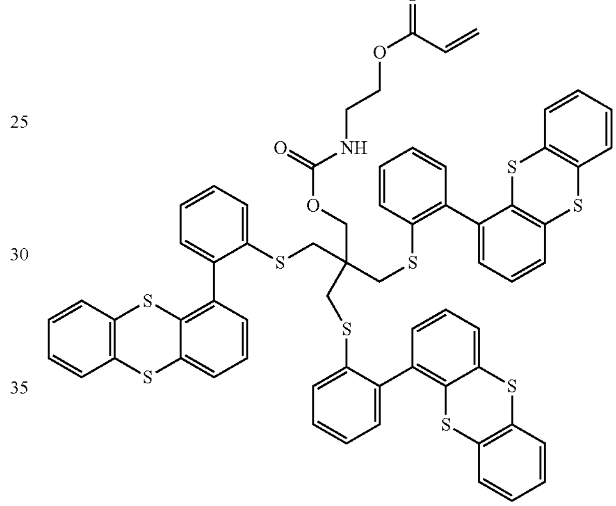
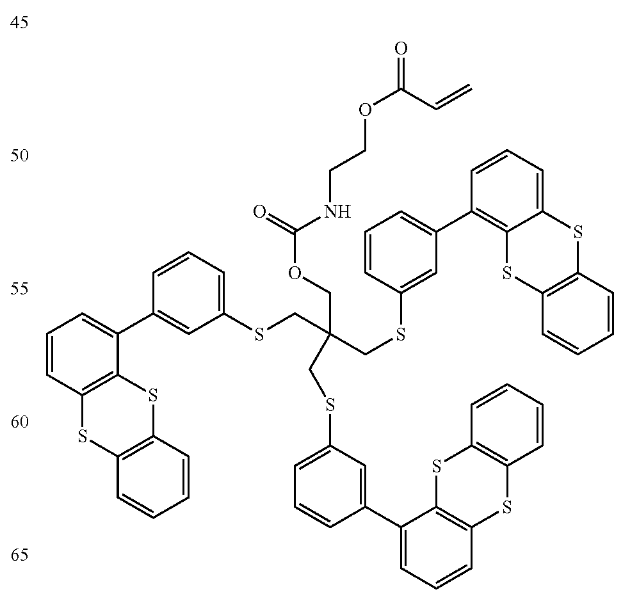

-continued
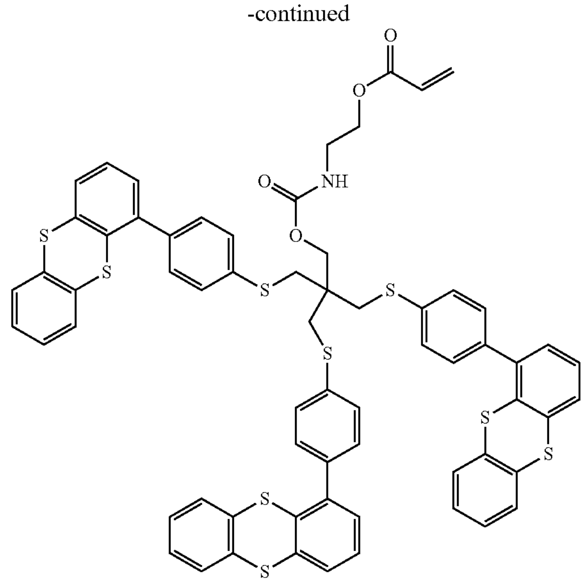
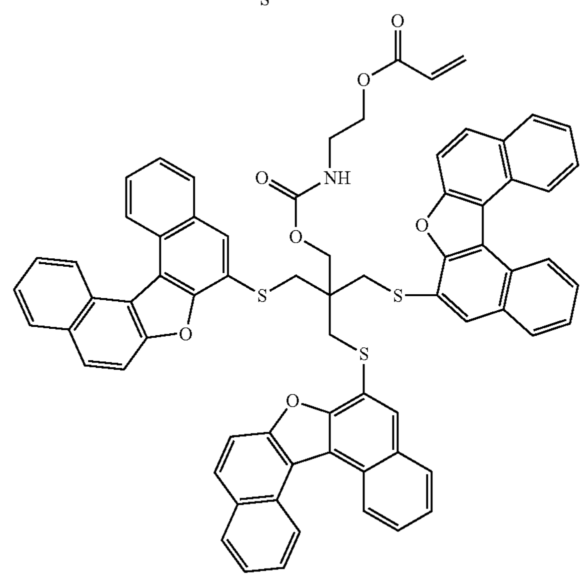
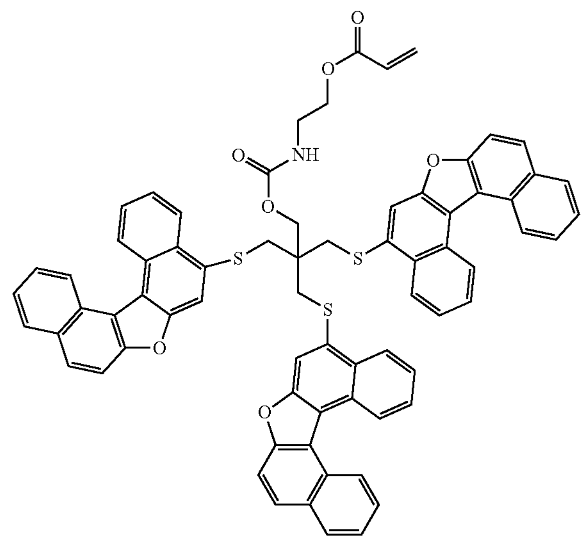
-continued
[Chem. 11]
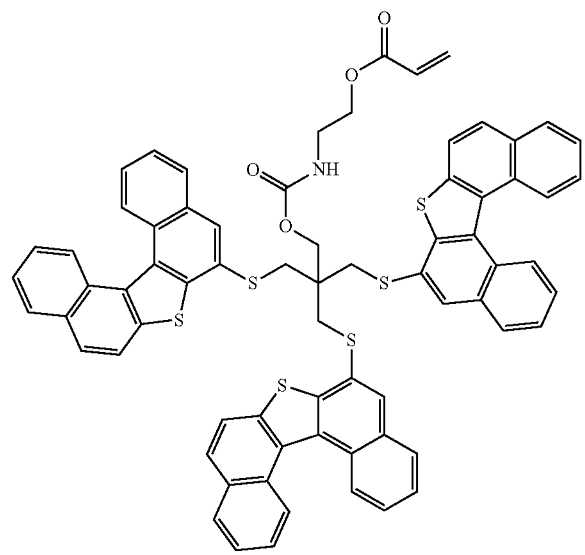
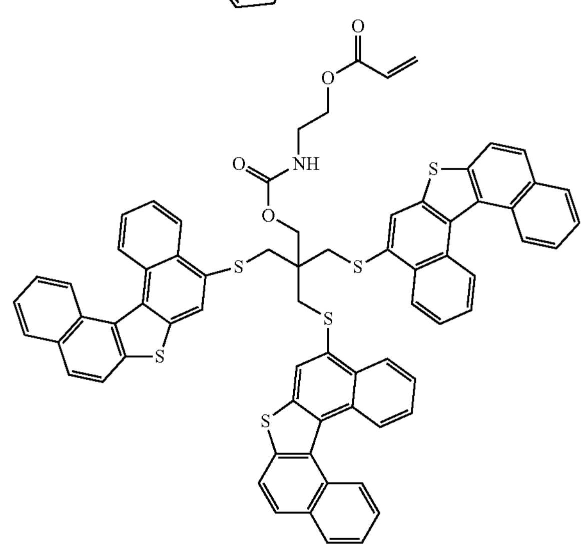
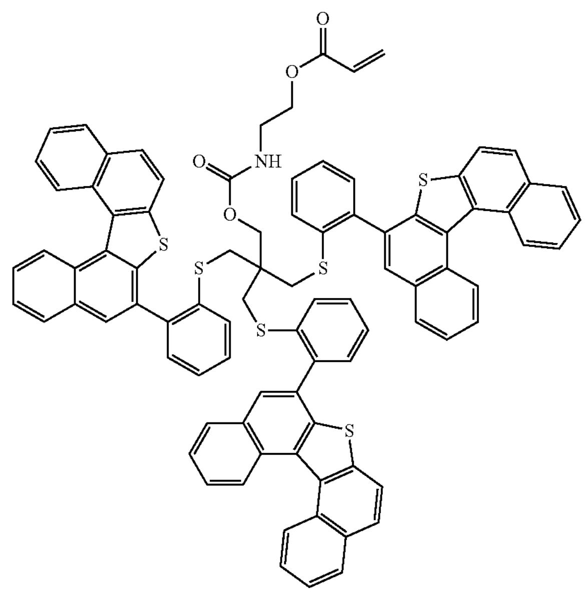

-continued
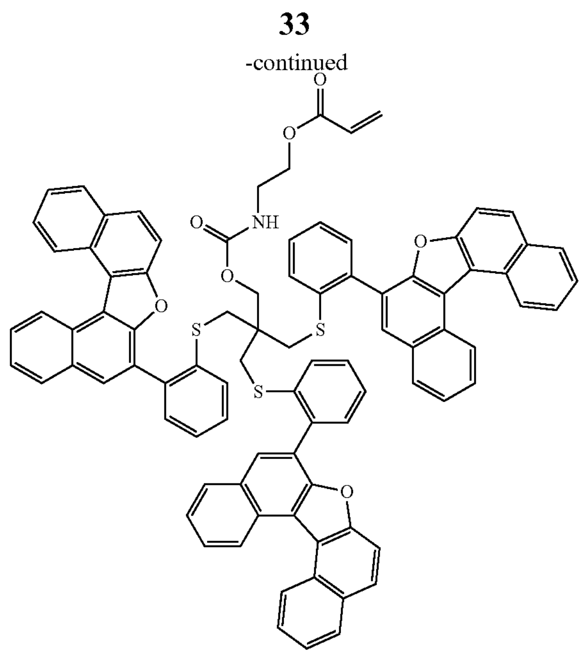
Specific examples other than the examples with m=1 and n=0 in formula (1) are as follows.
[Chem. 12]
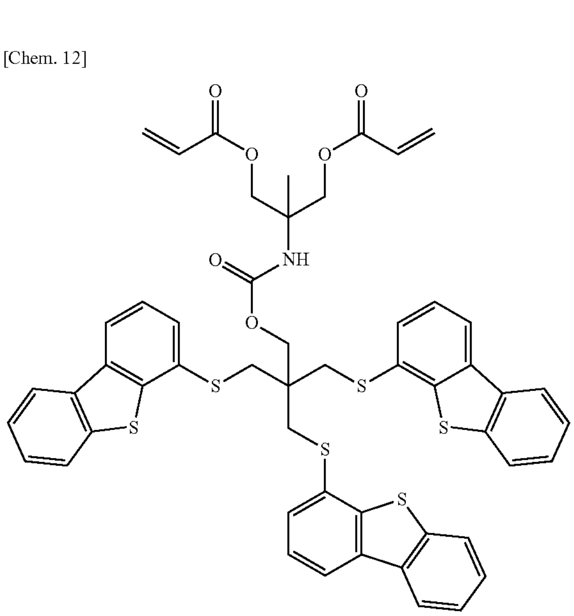
-continued
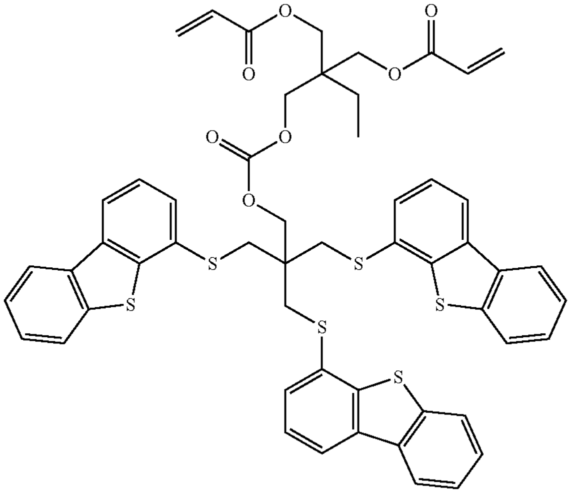
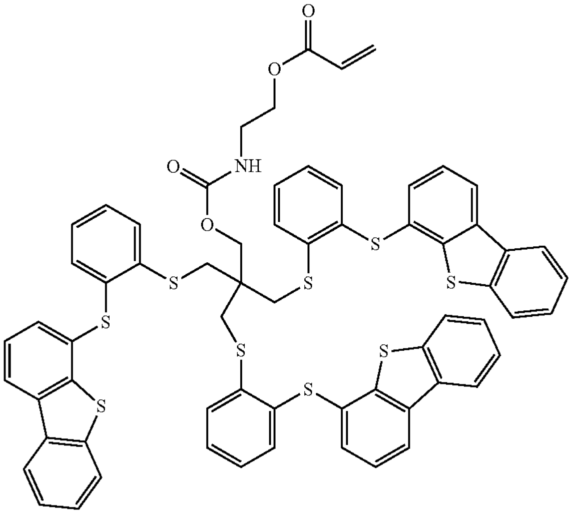
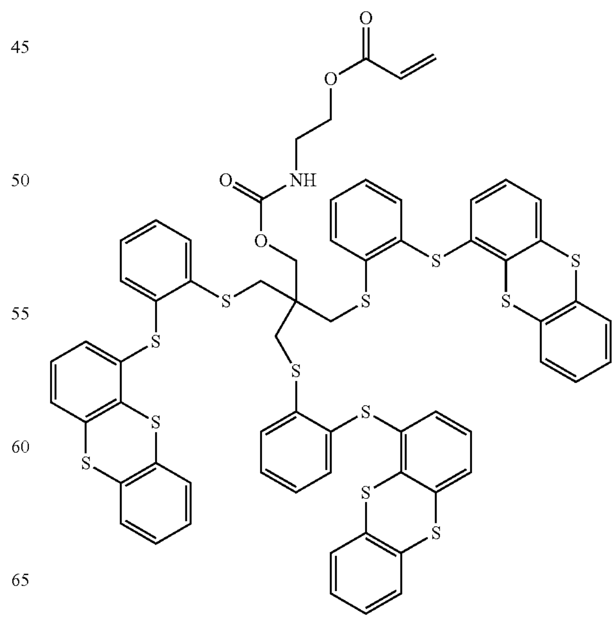

-continued

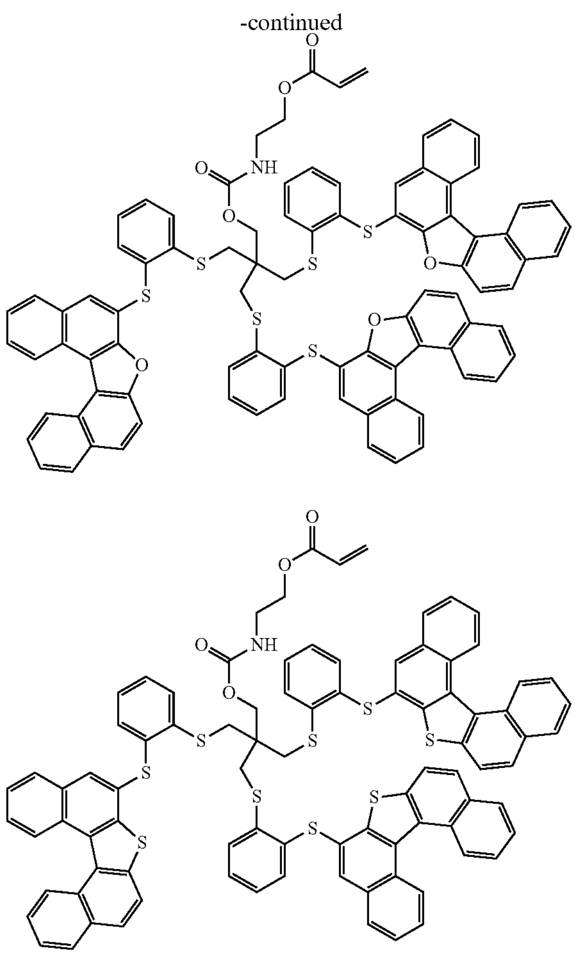

1-12. Synthesis Method

The compound of the invention represented by formula (1) can be synthesized using a combination of various known methods. Examples of the method for synthesizing the compound represented by formula (1) will be described using the following structural formulas.

Synthesis Example when n=0 in Formula (1)

First, a compound (a) having three Ys is subjected to a coupling reaction with a thiol compound (b) or a disulfide compound (b') to synthesize an intermediate (c), and the intermediate (c) is reacted with a compound (d) having a leaving group to synthesize a precursor (f) having a linker group L. A compound (d') that reacts with a nucleophile to form a hydroxy group can be used instead of (d) to synthesize the precursor (f). The precursor (f) can also be synthesized by reacting the intermediate (c) having the leaving group introduced thereinto with a nucleophile (e) having an amino group and a mercapto group $X^3$.

The precursor (f) is reacted with a (meth)acrylating agent (g-1) (acryloyl chloride, an acrylic anhydride, or an acrylate) to thereby obtain a compound (1A).

The compound (1A) can also be synthesized directly by causing the intermediate (c) to react with (g-2) into which a (meth)acryloyl group has been introduced in advance. The compound (1A) can also be synthesized by coupling (meth) acrylic acid (g-3) to a precursor (i) obtained by reacting the intermediate (c) with (h-1) having a leaving group.

$X^3$ in the nucleophile (e) represents a group selected from a hydroxy group, an amino group, a mercapto group, etc., and L and $L^1$ each represent an (m+1)-valent group optionally having a substituent. Y is a halogen atom, is preferably bromine or iodine, but may be chlorine. $Y^1$ to $Y^3$ each represent any of a halogen atom, an ester group, a sulfonate group, a carbonate group, and an isocyanate group. Z represents any of a halogen atom, a carboxyl group, an alkoxy group, and a sulfonyl group.

[Chem. 13]

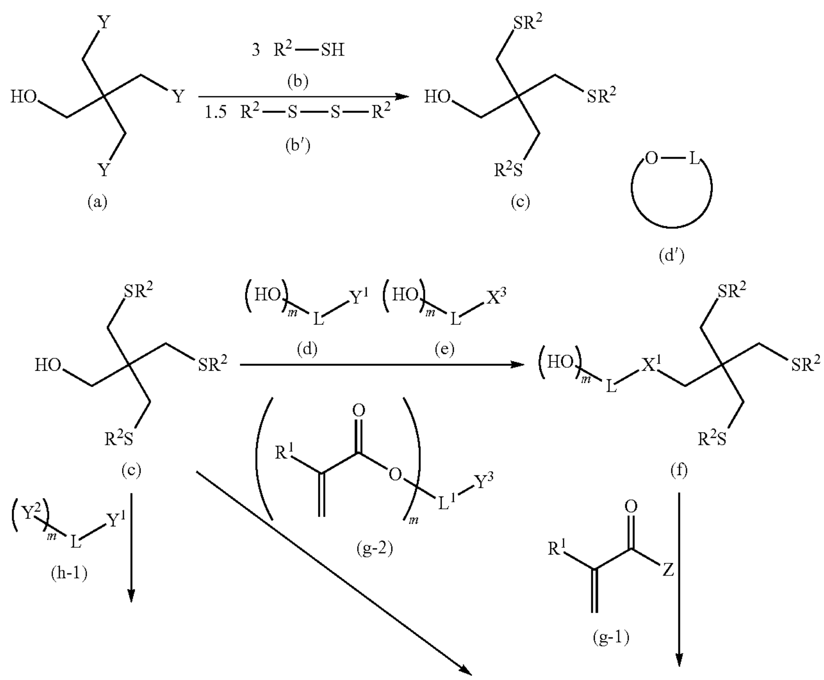

-continued

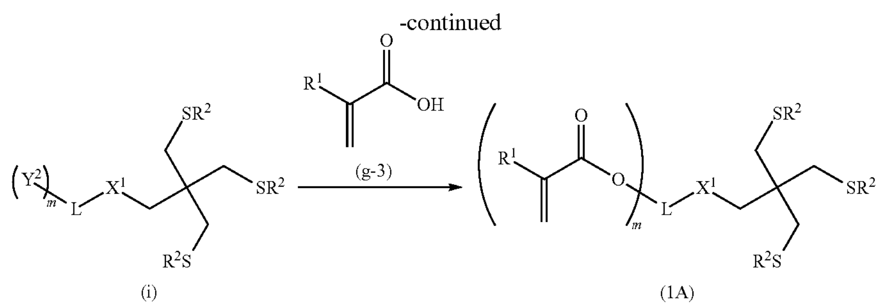

(i) (1A)

The intermediate (c) can be obtained by reacting the compound (a) with the compound (b') in the presence of a base or with the compound (b') in the presence of a base and a reducing agent.

When the intermediate (c) is synthesized, the organic solvent used is one of dimethoxyethane, tetrahydrofuran, methanol, ethanol, toluene, N,N-dimethylformamide, acetone, water, etc., or any combination of these solvents.

The base used is one of triethylamine, pyridine, sodium hydrogencarbonate, sodium carbonate, potassium carbonate, potassium tert-butoxide, etc., or any combination of these bases.

The reducing agent used is one reducing agent that reduces a disulfide bond to give thiol such as sodium formaldehyde sulfoxylate (Rongalite), sodium dithionite, sodium thiosulfate, sodium borohydride, or lithium aluminum hydride or any combination of these reducing agents.

By replacing all the Ys in the compound (a) with the moiety "$R^2$—S" in the compound (b) or the compound (b'), the intermediate (c) is obtained. Since the replacement proceeds sequentially, the reaction is stopped after confirmation by an appropriate method that all the Ys have been replaced. Examples of the method for checking the reaction state of the intermediate (c) include thin layer chromatography, liquid chromatography, gas chromatography, nuclear magnetic resonance measurement, and infrared absorption method.

To increase the purity of the intermediate (c), a column chromatograph filled with silica gel may be used.

The thus-obtained intermediate (c) is reacted with the compound (d) having a linker group L to obtain the precursor (f). The coupling reaction of (c) and (d) may be performed under any of acidic and basic conditions. A cross-coupling reaction using a metal catalyst or radical coupling may also be used. A method using (d') instead of the compound (d) can also be used to synthesize the precursor (f). When sulfur, a nitrogen atom optionally having a substituent, etc. is introduced into $X^1$ in the precursor (f), the precursor (f) can be synthesized by reacting the intermediate (c) with the nucleophile (e) having $X^3$ selected from a hydroxy group, an amino group, a mercapto group, etc. In this case, a method can be used in which the precursor (f) is obtained by converting the hydroxy group in the intermediate (c) to a leaving group such as a halogen atom, a sulfonate, or an acyl group and then reacting the resulting intermediate (c) with the nucleophile (e).

To increase the purity of the precursor (f), a column chromatograph filled with silica gel may be used, as in the case of the intermediate (c), or recrystallization using an appropriate solvent may be used.

A mixture in which the precursor (f) and one of an organic basic compound such as triethylamine, pyridine, or imidazole and an inorganic basic compound such as sodium carbonate or potassium carbonate or any combination thereof co-exist is reacted with the (meth)acrylating agent (g-1) (acryloyl chloride, an acrylic anhydride, or an acrylate), and the compound (1A) can thereby be obtained.

In this case, the organic solvent used is one of dimethoxyethane, dichloromethane, tetrahydrofuran, toluene, N,N-dimethylformamide, etc. or any combination thereof.

To increase the purity of the compound (1A), a column chromatograph filled with silica gel may be used, or recrystallization using an appropriate solvent may be performed, as in the cases of the intermediate (c) and the precursor (f).

The compound (1A) can also be synthesized from a compound (j) having four leaving groups such as halogen atoms. The precursor (f) can be synthesized by coupling the compound (j) to the thiol compound (b), the disulfide compound (b'), or the nucleophile (e) having a group selected from a hydroxy group, an amino group, a mercapto group, etc. In this case, no particular limitation is imposed on the reaction sequence, and the synthesis may be performed in any sequence using any method. The compound (1A) can be synthesized by reacting (g-1) with the precursor (f), as in the above case.

The compound (1A) can also be synthesized by reacting the (meth)acrylic acid (g-3) with the compound (i) obtained by coupling the compound (j) to a compound (h-2) and the thiol compound (b) or the disulfide compound (b') in any sequence using any method.

[Chem. 14]

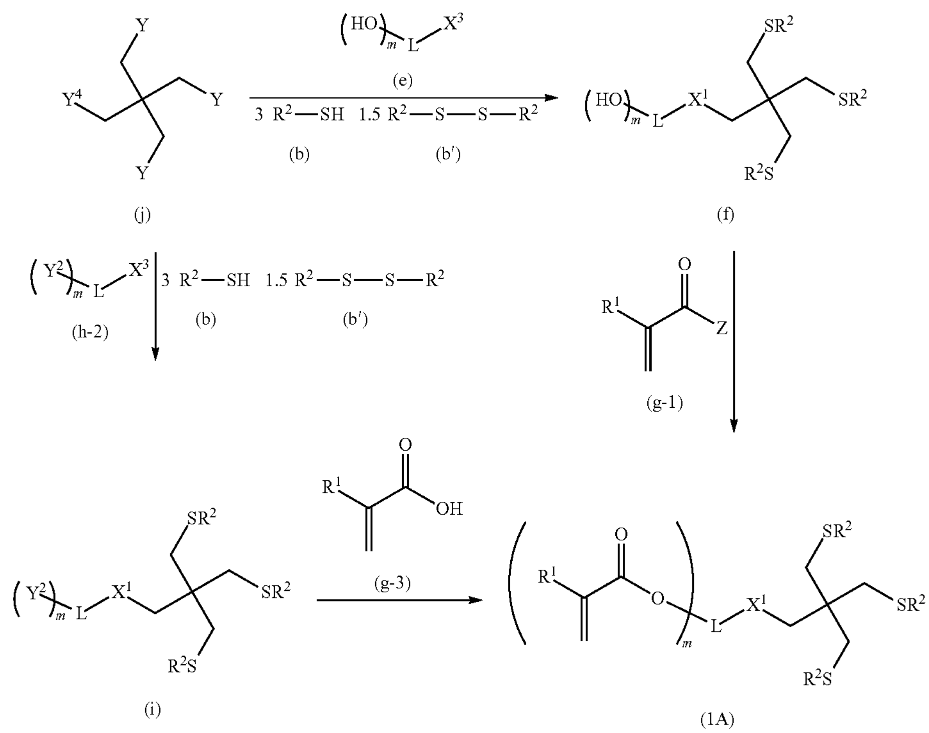

(e) (b) (b′) (j) (f) (h-2) (g-1) (g-3) (i) (1A)

Synthesis Example when n=1 in Formula (1)

The compound of the invention can be synthesized from the compound (a) having three Ys attached to a pentaerythritol skeleton, a compound (k) having one selected from a hydroxy group, an amino group, and a mercapto group and one Y, the thio compound (b), and a compound (g-2) having a (meth)acryloyl group using a combination of various known methods. For example, a compound (1B) can be synthesized by coupling the compound (a), the compound (k), the compound (b), and the compound (g-2) sequentially. No particular limitation is imposed on the sequence of the coupling reactions, and the coupling reactions may be performed in any sequence using any methods.

[Chem. 15]

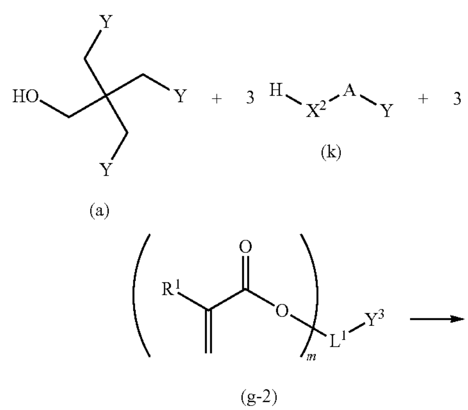

(a) (k) (b) (g-2)

-continued

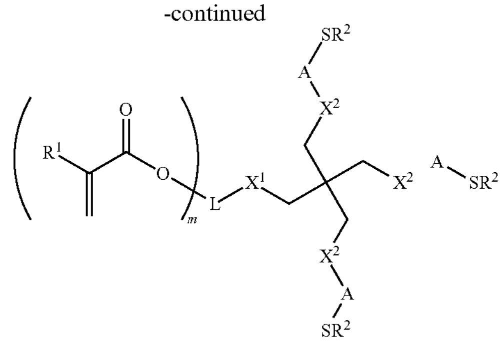

2. Polymerizable Composition of Invention

The polymerizable composition of the invention contains the compound of the invention represented by formula (1) and a polymerization initiator.

The polymerization initiator initiates a polymerization reaction of the (meth)acrylic groups, i.e., the polymerizable functional groups, in the compound of the invention represented by formula (1), and the polymer of the invention can thereby be obtained.

2-1. Polymerization Initiator

No particular limitation is imposed on the type of polymerization initiator, and a suitable polymerization initiator may be selected from known polymerization initiators according to the polymerization method. No limitation is imposed on the polymerization method, and the polymerization may be performed by any known method such as a bulk polymerization method, a solution polymerization method, a suspension polymerization method, an emulsion polymerization method, or a partial polymerization method.

Examples of the polymerization initiator contained in the polymerizable composition of the invention include radical polymerization initiators, redox-based polymerization initiators, anionic polymerization initiators, and cationic polymerization initiators. Moreover, a cationic photopolymerization initiator that generates cations that are active species under irradiation with light can also be used.

Examples of the polymerization initiator described later include initiators referred generally to as polymerization catalysts.

2-1-1. Radical Polymerization Initiator

<Photopolymerization Initiator>

Any known photo radical polymerization initiator can be used as the photopolymerization initiator that assists the polymerization of the polymerizable composition of the invention. Examples of the photopolymerization initiator used include azo-based compounds, azide-based compounds, organic peroxides, organic borates, onium salts, bisimidazole derivatives, titanocene compounds, iodonium salts, organic thiol compounds, halogenated hydrocarbon derivatives, acetophenones, benzophenones, hydroxybenzenes, thioxanthones, anthraquinones, ketals, acylphosphine oxides, sulfone compounds, carbamic acid derivatives, sulfonamides, triarylmethanols, and oxime esters. In particular, the photopolymerization initiator is preferably benzophenones, acylphosphine oxide compounds, oxime ester compounds, etc. in terms of compatibility, availability, etc.

Specific examples of the photopolymerization initiator include benzophenone, 2,4,6-trimethylbenzophenone, methylorthobenzoylbenzoate, 4-phenylbenzophenone, t-butylanthraquinone, 2-ethylanthraquinone, diethoxyacetophenone, 2-hydroxy-2-methyl-1-phenylpropan-1-one, oligo{2-hydroxy-2-methyl-1-[4-(1-methylvinyl)phenyl]propanone}, benzil dimethyl ketal, 1-hydroxycyclohexyl phenyl ketone, benzoin methyl ether, benzoin ethyl ether, benzoin isopropyl ether, benzoin isobutyl ether, 2-methyl-[4-(methylthio)phenyl]-2-morpholino-1-propanone, 2-benzyl-2-dimethylamino-1-(4-morpholinophenyl)-butanone-1, diethylthioxanthone, isopropylthioxanthone, 2,4,6-trimethylbenzoyldiphenylphosphine oxide, bis(2,6-dimethoxybenzoyl)-2,4,4-trimethylpentylphosphine oxide, bis(2,4,6-trimethylbenzoyl)-phenylphosphine oxide, 2-hydroxy-1-{4-[4-(2-hydroxy-2-methylpropionyl)benzyl]phenyl}-2-methylpropan-1-one, methylbenzoylformate, 1-[4-(phenylthio)-2-(O-benzoyloxime)]-1,2-octanedione, and 1-[9-ethyl-6-(2-methylbenzoyl)-9H-carbazol-3-yl]-1-(O-acetyloxime)ethenone.

Any one of these photopolymerization initiators may be used alone, or any combination of two or more of them may be used at any ratio.

The content of the photopolymerization initiator in the polymerizable composition of the invention is generally 0.01 parts by mass or more, preferably 0.02 parts by mass or more, and still more preferably 0.05 parts by mass or more based on 100 parts by mass of the total of all radical polymerizable compounds in the polymerizable composition. The upper limit of the content is generally 10 parts by mass or less, preferably 5 parts by mass or less, and still more preferably 3 parts by mass or less. If the amount of the photopolymerization initiator added is excessively large, the polymerization proceeds abruptly. In this case, not only does the birefringence of the cured product increase, but also its hue may deteriorate. If the content is excessively small, the polymerizable composition may not be polymerized sufficiently.

<Thermal Polymerization Initiator>

Any known thermal radical polymerization initiator can be used as the thermal polymerization initiator that assists the polymerization of the polymerizable composition of the invention. Examples of such a thermal radical polymerization initiator include organic peroxides and azo compounds. Of these, organic peroxides are preferred because air bubbles are unlikely to be formed in the polymer obtained through the polymerization reaction.

Specific examples of the organic peroxides include: ketone peroxides such as methyl ethyl ketone peroxide; peroxy ketals such as 1,1-di(t-hexylperoxy)-3,3,5-trimethylcyclohexane, 1,1-di(t-hexylperoxy)cyclohexane, and 1,1-di(t-butylperoxy)cyclohexane; hydroperoxides such as 1,1,3,3-tetramethylbutyl hydroperoxide, cumene hydroperoxide, and p-menthane hydroperoxide; dialkyl peroxides such as dicumyl peroxide and di-t-butyl peroxide; diacyl peroxides such as dilauroyl peroxide and dibenzoyl peroxide; peroxydicarbonates such as di(4-t-butylcyclohexyl)peroxydicarbonate and di(2-ethylhexyl)peroxydicarbonate; and peroxyesters such as t-butylperoxy-2-ethylhexanoate, t-hexylperoxyisopropyl monocarbonate, t-butyl peroxybenzoate, and 1,1,3,3-tetramethylbutyl-2-ethylhexanoate.

Specific examples of the azo compounds include 2,2'-azobisisobutyronitrile, 2,2'-azobis(2-methylbutyronitrile), 2,2'-azobis(2,4-dimethylvaleronitrile), 1,1'-azobis-1-cyclohexanecarbonitrile, dimethyl-2,2'-azobisisobutyrate, 4,4'-azobis-4-cyanovaleric acid, and 2,2'-azobis-(2-amidinopropane) dihydrochloride.

Any one of these thermal polymerization initiators may be used alone, or any combination of two or more may be used at any ratio.

The content of the thermal polymerization initiator in the polymerizable composition of the invention is generally 0.1 parts by mass or more, preferably 0.5 parts by mass or more, and more preferably 0.8 parts by mass or more based on 100 parts by mass of the total of all the radical polymerizable compounds in the polymerizable composition. The upper limit of the content is generally 10 parts by mass or less, preferably 5 parts by mass or less, and more preferably 2 parts by mass or less. If the amount of the thermal polymerization initiator is excessively large, the polymerization proceeds abruptly. In this case, not only is the optical uniformity of the polymer to be obtained impaired, but also its hue may deteriorate. If the content is excessively small, the thermal polymerization may not proceed sufficiently.

When the photopolymerization initiator is used in combination with the thermal polymerization initiator, the mass ratio is generally "100:1" to "1:100" ("the photopolymerization initiator:the thermal polymerization initiator", the same applies to this paragraph) and preferably "10:1" to "1:10." If the amount of the thermal polymerization initiator is excessively small, the polymerization may be insufficient. If the amount is excessively large, coloration may occur.

2-1-2. Redox-Based Polymerization Initiator

The redox-based polymerization initiator is a radical initiator that utilizes a redox reaction of a peroxide and a reducing agent used in combination, can generate radicals even at low temperature, and is generally used for emulsion polymerization etc.

Specific examples of the redox-based polymerization initiator include: combinations of dibenzoyl peroxide serving as a peroxide and an aromatic tertiary amine serving as a reducing agent such as N,N-dimethylaniline, N,N-dimethyl-p-toluidine, and N,N-bis(2-hydroxypropyl)-p-toluidine; combinations of a hydroperoxide serving as a peroxide and a metallic soap serving as a reducing agent; and combinations of a hydroperoxide serving as a peroxide and thioureas serving as a reducing agent.

As for a water-soluble redox-based polymerization initiator, a peroxide such as a persulfate, hydrogen peroxide, or a hydroperoxide is used in combination with a water-soluble inorganic reducing agent (such as $Fe^{2+}$ or $NaHSO_3$) or a water-soluble organic reducing agent (such as an alcohol or a polyamine).

A preferred range of the content of the redox-based polymerization initiator in the polymerizable composition of the invention is the same as that for the thermal polymerization initiator.

2-1-3. Anionic Polymerization Initiator

Examples of the anionic polymerization initiator used for the polymerizable composition of the invention include alkali metals, n-butyllithium, sodium amide, sodium naphthalenide, a Grignard reagent, lithium alkoxides, and alkali metal benzophenone ketyls. Any of these may be used alone, or any combination of two or more of them may be used at any ratio.

2-1-4. Cationic Polymerization Initiator

Examples of the cationic polymerization initiator used for the polymerizable composition of the invention include: Bronsted acids such as perchloric acid, sulfuric acid, and trichloroacetic acid; Lewis acids such as boron trifluoride, aluminum trichloride, aluminum tribromide, and tin tetrachloride; iodine; and chlorotriphenylmethane. Any one of these may be used alone, or any combination of two or more of them may be used at any ratio.

The amount of the anionic polymerization initiator or the cationic polymerizing agent in the polymerizable composition of the invention is generally 0.001 parts by mass or more, preferably 0.005 parts by mass or more, and still more preferably 0.01 parts by mass or more based on 100 parts by mass of the total of all anionically or cationically polymerizable compounds in the polymerizable composition. The upper limit of the amount is generally 5 parts by mass or less, preferably 1 part by mass or less, and more preferably 0.5 parts by mass or less. If the amount of the anionic or cationic polymerization initiator is less than 0.001 parts by mass, the reaction is not sufficient. If the amount added exceeds 5 parts by mass, it is difficult to achieve a sufficient pot life and a sufficient polymerization rate simultaneously.

2-1-5. Cationic Photopolymerization Initiator

The cationic photopolymerization initiator in the present invention is an initiator that generates cationic species under light. No particular limitation is imposed on the cationic photopolymerization initiator so long as it is a compound that generates cationic species upon irradiation with light, and onium salts are generally well known. Examples of the onium salts include diazonium salts of Lewis acids, iodonium salts of Lewis acids, and sulfonium salts of Lewis acids. Specific examples include a phenyldiazonium salt of boron tetrafluoride, a diphenyl iodonium salt of phosphorus hexafluoride, a diphenyl iodonium salt of antimony hexafluoride, a tri-4-methylphenylsulfonium salt of arsenic hexafluoride, and a tri-4-methylphenylsulfonium salt of antimony tetrafluoride. Preferably, aromatic sulfonium salts are used.

Specific examples of the cationic photopolymerization initiator include S,S,S',S'-tetraphenyl-S,S'-(4,4'-thiodiphenyl)disulfonium bishexafluorophosphate, diphenyl-4-phenylthiophenyl sulfonium hexafluorophosphate, and diphenyl-4-phenylthiophenyl sulfonium hexafluoroantimonate. Other examples include product name: UVI6992 manufactured by The Dow Chemical Company, product name: CPI-100P manufactured by San-Apro Ltd., product name: CPI-101A manufactured by San-Apro Ltd., product name: CPI-200K manufactured by San-Apro Ltd., and product name: Irgacure 270 manufactured by BASF (Irgacure is a registered trademark of BASF).

Any one of these cationic photopolymerization initiators may be used alone, or any combination of two or more of them may be used at any ratio.

The amount of the cationic photopolymerization initiator in the polymerizable composition of the invention is preferably from 0.02 parts by mass to 20 parts by mass inclusive and more preferably from 0.1 parts by mass to 10 parts by mass inclusive based on 100 parts by mass of the total of all cationically photopolymerizable compounds in the polymerizable composition. If the amount of the cationic photopolymerization initiator is lower than 0.02 parts by mass, the reaction is insufficient. If the amount added exceeds 20 parts by mass, it is difficult to achieve a sufficient pot life and a sufficient polymerization rate simultaneously.

The cationic photopolymerization initiator may be used in combination with the cationic polymerization initiator described above. In this case, the cationic polymerization initiator is used in an amount of generally 0.1 to 10 parts by mass and preferably 1 to 5 parts by mass based on 100 parts by mass of the cationically polymerizable compounds in the polymerizable composition. If the amount of the cationic polymerization initiator used is excessively small, a reduction in the polymerization rate occurs. If the amount is excessively large, the physical properties of the polymer to be obtained may deteriorate.

The cationic photopolymerization initiator may be used in combination with a cationic photopolymerization sensitizer. The cationic photopolymerization sensitizer is a formulation used when light emitted from a light source used for cationic photopolymerization does not match well the absorption wavelength of the cationic photopolymerization initiator. The cationic photopolymerization sensitizer is used in combination with the cationic photopolymerization initiator to transmit the energy of the irradiation light efficiently to the cationic photopolymerization initiator. Known examples of the cationic photopolymerization sensitizer include phenol-based compounds such as methoxyphenol (JP5-230189A), thioxanthone compounds (JP2000-204284A), and dialkoxyanthracene compounds (JP2000-119306A).

The cationic photopolymerization sensitizer is used in an amount of generally 0.2 to 5 parts by mass and preferably 0.5 to 1 part by mass based on 1 part by mass of the cationic photopolymerization initiator. If the amount of the cationic photopolymerization sensitizer is excessively small, the sensitizing effect may not be easily obtained. If the amount is excessively large, the physical properties of the polymer may deteriorate.

2-2. Polymerizable Compounds

The polymerizable composition of the invention may contain only one compound of the invention represented by formula (1) as a polymerizable compound or any combination of two or more compounds represented by formula (1) as polymerizable compounds at any ratio.

The polymerizable composition of the invention may contain an additional polymerizable compound other than the compound of the invention.

The content of the compound of the invention in the polymerizable composition of the invention is from 1% mass to 99% by mass inclusive and preferably from 5% mass to 95% by mass inclusive based on the total amount of solids in the polymerizable composition of the invention. If the content of the compound of the invention is less than 1% by mass, the effect obtained by using the compound of the invention is insufficient. If the content exceeds 99% by mass, curability tends to decrease.

Examples of the additional polymerizable compound include cationically polymerizable monomers, anionically polymerizable monomers, and radically polymerizable monomers. Any one of these polymerizable compounds may be used alone, or any combination of two or more of them may be used at any ratio. A polymerizable compound having two or more polymerizable functional groups per molecule (which may be referred to as a polyfunctional monomer) may also be used. When the polyfunctional monomer is used, a crosslinked structure is formed in the polymer, so that thermal stability, weather resistance, solvent resistance, etc. can be improved.

When the polymerizable composition of the invention contains the additional polymerizable compound other than the compound of the invention, the content of the additional polymerizable compound is from 0.1% mass to 10% by mass inclusive and preferably from 0.3% mass to 5% by mass inclusive based on the total amount of solids in the polymerizable composition of the invention. If the content of the additional polymerizable compound is less than 0.1% by mass, the effect of imparting characteristics by the addition of the additional polymerizable compound is not sufficient. If the content exceeds 5% by mass, problems such as a reduction in optical characteristics and a reduction in strength tend to occur.

<Cationically Polymerizable Monomer>

Examples of the cationically polymerizable monomer include compounds having an oxirane ring, styrene and derivatives thereof, vinylnaphthalene and derivatives thereof, vinyl ethers, N-vinyl compounds, and compounds having an oxetane ring.

In particular, a compound having at least an oxetane ring is preferably used, and a combination of a compound having an oxetane ring and a compound having an oxirane ring is used more preferably.

Examples of the compound having an oxirane ring include prepolymers having two or more oxirane rings per molecule.

Examples of such prepolymers include alicyclic polyepoxies, polyglycidyl esters of polybasic acids, polyglycidyl ethers of polyhydric alcohols, polyglycidyl ethers of polyoxyalkylene glycols, polyglycidyl ethers of aromatic polyols, hydrogenated compounds of polyglycidyl ethers of aromatic polyols, urethane polyepoxy compounds, and epoxidized polybutadienes.

Examples of the styrene and derivatives thereof include styrene, p-methylstyrene, p-methoxystyrene, β-methylstyrene, p-methyl-β-methylstyrene, α-methylstyrene, p-methoxy-β-methylstyrene, and divinylbenzene.

Examples of the vinylnaphthalene and derivatives thereof include 1-vinylnaphthalene, α-methyl-1-vinylnaphthalene, β-methyl-1-vinylnaphthalene, 4-methyl-1-vinylnaphthalene, and 4-methoxy-1-vinylnaphthalene.

Examples of the vinyl ethers include isobutyl ether, ethyl vinyl ether, phenyl vinyl ether, p-methylphenylvinyl ether, and p-methoxyphenylvinyl ether.

Examples of the N-vinyl compounds include N-vinylcarbazole, N-vinylpyrrolidone, N-vinylindole, N-vinylpyrrole, and N-vinylphenothiazine.

Examples of the compounds having an oxetane ring include various known oxetane compounds described in JP2001-220526A, JP2001-310937A, etc.

Any one of these cationically polymerizable monomers may be used alone, or any combination of two or more of them may be used at any ratio.

<Anionically Polymerizable Monomer>

Examples of the anionically polymerizable monomer include hydrocarbon monomers and polar monomers.

Examples of the hydrocarbon monomers include styrene, α-methylstyrene, butadiene, isoprene, vinylpyridine, vinylanthracene, and derivatives thereof.

Examples of the polar monomers include: methacrylates (such as methyl methacrylate, ethyl methacrylate, and isopropyl methacrylate); acrylates (such as methyl acrylate and ethyl acrylate); vinyl ketones (such as methyl vinyl ketone, isopropyl vinyl ketone, cyclohexyl vinyl ketone, and phenyl vinyl ketone); isopropenyl ketones (such as methyl isopropenyl ketone and phenyl isopropenyl ketone); and other polar monomers (such as acrylonitrile, acrylamide, nitroethylene, methylene malonate, cyanoacrylates, and vinylidene cyanide).

Any one of these anionically polymerizable monomers may be used alone, or any combination of two or more of them may be used at any ratio.

<Radically Polymerizable Monomer>

The radically polymerizable monomer is a compound having at least one ethylenically unsaturated double bond per molecule, and examples thereof include (meth)acrylates, (meth)acrylamides, vinyl esters, and styrenes.

Examples of the (meth)acrylates include methyl (meth) acrylate, ethyl (meth)acrylate, (n- or i-)propyl (meth)acrylate, (n-, i-, sec-, or t-)butyl (meth)acrylate, amyl (meth) acrylate, adamantyl (meth)acrylate, chloroethyl (meth) acrylate, 2-hydroxyethyl (meth)acrylate, 2-hydroxypropyl (meth)acrylate, 2-hydroxypentyl (meth)acrylate, cyclohexyl (meth)acrylate, allyl (meth)acrylate, trimethylolpropane mono(meth)acrylate, pentaerythritol mono(meth)acrylate, benzyl (meth)acrylate, methoxybenzyl (meth)acrylate, chlorobenzyl (meth) acrylate, hydroxybenzyl (meth) acrylate, hydroxyphenethyl (meth)acrylate, dihydroxyphenethyl (meth)acrylate, furfuryl (meth)acrylate, tetrahydrofurfuryl (meth)acrylate, phenyl (meth) acrylate, hydroxyphenyl (meth) acrylate, chlorophenyl (meth)acrylate, sulfamoylphenyl (meth)acrylate, 2-phenoxyethyl (meth)acrylate, 2-(hydroxyphenylcarbonyloxy)ethyl (meth)acrylate, phenol EO-modified (meth)acrylate, phenylphenol EO-modified (meth)acrylate, paracumylphenol EO-modified (meth)acrylate, nonylphenol EO-modified (meth)acrylate, N-acryloyloxyethylhexahydrophthalimide, bisphenol F EO-modified diacrylate, bisphenol A EO-modified diacrylate, dibromophenyl (meth) acrylate, tribromophenyl (meth) acrylate, dicyclopentenyloxyethyl (meth) acrylate, dicyclopentanyl acrylate, tricyclodecanedimethylol di(meth)acrylate, bisphenoxyethanolfluorene di(meth)acrylate, trimethylolpropane tri(meth)acrylate, pentaerythritol tri(meth)acrylate, pentaerythritol tetra(meth)acrylate, dipentaerythritol penta(meth)acrylate, and dipentaerythritol hexa(meth)acrylate. Here, "EO" means "ethylene oxide."

Examples of the (meth)acrylamides include (meth) acrylamide, N-methyl(meth)acrylamide, N-ethyl(meth)acrylamide, N-propyl(meth)acrylamide, N-butyl(meth)acrylamide, N-benzyl(meth)acrylamide, N-hydroxyethyl(meth)acrylamide, N-phenyl(meth)acrylamide, N-tolyl(meth)acrylamide, N-(hydroxyphenyl) (meth)acrylamide, N-(sulfamoylphenyl) (meth) acrylamide, N-(phenylsulfonyl) (meth) acrylamide, N-(tolylsulfonyl) (meth) acrylamide, N,N-dimethyl(meth) acrylamide, N-methyl-N-phenyl(meth)acrylamide, and N-hydroxyethyl-N-methyl(meth)acrylamide.

Examples of the vinyl esters include vinyl acetate, vinyl butyrate, vinyl benzoate, benzoic acid vinyl ester, vinyl t-butyl benzoate, vinyl chlorobenzoate, vinyl 4-ethoxybenzoate, vinyl 4-ethylbenzoate, vinyl 4-methylbenzoate, vinyl 3-methylbenzoate, vinyl 2-methylbenzoate, vinyl 4-phenylbenzoate, and vinyl pivalate.

Examples of the styrenes include styrene, p-acetylstyrene, p-benzoylstyrene, 2-butoxymethylstyrene, 4-butylstyrene, 4-sec-butylstyrene, 4-tert-butylstyrene, 2-chlorostyrene, 3-chlorostyrene, 4-chlorostyrene, dichlorostyrene, 2,4-diisopropylstyrene, dimethylstyrene, p-ethoxystyrene, 2-ethylstyrene, 2-methoxystyrene, 4-methoxystyrene, 2-methylstyrene, 3-methylstyrene, 4-methylstyrene, p-methylstyrene, p-phenoxystyrene, p-phenylstyrene, and divinylbenzene.

Any one of these radically polymerizable monomers may be used alone, or any combination of two or more of them may be used at any ratio.

Any of the above-exemplified cationically polymerizable monomers, anionically polymerizable monomers, and radically polymerizable monomers may be used, or two or more of them may be used in combination.

For a holographic recording medium, it is preferable to use a radically polymerizable monomer as the additional polymerizable compound used in combination with the compound of the invention represented by formula (1) because a reaction for forming a resin matrix is unlikely to be inhibited.

2-3 Additional Additive Component

An additional component may be added to the polymerizable composition of the invention so long as the effects of the invention are not impaired.

Examples of the additional component include various additives such as a solvent, an antioxidant, a plasticizer, an ultraviolet absorber, a sensitizer, a chain transfer agent, an antifoaming agent, a polymerization inhibitor, any filler formed of an organic or inorganic material, a dispersing agent, a pigment, and a wavelength conversion material such as a phosphor.

The polymerizable composition of the invention may contain a solvent for the purpose of controlling the viscosity.

The solvent is selected according to the physical properties of the polymerizable composition, and specific examples of the solvent include organic solvents such as: alcohols such as ethanol, propanol, isopropanol, ethylene glycol, and propylene glycol; aliphatic hydrocarbons such as hexane, pentane, and heptane; alicyclic hydrocarbon such as cyclopentane and cyclohexane; aromatic hydrocarbons such as toluene and xylene; halogenated hydrocarbons such as methylene chloride and chloroform; chain ethers such as dimethyl ether and diethyl ether; cyclic ethers such as dioxane and tetrahydrofuran; esters such as methyl acetate, ethyl acetate, butyl acetate, ethyl lactate, and ethyl butyrate; ketones such as acetone, ethyl methyl ketone, methyl isobutyl ketone, and cyclohexanone; cellosolves such as methyl cellosolve, ethyl cellosolve, and butyl cellosolve; carbitols such as methyl carbitol, ethyl carbitol, and butyl carbitol; propylene glycol monoalkyl ethers such as propylene glycol monomethyl ether, propylene glycol monoethyl ether, and propylene glycol mono-n-butyl ether; glycol ether esters such as ethylene glycol monomethyl ether acetate and propylene glycol monomethyl ether acetate; N,N-dimethylformamide; N,N-dimethylacetamide); sulfoxides (amides such as dimethyl sulfoxide; nitriles such as acetonitrile and benzonitrile; and N-methylpyrrolidone.

Any of these solvents may be used alone, or a solvent mixture thereof may be used. Water may be used for some polymerization methods (such as emulsion polymerization and suspension polymerization).

No particular limitation is imposed on the amount of the solvent (or a dispersion medium) used. The solvent may be used such that the polymerizable composition has a viscosity suitable for the polymerization method, a processing method, or its intended application.

In the present invention, it is preferable that an antioxidant used as an additive is added to the polymerizable composition in order for the polymer to be obtained to have good resistance to thermal yellowing.

Specific examples of the antioxidant include: phenol-based antioxidants such as 2,6-di-t-butylphenol, 2,6-di-t-butyl-p-cresol, n-octadecyl-3-(3',5'-di-t-butyl-4'-hydroxyphenyl)propionate, tetrakis-[methylene-3-(3',5'-di-t-butyl-4'-hydroxyphenyl)propionate]methane, triethylene glycol bis[3-(3-t-butyl-5-methyl-4-hydroxyphenyl)propionate], and 1,6-hexanediol bis[3-(3,5-di-t-butyl-4-hydroxyphenyl) propionate]; and phosphorus-based antioxidants such as triphenyl phosphite, trisisodecyl phosphite, tristridecyl phosphite, and tris(2,4-di-t-butylphenyl)phosphite. One of these may be used alone, or a combination of two or more may be used.

Preferably, the antioxidant used is a combination of a phenol-based antioxidant and a phosphorus-based antioxidant. Preferred examples of the combination of the phenol-based antioxidant and the phosphorus-based antioxidant include a combination of tris(2,4-di-t-butylphenyl) phosphite used as the phosphorus-based antioxidant and at least one phenol-based antioxidant selected from tetrakis-[methylene-3-(3',5'-di-t-butyl-4'-hydroxyphenyl)propionate] methane and n-octadecyl-3-(3',5'-di-t-butyl-4'-hydroxyphenyl)propionate.

From the viewpoint of allowing the polymer to be obtained to have good resistance to thermal yellowing, the amount of the antioxidant added to the polymerizable composition of the invention is preferably 0.01 to 5 parts by mass, more preferably 0.05 to 3 parts by mass, and still more preferably 0.1 to 2 parts by mass based on 100 parts by mass of the total amount of the polymerizable composition.

2-4 Method for Producing Polymerizable Composition

The polymerizable composition of the invention may be produced by mixing the components or may be produced by mixing components other than the polymerization initiator in advance and adding the polymerization initiator immediately before the polymerization reaction.

3. Method for Polymerizing Polymerizable Composition of Invention

No particular limitation is imposed on the method for polymerizing the polymerizable composition of the invention. Examples of the method include a polymerization method using active energy ray irradiation and a thermal polymerization method.

3-1. Polymerization Initiation Method (Active Energy Rays)

When the polymerizable composition of the invention is subjected to photo radical polymerization, the polymerizable composition is irradiated with active energy rays.

Preferably, the active energy rays used are an electron beam or light in the ultraviolet to infrared wavelength range. An extra-high pressure mercury light source or a metal halide light source can be used when the active energy rays are ultraviolet rays, and a metal halide light source or a halogen light source can be used when the active energy rays are visible light. A halogen light source can be used when the active energy rays are infrared light. In addition, light sources such as lasers and LEDs can also be used.

The dose of the active energy rays is appropriately set according to the type of light source, the thickness of a coating, etc. and is appropriately set such that the total reaction rate of the polymerizable groups in the compound of the invention represented by formula (1) and other polymerizable compounds is preferably 80% or more and more preferably 90% or more. The reaction rate is computed from changes in the intensities of the absorption peaks attributed to the polymerizable groups in an infrared absorption spectrum before and after the reaction.

After the polymerization under irradiation with the active energy rays, heat treatment or annealing treatment may be optionally performed to allow the polymerization to further proceed. The heating temperature in this case is preferably in the range of 80 to 200° C. The heating time is preferably in the range of 10 to 60 minutes.

3-2. Polymerization Initiation Method (Heating)

When the polymerizable composition of the invention is subjected to heat treatment for polymerization, the heating temperature is preferably in the range of 80 to 200° C. and more preferably in the range of 100 to 150° C. If the heating temperature is lower than 80° C., it is necessary to increase the heating time, and cost efficiency tends to decrease. If the heating temperature is higher than 200° C., the cost of energy is high, and the heating time and cooling time are long, so that cost efficiency tends to decrease.

4. Polymer

The polymer of the invention produced by polymerizing the polymerizable composition of the invention will be described.

4-1. Refractive Index

Generally, the polymerization reaction causes the overall density to increase. Therefore, the refractive index of the polymer tends to be higher than the refractive index of the unpolymerized compound that is a precursor of the polymer (which is referred to as a monomer). When a monomer having a high refractive index is used and its polymerization reaction is allowed to proceed sufficiently, the polymer obtained can have a high refractive index. It is therefore thought to be important to increase the refractive index of the polymer by appropriately designing the molecular structure of the monomer.

The value of the refractive index is high when it is evaluated using irradiation light with a short wavelength. A sample that exhibits a relatively high refractive index at a short wavelength also exhibits a relatively large refractive index at a high wavelength, and this relation is not reversed. Therefore, by evaluating the refractive indexes of materials at a certain wavelength for comparison, the magnitudes of the intrinsic refractive indexes of the materials can be compared. In the present invention, the value at an irradiation wavelength of 587 nm is used as a reference.

The refractive index of the polymer of the invention is preferably 1.55 or more, more preferably 1.60 or more, particularly preferably 1.63 or more, and most preferably 1.65 or more. No particular limitation is imposed on the upper limit of the refractive index of the polymer of the invention, but the refractive index is generally 2.0 or less.

The polymer of the invention can be used as an optical material for lenses etc. In this case, if the refractive index of the polymer is lower than 1.55, central portions of the lenses etc. are thick. This is not preferred because the lightweight of the plastic, which is one of its features, is not utilized. To develop precision optical members such as lenses, it is also important to use a combination of optical materials having a plurality of refractive indexes to thereby obtain optical characteristics suitable for the members. From this point of view, it can be said that a polymer having a refractive index of 1.63 or higher is a material particularly useful for optical components.

When the polymer of the invention is used as a recording layer material of a holographic recording medium, the refractive of the polymer of the invention is generally in the range of from 1.68 to 1.78 inclusive and preferably 1.77 or less. If the refractive index is less than 1.68, the diffraction efficiency is low, and multiplicity is insufficient. If the refractive index is larger than 1.78, the difference in the refractive index between the polymer and the matrix resin is excessively large. In this case, strong scattering occurs, and therefore transmittance decreases, so that larger energy is required for recording and reproduction.

4-2. Glass Transition Temperature

The glass transition temperature of the polymer of the invention is preferably 90° C. or higher, more preferably 100° C. or higher, still more preferably 110° C. or higher, and particularly preferably 120° C. or higher and is preferably 250° C. or lower, more preferably 220° C. or lower, and still more preferably 200° C. or lower. If the glass transition temperature is below the above range, the optical properties may deviate from the design values in the use environment, and the heat resistance may not satisfy that required for practical use. If the glass transition temperature is above the above range, the processability of the polymer is low. In this case, a molded product having good appearance and high dimensional accuracy may not be obtained, and the polymer becomes brittle. Therefore, the mechanical strength decreases, and the handleability of the molded product may deteriorate.

5. Optical Material and Optical Component

The compound of the invention, the polymerizable composition of the invention, and the polymer of the invention have properties such as a high refractive index, easy processability, and a low shrinkage factor and can therefore be applied to various optical materials and optical components.

Examples of the optical material include overcoats for optical use, hard coat agents, adhesives for optical members, resins for optical fibers, and acrylic-based resin reformers.

Examples of the optical component include lenses, filters, diffraction gratings, prisms, optical guides, glass covers for display devices, photosensors, photoswitches, LEDs, light-emitting elements, optical waveguides, optical splitters, optical fiber adhesives, substrates for display elements, substrates for color filters, substrates for touch panels, polarizing plates, display backlights, light guide plates, antireflective films, viewing angle widening films, optical recording, optical fabrication, and optical relief printing.

Moreover, the polymer of the invention can be used for a layer in any of the above components. Examples of such a layer include a display protective films.

In particular, the polymer of the invention is preferably applicable to plastic lenses because of the high-refractive index characteristics of the polymer. Examples of the lenses include imaging lenses of cameras (vehicle-mounted cameras, digital cameras, PC cameras, mobile phone camaras, monitoring cameras, etc.), eyeglass lenses, light beam condensing lenses, and beam diverging lenses.

A lens formed using the polymer of the invention may be optionally subjected to physical or chemical treatment such as surface polishing, antistatic treatment, hard coating treatment, antireflective coating treatment, or staining treatment for the purpose of preventing reflection, imparting high hardness, improving wear resistance, imparting chemical resistance, imparting anti-fogging properties, imparting fashionability, etc.

6. Holographic Recording Medium

The polymerizable composition of the invention can be preferably used for a recording layer of a holographic recording medium. In this case, the polymerizable composition of the invention is preferably a photoreactive composition containing, in addition to the compound of the invention, a matrix resin, a photopolymerization initiator, and a radical scavenger. The details of these materials when they are used as materials for a holographic recording medium will be described.

6-1. Matrix Resin

Preferably, the polymerizable composition of the invention contains a matrix resin. In particular, the matrix resin forming a recording layer of a holographic recording medium is an organic material that is not largely modified chemically and physically under irradiation with light and is formed mainly of a polymer of an organic compound.

The matrix resin, together with the above-described polymerizable compound, a photopolymerization initiator described later, etc., forms the polymerizable composition of the invention and is therefore strongly required to have good compatibility with the polymerizable compound, the photopolymerization initiator, etc. If the compatibility between the matrix resin and the other components is low, interfaces are formed between the materials, and reflection and refraction of light occurs at the interfaces. This causes leakage of light to unintended portions. Therefore, the interference fringes are distorted or broken, and recording may be performed in unwanted portions, so that deterioration in information may occur. The compatibility between the matrix resin and the other components can be evaluated based on, for example, light scattering intensity obtained by a detector disposed in a direction different from the direction of light passing through a sample, as described in, for example, Japanese Patent No. 3737306.

The matrix resin in the polymerizable composition of the invention may be a resin that includes a plurality of materials soluble in a solvent in the polymerizable composition and is to be three-dimensionally crosslinked after shaped into a usable form. Examples of such a resin include thermoplastic resins, thermosetting resins, and photocurable resins described below.

A three-dimensionally crosslinked resin is insoluble in a solvent and is a reaction cured product of a polymerizable compound that is liquid at room temperature and a compound having reaction activity with the polymerizable compound. The three-dimensionally crosslinked resin serves as physical obstacles and therefore reduces a volume change during recording. Specifically, in the recording layer after recording, bright portions are expanded, and dark portions are shrunk, so that irregularities tend to be formed on the surface of the holographic recording medium. To reduce the volume change, it is more preferable that a polymerizable composition containing a three-dimensionally crosslinked resin matrix is used for the recording layer.

In particular, from the viewpoint of adhesion to a support, the matrix resin is preferably a thermosetting resin. Resin materials that can be used as the matrix resin will be described in detail.

6-1-1. Thermoplastic Resin

Specific examples of the thermoplastic resin material include chlorinated polyethylene, polymethyl methacrylate resins (PMMA), copolymers of methyl methacrylate with other alkyl acrylates, copolymers of vinyl chloride with acrylonitrile, polyvinyl acetate resins (PVAC), polyvinyl alcohol, polyvinyl formal, polyvinylpyrrolidone, cellulose resins such as ethylcellulose and nitrocellulose, polystyrene resins, and polycarbonate resins. One of these resins may be used alone, or a mixture of two or more may be used.

No particular limitation is imposed on the solvent for these thermoplastic resins so long as it can dissolve these resins. Examples of such a solvent include: ketones such as acetone and methyl ethyl ketone; esters such as butyl acetate and propylene glycol methyl ether acetate; aromatic hydrocarbons such as toluene and xylene; ethers such as tetrahydrofuran and 1,2-dimethoxyethane; and amides such as N,N-dimethylacetamide and N-methylpyrrolidone. Only one of these solvents may be used alone, or a combination of two or more may be used.

6-1-2. Thermosetting Resin

When the matrix resin used is a thermosetting resin, its curing temperature varies largely depending on the type of crosslinking agent and the type of catalyst.

Representative examples of the combination of functional groups that allows the matrix resin to cure at room temperature include a combination of an epoxy and an amine, a combination of an epoxy and a thiol, and a combination of an isocyanate and an amine. Representative example of the combination when a catalyst is used include a combination of an epoxy and a phenol, a combination of an epoxy and an acid anhydride, and a combination of an isocyanurate and a polyol.

The former is simple because the reaction starts immediately after mixing. However, when the matrix resin is formed into, for example, a holographic recording medium, the matrix resin is cured while shaped into the holographic recording medium, and it is difficult to control the shape because there is only a limited time available for the formation of the holographic recording medium. In the latter case, the curing temperature and the curing time can be freely selected by appropriately selecting the type of catalyst and the amount of the catalyst used, and this is suitable for the case in which the thermosetting resin is cured while shaped into, for example, a holographic recording medium. Various resin raw materials including low molecular weight to large molecular weight materials are commercially available. Therefore, a suitable raw material can be selected such that the compatibility with a polymerizable reactive compound and a photo initiator and the adhesion to a substrate are maintained.

Each of the raw materials will next be described. For each raw material, one type may be used alone, or two or more types may be used in combination.

<Epoxy>

Examples of the epoxy include: polyglycidyl ether compounds of polyols such as (poly)ethylene glycol, (poly)propylene glycol, (poly)tetramethylene glycol, trimethylolpropane, and glycerin; alicyclic epoxy compounds having a 4 to 7-membered cyclic aliphatic group such as 3,4-epoxycyclohexylmethyl-3,4-epoxycyclohexanecarboxylate and 3,4-epoxy-1-methylcyclohexyl-3,4-epoxy-1-methylhexanecarboxylate; bisphenol A-type epoxy compounds; hydrogenated bisphenol A-type epoxy compounds; bisphenol F-type epoxy compounds; and phenol and cresol novolac-type epoxy compounds.

Preferably, the epoxy has two or more epoxy groups per molecule, but no particular limitation is imposed on the type of epoxy. If the number of epoxy groups is small, hardness necessary for the matrix may not be obtained. No particular limitation is imposed on the upper limit of the number of epoxy groups per molecule. The number of epoxy groups is generally 8 or less and preferably 4 or less. If the number of epoxy groups is excessively large, it takes a long time to consume the epoxy groups, and an excessively long time is necessary to form the matrix resin.

<Amine>

The amin used may contain a primary amino group or a secondary amino group. Examples of such an amine include: aliphatic polyamines such as ethylenediamine and diethylenetriamine and derivatives thereof; alicyclic polyamines such as isophoronediamine, menthanediamine, and N-aminoethylpiperazine and derivatives thereof; aromatic polyamines such as m-xylylenediamine and diaminodiphenylmethane and derivatives thereof; polyamides such as a condensation product of a dicarboxylic acid such as dimer acid and any of the above polyamines; imidazole compounds such as 2-methylimidazole and derivatives thereof; dicyandiamide; and adipic acid dihydrazide.

<Thiol>

Examples of the thiol include: dithiols such as 1,3-butanedithiol, 1,4-butanedithiol, 2,3-butanedithiol, 1,2-benzenedithiol, 1,3-benzenedithiol, 1,4-benzenedithiol, 1,10-decanedithiol, 1,2-ethanedithiol, 1,6-hexanedithiol, and 1,9-nonanedithiol; and thiol compounds including polythiols etc. such as THIOKOL (manufactured by Toray Fine Chemicals Co., Ltd.) and jERCURE QX40 (manufactured by Mitsubishi Chemical Corporation). Of these, commercial fast curable polythiols such as jERCURE QX40 are used preferably.

<Phenol>

Examples of the phenol include phenolic resins such as bisphenol A and novolac type phenolic resins and resol type phenolic resins.

<Acid Anhydride>

Examples of the acid anhydride include: monofunctional acid anhydrides such as phthalic anhydride and tetrahydrophthalic anhydride and derivatives thereof; and bifunctional acid anhydrides such as pyromellitic anhydride and benzophenonetetracarboxylic anhydride and derivatives thereof.

<Amounts of Amine, Thiol, Phenol, and Acid Anhydride Used>

The ratios of the amounts of the amine, thiol, phenol, and acid anhydride used to the number of moles of the epoxy groups are generally 0.1 equivalents or more and preferably 0.7 equivalents or more and is generally 2.0 equivalents or less and preferably 1.5 equivalents or less. If the amounts of the amine, thiol, phenol, and acid anhydride used are excessively small or are excessively large, the number of unreacted functional groups is large, and the storage stability may be impaired.

<Polymerization Initiator for Thermosetting Resin>

An anionic polymerization initiator or a cationic polymerization initiator selected according to the curing temperature and the curing time may be used as a catalyst for curing the thermosetting resin.

The anionic polymerization initiator generates anions under the application of heat or irradiation with light, and examples thereof include amines. Examples of the amines include: amino group-containing compounds such as dimethylbenzylamine, dimethylaminomethylphenol, and 1,8-diazabicyclo[5.4.0]undecene-7 and derivatives thereof; and imidazole compounds such as imidazole, 2-methylimidazole, and 2-ethyl-4-methylimidazole and derivatives thereof. One or a plurality of them may be used according to the curing temperature and the curing time.

The cationic polymerization initiator generates cations under the application of heat or irradiation with light, and examples thereof include aromatic onium salts. Specific examples include compounds containing an anionic component such as $SbF_6$—, $BF_4$—, $AsF_6$—, $PF_6$—, $CF_3SO_3$—, or $B(C_6F_5)_4$— and an aromatic cationic component containing an iodine atom, a sulfur atom, a nitrogen atom, a phosphorus atom, etc. In particular, diaryliodonium salts, triarylsulfonium salts, etc. are preferred. One or a plurality of them may be used according to the curing temperature and the curing time.

The amount used of the polymerization initiator for the thermosetting resin relative to the amount of the matrix resin is generally 0.001% mass or more and preferably 0.01% mass or more and is generally 50% by mass or less and preferably 10% by mass or less. If the amount used of the polymerization initiator for the thermosetting resin is excessively small, the concentration of the polymerization initiator for the thermosetting resin is excessively small, so that the polymerization may take an excessively long time. If the amount used of the polymerization initiator for the thermosetting resin is excessively large, a continuous ring-opening reaction, which is a polymerization reaction, may not occur.

<Isocyanate>

Preferably, the isocyanate includes two or more isocyanate groups per molecule, and no particular limitation is imposed on the type of isocyanate. If the number of isocyanate groups per molecule is small, hardness necessary for the matrix resin may not be obtained. No particular limitation is imposed on the upper limit of the number of isocyanate groups per molecule, but the number of isocyanate groups is generally 8 or less and preferably 4 or less. If the number of isocyanate groups per molecule is excessively large, it takes a long time to consume the isocyanate groups, and an excessively long time may be necessary to form the matrix resin. No particular limitation is imposed on the upper limit of the number of isocyanate groups per molecule, but the number of isocyanate groups is generally about 20 or less.

Examples of the isocyanate include: aliphatic isocyanates such as hexamethylene diisocyanate, lysine methyl ester diisocyanate, and 2,4,4-trimethylhexamethylene diisocyanate; alicyclic isocyanates such as isophorone diisocyanate and 4,4'-methylenebis(cyclohexyl isocyanate); aromatic isocyanates such as tolylene diisocyanate, 4,4'-diphenylmethane diisocyanate, xylylene diisocyanate, and naphthalene-1, 5'-diisocyanate; and multimers thereof. In particular, trimers to heptamers thereof are preferred.

Other examples include: reaction products of any of the above isocyanates with water and polyhydric alcohols such as trimethylolethane and trimethylolpropane; and multimers of hexamethylene diisocyanate and derivatives thereof.

As for the molecular weight of the isocyanate, its number average molecular weight is preferably from 100 to 50000 inclusive, more preferably from 150 to 10000 inclusive, and still more preferably from 150 to 5000 inclusive. If the number average molecular weight is excessively small, the crosslinking density increases. In this case, the hardness of the matrix resin is excessively high, and the recording speed may decrease. If the number average molecular weight is excessively large, the compatibility with other components decreases, and the crosslinking density decreases. In this case, the hardness of the matrix resin is excessively low, and recorded contents may be lost.

<Polyol>

Examples of the polyol include polypropylene polyols, polycaprolactone polyols, polyester polyols, and polycarbonate polyols.

(Polypropylene Polyol)

The polypropylene polyol is obtained by a reaction of propylene oxide with a diol or a polyhydric alcohol. Examples of the diol and the polyhydric alcohol include ethylene glycol, propylene glycol, 1,4-butanediol, 1,5-pentanediol, 3-methyl-1,5-pentanediol, 1,6-hexanediol, neopentyl glycol, diethylene glycol, 1,4-cyclohexanediol, 1,4-cyclohexanedimethanol, decamethylene glycol, polyethylene glycol, and polytetramethylene glycol. Commercial examples of the polypropylene polyol include: SANNIX GP-400 and GP-1000 (product names, products of Sanyo Chemical Industries, Ltd.); and ADEKA POLYETHER G400, G700, and G1500 (product names, products of ADEKA CORPORATION).

(Polycaprolactone Polyol)

The polycaprolactone polyol is obtained by a reaction of a lactone with a diol or a polyhydric alcohol. Examples of the lactone include α-caprolactone, β-caprolactone, γ-caprolactone, ε-caprolactone, α-methyl-ε-caprolactone, and β-methyl-ε-caprolactone.

Examples of the diol and the polyhydric alcohol include ethylene glycol, propylene glycol, 1,4-butanediol, 1,5-pentanediol, 3-methyl-1,5-pentanediol, 1,6-hexanediol, neopentyl glycol, diethylene glycol, 1,4-cyclohexanediol, 1,4-cyclohexanedimethanol, decamethylene glycol, polyethylene glycol, and polytetramethylene glycol.

Commercial examples of the polycaprolactone polyol obtained by a reaction of ε-caprolactone include PLACCEL 205, PLACCEL 205U, PLACCEL 205UT, PLACCEL 210, PLACCEL 220, PLACCEL 230, PLACCEL 240, PLACCEL 303, PLACCEL 305, PLACCEL 308, PLACCEL 312, PLACCEL 320, PLACCEL 401, PLACCEL L205AL, PLACCEL L212AL, PLACCEL L220AL, PLACCEL L320AL, PLACCEL T2103, PLACCEL T2205, and PLACCEL P3403 (product names, products of Daicel Corporation).

(Polyester Polyol)

The polyester polyol is obtained, for example, by polycondensation of a dicarboxylic acid or an anhydride thereof with a polyol.

Examples of the dicarboxylic acid include succinic acid, adipic acid, sebacic acid, azelaic acid, dimer acid, maleic anhydride, isophthalic acid, terephthalic acid, and trimellitic acid.

Examples of the polyol include ethylene glycol, propylene glycol, 1,4-butanediol, 1,5-pentanediol, 3-methyl-1,5-pentanediol, 1,6-hexanediol, neopentyl glycol, diethylene glycol, 1,4-cyclohexanediol, 1,4-cyclohexanedimethanol, decamethylene glycol, polyethylene glycol, and polytetramethylene glycol.

Examples of the polyester polyol include polyethylene adipate, polybutylene adipate, and polyhexamethylene adipate. Commercial examples of the polyester polyol include: ADEKA NEWACE F series, ADEKA NEWACE Y series, and ADEKA NEWACE NS series (product names, products of ADEKA CORPORATION); and Kuraray Polyol N-2010, β-4011, and β-1020 (produce names, products of KURARAY Co., Ltd.).

(Polycarbonate Polyol)

Examples of the polycarbonate polyol include; polyols obtained by a dealcoholization condensation reaction of glycols with dialkyl carbonates (such as dimethyl carbonate and diethyl carbonate); polyols obtained by a dephenolization condensation reaction of glycols with diphenyl carbonates; and polyols obtained by a deglycolization condensation reaction of glycols with carbonates (such as ethylene carbonate and diethyl carbonate).

Examples of the glycols include: aliphatic diols such as 1,6-hexanediol, diethylene glycol, propylene glycol, 1,4-butanediol, 3-methyl-1,5 pentanediol, and neopentyl glycol; and alicyclic diols such as 1,4-cyclohexanediol and 1,4-cyclohexanedimethanol.

Examples of the polycarbonate polyol include: poly(hexamethylene carbonate)polyol obtained by a condensation reaction of 1,6-hexanediol with diethyl carbonate; poly (pentylene carbonate) obtained by a condensation reaction of pentanediol with diethyl carbonate; and poly(butylene carbonate) obtained by a condensation reaction of 1,4-butanediol with diethyl carbonate.

Commercial examples of the polycarbonate polyol include: PLACCEL CD CD205, PLACCEL CD CD210, and PLACCEL CD CD220 (product names, products of Daicel Corporation); and DURANOL T5651, DURANOL T5652, and DURANOL T5650J (product names, products of Asahi Kasei Corporation).

(Molecular Weight of Polyol)

As for the molecular weight of the polyol described above, its number average molecular weight is preferably from 100 to 50000 inclusive, more preferably from 150 to 10000 inclusive, and still more preferably from 150 to 5000 inclusive. If the number average molecular weight is excessively small, the crosslinking density increases. In this case, the hardness of the matrix resin is excessively high, and the recording speed may decrease. If the number average molecular weight is excessively large, the compatibility with other components decreases, and the crosslinking density decreases. In this case, the hardness of the matrix resin is excessively low, and recorded contents may be lost.

<Additional Components>

The matrix resin in the present embodiment may contain, in addition to the components described above, additional components so long as the gist of the invention is retained.

Examples of the additional components include compounds having a hydroxyl group such as ethylene glycol, propylene glycol, 1,4-butanediol, 1,5-pentanediol, 3-methyl-1,5-pentanediol, 1,6-hexanediol, neopentyl glycol, diethylene glycol, 1,4-cyclohexanediol, 1,4-cyclohexanedimethanol, decamethylene glycol, trimethylolpropane, polyethylene glycol, and polytetramethylene glycol. These compounds are used for the purpose of changing the physical properties of the matrix resin.

<Urethane Polymerization Catalyst>

To facilitate the reaction of the isocyanate with the polyol, an appropriate urethane polymerization catalyst may be contained.

Examples of the urethane polymerization catalyst include: onium salts such as bis(4-t-butylphenyl)iodonium perfluoro-1-butanesulfonate, bis(4-t-butylphenyl)iodonium p-toluenesulfonate, bis(4-t-butylphenyl)iodonium trifluoromethanesulfonate, (4-bromophenyl)diphenylsulfonium triflate, (4-t-butylphenyl)diphenylsulfonium trifluoromethanesulfonate, diphenyliodonium perfluoro-1-butanesulfonate, (4-fluorophenyl)diphenylsulfonium trifluoromethanesulfonate, diphenyl-4-methylphenylsulfonium trifluoromethanesulfonate, triphenylsulfonium trifluoromethanesulfonate, and bis(alkylphenyl)iodonium hexafluorophosphonate; catalysts prepared using Lewis acids as main components such as zinc chloride, tin chloride, iron chloride, aluminum chloride, and $BF_3$; proton acids such as hydrochloric acid and phosphoric acid; amines such as trimethylamine, triethylamine, triethylenediamine, dimethylbenzylamine, and diazabicycloundecene; imidazoles such as 2-methylimidazole, 2-ethyl-4-methylimidazole, and 1-cyanoethyl-2-undecylimidazolinium trimellitate; bases such as sodium hydroxide, potassium hydroxide, and potassium carbonate; tin catalysts such as dibutyltin laurate, dioctyltin laurate, and dibutyltin octoate; bismuth catalysts such as bismuth tris(2-ethylhexanoate) and tribenzoyloxy bismuth; and zirconium catalysts such as zirconium tetrakis(ethylacetoacetate), 1,1'-isopropylidenezirconocene dichloride, and zirconium tetrakis(2,4-pentanedionato).

Of these, bismuth catalysts and zirconium catalysts are preferred in order to improve storage stability.

No particular limitation is imposed on the bismuth-based catalyst so long as it is a catalyst containing elemental bismuth and is a compound that facilitates the reaction of the isocyanate with the polyol.

Examples of the bismuth-based catalyst include bismuth tris(2-ethylhexanoate), tribenzoyloxy bismuth, bismuth triacetate, bismuth tris(dimethyldithiocarbamate), bismuth hydroxide, triphenylbismuth(V) bis(trichloroacetate), tris(4-methylphenyl)oxobismuth(V), and triphenylbis(3-chlorobenzoyloxy)bismuth(V).

In particular, a trivalent bismuth compound is preferred in terms of catalytic activity, and bismuth carboxylate, i.e., a compound represented by general formula $Bi(OCOR)_3$ ((R is a linear or branched alkyl group, a cycloalkyl group, or a substituted or unsubstituted aromatic group), is more preferred. Any one of these bismuth-based catalysts may be used alone, or any combination of two or more of them may be used at any ratio.

No particular limitation is imposed on the zirconium-based catalyst so long as it is a catalyst containing elemental zirconium and is a compound that facilitates the reaction of the isocyanate with the polyol.

Examples of the zirconium-based catalyst include cyclopentadienylzirconium trichloride, decamethylzirconocene dichloride, 1,1'-dibutylzirconocene dichloride, 1,1'-isopropylidenezirconocene dichloride, tetrakis(2,4-pentanedionato) zirconium, tetrakis(trifluoro-2,4-pentanedionato) zirconium, tetrakis(hexafluoro-2,4-pentanedionato) zirconium, zirconium butoxide, zirconium-t-butoxide, zirconium propoxide, zirconium isopropoxide, zirconium ethoxide, bis (ethylacetoacetate)dibutoxy zirconium, tetrakis(ethylacetoacetate)zirconium, zirconium oxide, barium zirconium oxide, calcium zirconium oxide, zirconium bromide, zirconium chloride, zirconium fluoride, (indenyl)zirconium dichloride, and zirconium carbonate.

In particular, compounds having an organic ligand are preferred in terms of compatibility with other components, and compounds having an alkoxide structure or an acetylacetonate (2,4-pentanedionato) structure are more preferred. Any one of the above zirconium compounds may be used alone, or any combination of two or more of them may be used at any ratio.

One of the bismuth-based catalysts and the zirconium-based catalysts may be used alone, or any mixture of them may be used.

The ratio of the amount of the urethane polymerization catalyst used to the amount of the matrix resin is generally 0.0001% mass or more and preferably 0.001% mass or more and is generally 10% by mass or less and preferably 5% by mass or less. If the amount of the urethane polymerization catalyst used is excessively small, an excessively long time may be necessary for curing. If the amount used is excessively large, it may be difficult to control the curing reaction.

The use of the urethane polymerization catalyst allows curing at room temperature. However, the curing may be performed at increased temperature. The temperature in this case is preferably between 40° C. to 90° C.

6-1-3. Photocurable Resin

When the matrix resin used is a photocurable resin, it is necessary to cure the matrix resin using a photo-initiator for the matrix resin suitable for the wavelength used. During curing of the matrix resin under irradiation with light, defective forming or poor bonding may occur. It is therefore desirable that the curing reaction is stable at around room temperature, which is main working temperature. In consideration of this, catalytic curing using the photo-initiator for the matrix resin is a desirable choice.

An active species, i.e., cations or anions, is generally generated from the photo-initiator for the matrix resin under irradiation with light. It is therefore preferable that a photocurable resin that is cured by such an active species is selected as the matrix resin.

Examples of the functional group reactive with cations such as protons include an epoxy group and an oxetanyl group. Specific examples of a compound having an epoxy group include: polyglycidyl ether compounds of polyols such as (poly)ethylene glycol, (poly)propylene glycol, (poly)tetramethylene glycol, trimethylolpropane, and glycerin; alicyclic epoxy compounds having a 4- to 7-membered cyclic aliphatic group such as 3,4-epoxycyclohexylmethyl-3,4-epoxycyclohexanecarboxylate and 3,4-epoxy-1-methylcyclohexyl-3,4-epoxy-1-methylhexanecarboxylate; bisphenol A-type epoxy compounds; hydrogenated bisphenol A-type epoxy compounds; bisphenol F-type epoxy compounds; and phenol and cresol novolac-type epoxy compounds. Examples of a compound having an oxetanyl group include; 2-ethyl-2-oxetanyl ether of bisphenol A; and 1,6-bis(2-ethyl-2-oxetanyloxy)hexane. (Note that the term "(poly)ethylene glycol," for example, means both "ethylene glycol" and "polyethylene glycol" which is a polymer of ethylene glycol.)

Examples of the functional group reactive with anions include an epoxy group and an episulfide group. Specific examples of a compound having an episulfide group include phenyl episulfide and diepisulfide methyl ether of bisphenol A.

The ratio of the amount of the photo-initiator for the matrix resin that is used to photo-cure the matrix resin to the amount of the polymerizable compound is generally 0.01% mass or more and preferably 0.1% mass or more and is generally 1% by mass or less and preferably 0.5% by mass or less. If the amount used of the photo-initiator for the matrix resin is excessively small, an excessively long time may be necessary for curing. If the amount used is excessively large, it may be difficult to control the curing reaction.

In particular, when the polymerizable composition is used as a holographic recording material, the polymerizable composition is irradiated with light also during recording. It is therefore important that the wavelength for curing be different from the wavelength for recording, and the difference in wavelength is at least 10 nm and preferably 30 nm. The selection of the photo-initiator for the matrix resin can be roughly estimated from the absorption wavelength of the initiator.

6-2. Photopolymerization Initiator

Any known photo radical polymerization initiator can be used as the photopolymerization initiator that assists the polymerization of the compound of the invention. Examples include azo-based compounds, azide-based compounds, organic peroxides, organic borates, onium salts, bisimidazole derivatives, titanocene compounds, iodonium salts, organic thiol compounds, halogenated hydrocarbon derivatives, acetophenones, benzophenones, hydroxybenzenes, thioxanthones, anthraquinones, ketals, acylphosphine oxides, sulfone compounds, carbamic acid derivatives, sulfonamides, triarylmethanols, and oxime esters. In particular, the photopolymerization initiator is preferably a titanocene compound, an acylphosphine oxide compound, an oxime ester compound, etc. because the polymerization reaction proceeds under light in the visible range.

6-2-1. Titanocene Compound

When a titanocene compound is used as the photopolymerization initiator, no particular limitation is imposed on the type of titanocene compound. For example, one selected from various titanocene compounds described in JP59-152396A, JP61-151197A, etc. can be appropriately used.

Specific examples of the titanocene compound include di-cyclopentadienyl-Ti-di-chloride, di-cyclopentadienyl-Ti-bis-phenyl, di-cyclopentadienyl-Ti-bis-2,3,4,5,6-pentafluorophen-1-yl, dicyclopentadienyl-Ti-bis-2,3,5,6-tetrafluorophen-1-yl, di-cyclopentadienyl-Ti-bis-2,4,6-trifluorophen-1-yl, di-cyclopentadienyl-Ti-bis-2,6-di-fluorophen-1-yl, di-cyclopentadienyl-Ti-bis-2,4-di-fluorophen-1-yl, di-methylcyclopentadienyl-Ti-bis-2,3,4,5,6-pentafluorophen-1-yl, di-methylcyclopentadienyl-Ti-bis-2,3,5,6-tetrafluorophen-1-yl, di-methylcyclopentadienyl-Ti-bis-2,6-difluorophen-1-yl, and di-cyclopentadienyl-Ti-bis-2,6-difluoro-3-(pyrr-1-yl)-phen-1-yl.

6-2-2. Acylphosphine Oxide Compound

Specific examples of the acylphosphine oxide compound include monofunctional initiators having only one photo-cleavage point per molecule and bifunctional initiators having two photo-cleavage points per molecule.

Examples of the monofunctional initiator include triphenylphosphine oxide, diphenyl(2,4,6-trimethylbenzoyl) phosphine oxide, and 2,6-dichlorobenzoyldiphenylphosphine oxide.

Examples of the bifunctional initiator include bis(2,4,6-trimethylbenzoyl)-phenylphosphine oxide, bis(2,6-dimethoxybenzoyl)-2,4,4-trimethylpentylphosphine oxide, bis(2,6dichlorobenzoyl)-4-propylphenylphosphine oxide, and bis(2,6dichlorobenzoyl)-2,5dimethylphenylphosphine oxide.

6-2-3. Oxime Ester-Based Compound

Specific examples of the oxime ester-based compound include 1-[4-(phenylthio)-2-(O-benzoyloxime)]-1,2-octanedione, 1-[9-ethyl-6-(2-methylbenzoyl)-9H-carbazol-3-yl]-1-(O-acetyloxime)ethanone, 4-(acetoxyimino)-5-[9-ethyl-6-(2-methylbenzoyl)-9H-carbazol-3-yl]-5-oxopentanoic acid methyl ester, 1-(9-ethyl-6-cyclohexanoyl-9H-carbazol-3-yl)-1-(O-acetyloxime)glutaric acid methyl ester, 1-(9-ethyl-9H-carbazol-3-yl)-1-(O-acetyloxime)glutaric acid methyl ester, and 1-(9-ethyl-9H-carbazol-3-yl)-1-(O-acetyloxime)-3-methyl-butanoic acid.

6-2-4. Amount of Photopolymerization Initiator Used

Any one of the above photopolymerization initiators may be used alone, or any combination of two or more of them may be used at any ratio.

As for the content of the photopolymerization initiator in the polymerizable composition of the invention, the molar amount of the photopolymerization initiator per unit weight of the polymerizable composition is preferably 0.5 μmol/g or more. The content is more preferably 1 μmol/g or more. As for the content of the photopolymerization initiator in the polymerizable composition of the invention, the molar amount per unit weight of the polymerizable composition is preferably 100 μmol/g or less. The content is more preferably 50 μmol/g or less.

If the content of the photopolymerization initiator is excessively small, the amount of radicals generated is small. In this case, the rate of photopolymerization decreases, and the recording sensitivity of a holographic recording medium may decrease. If the content of the photopolymerization initiator is excessively large, radicals generated by irradiation with light recombine with each other or disproportionate. In this case, the contribution of the radicals to photopolymerization is reduced, and again the recording sensitivity of a holographic recording medium may decrease. When two or more photopolymerization initiators are used in combination, it is preferable that the total amount of the photopolymerization initiators is set so as to fall within the above range.

6-3. Radical Scavenger

In holographic recording, to fix the intensity pattern of interference light accurately as a polymer distribution in a holographic recording medium, a radical scavenger may be added. Preferably, the radical scavenger has both a functional group that scavenges radicals and a reactive group to be fixed to the matrix resin through a covalent bond. Examples of the functional group that scavenges radicals include a stable nitroxyl radical group.

6-3-1. Type of Radical Scavenger

Examples of the reactive group to be fixed to the matrix resin through a covalent bond include a hydroxy group, an amino group, an isocyanate group, and a thiol group. Examples of such a radical scavenger include 4-hydroxy-2,2,6,6-tetramethylpiperidine-1-oxyl free radicals (TEMPOL), 3-hydroxy-9-azabicyclo[3.3.1]nonane N-oxyl, and 5-HO-AZADO: 5-hydroxy-2-azatricyclo[3.3.1.1$^{3,7}$]decane N-oxyl.

6-3-2. Content of Radical Scavenger

Any one of the above various radical scavengers may be used alone, or any combination of two or more of them may be used at any ratio.

As for the content of the radical scavenger in the polymerizable composition of the invention, the molar amount of the radical scavenger per unit weight of the polymerizable composition is preferably 0.5 μmol/g or more and more preferably 1 μmol/g or more. The content of the radical scavenger in the polymerizable composition of the invention is preferably 100 μmol/g or less and more preferably 50 μmol/g or less.

If the content of the radical scavenger is excessively small, the efficiency of scavenging radicals is low, and a polymer with a low degree of polymerization diffuses, so that the amount of components not contributing to signals tends to increase. If the content of the radical scavenger is excessively large, the efficiency of the polymerization of the polymer decreases, and signals tend not to be recorded. When two or more radical scavengers are used in combination, it is preferable that the total amount of the radical scavengers is set so as to fall within the above range.

6-4. Additional Components

The polymerizable composition of the invention may contain additional components in addition to the above components unless the invention departs from the scope thereof.

Examples of the additional components include components for preparing the polymerizable composition such as a solvent, a plasticizer, a dispersant, a leveling agent, an antifoaming agent, and an adhesion promoter. Examples of the additional components when the polymerizable composition is used for a holographic recording medium include components for controlling a recording reaction such as a chain transfer agent, a polymerization terminator, a compatibilizer, a reaction aid, and a sensitizer. Examples of other additives necessary for improving properties include a preservative, a stabilizer, an antioxidant, and an ultraviolet absorber. Any one of these components may be used alone, or any combination of two or more of them may be used at any ratio.

<Sensitizer>

A compound that controls excitation of the photopolymerization initiator may be added to the polymerizable composition of the invention. Examples of such a compound include a sensitizer and a sensitization aid.

The sensitizer used may be selected from various known sensitizers. Generally, a colored compound such as a coloring agent is often used as the sensitizer in order to absorb visible and ultraviolet laser beams. When the polymerizable composition is used for a holographic recording medium, a suitable sensitizer is selected according to the wavelength of a laser beam used for recording and the type of initiator used. Specific preferred examples of the sensitizer used for a system using a green laser include compounds described in JPH5-241338A, JPH2-69A, JPH2-55446B, etc. Examples of the sensitizer used for a system using a blue laser include compounds described in JP2000-10277A, JP2004-198446A, etc. Any one of these sensitizers may be used alone, or any combination of two or more of them may be used at any ratio.

When a holographic recording medium to be obtained is required to be colorless and transparent, it is preferable to use a cyanine-based coloring agent as the sensitizer. Generally, a cyanine-based coloring agent is easily decomposed by light. Therefore, when the holographic recording medium is subjected to postexposure, i.e., left to stand under exposure to indoor light or sunlight for several hours to several days, the cyanine-based coloring agent in the holographic recording medium is decomposed, and the holographic recording medium does not exhibit absorption in the visible range. The thus-obtained holographic recording medium is colorless and transparent.

It is necessary to increase or decrease the amount of the sensitizer according to the thickness of a recording layer to be formed, and the ratio of the amount of the sensitizer to the amount of the photopolymerization initiator described above in 6-2 is generally 0.01% mass or more and preferably 0.1% mass or more and is generally 10% by mass or less and preferably 5% by mass or less. If the amount of the sensitizer used is excessively small, the initiation efficiency is low, and recording may take a very large amount of time. If the amount of the sensitizer used is excessively large, absorption of light used for recording and reproduction increases, and the light may not easily penetrate deep into the recording layer. When two or more sensitizers are used in combination, the total amount of the sensitizers is set so as to fall within the above range.

<Plasticizer>

To improve the reaction efficiency and adjust the physical properties of the recording layer of a holographic recording medium, the polymerizable composition of the invention may contain a plasticizer.

Examples of the plasticizer include: phthalates such as dioctyl phthalate, diisononyl phthalate, diisodecyl phthalate, and diundecyl phthalate; adipates such as bis(2-ethylhexyl) adipate, diisononyl adipate, and di-n-butyl adipate; sebacates such as dioctyl sebacate and dibutyl sebacate; phosphates such as tricresyl phosphate; citrates such as acetyl tributyl citrate; trimellitates such as trioctyl trimellitate; epoxidized soybean oil; chlorinated paraffin; alkoxylated (poly)alkylene glycol esters such as acetoxymethoxypropane; and alkoxy-terminated polyalkylene glycols such as dimethoxypolyethylene glycol.

A plasticizer containing elemental fluorine and exemplified in Japanese Patent No. 6069294 may also be used. Examples of the plasticizer containing elemental fluorine include 2,2,2-trifluoroethyl butylcarbamate, bis(2,2,2-trifluoroethyl)-(2,2,4-trimethylhexane-1,6-diyl)biscarbamate, bis(2,2,2-trifluoroethyl)-[4-({[(2,2,2-trifluoroethoxy)carbonyl]amino}-methyl)octane-1,8-diyl]biscarbamate, 2,2,3,3,4,4,5,5,6,6,7,7,8,8,9,9-hexadecafluorononyl butylcarbamate, and 2,2,2-trifluoroethyl phenylcarbamate.

The ratio of the amount of the plasticizer to the total solid content of the polymerizable composition is generally from 0.01% mass to 50% by mass inclusive and preferably from 0.05% mass or to 20% by mass inclusive. If the content of the plasticizer is below the above range, the effects of improving the reaction efficiency and adjusting the physical properties are not obtained. If the content is above the above range, the transparency of the recording layer deteriorates, and bleeding of the plasticizer becomes significant.

<Leveling Agent>

A leveling agent may be used for the polymerizable composition of the invention. Examples of the leveling agent include sodium polycarboxylates, ammonium polycarboxylates, amine polycarboxylates, silicon-based leveling agents, acrylic-based leveling agents, ester compounds, ketone compounds, and fluorine compounds. Any one of them may be used alone, or any combination of two or more of them may be used at any ratio.

<Chain Transfer Agent>

A chain transfer agent may be used for the polymerizable composition of the invention. Examples of the chain transfer agent include: phosphinates such as sodium phosphite and sodium hypophosphite; mercaptans such as mercaptoacetic acid, mercaptopropionic acid, 2-propanethiol, 2-mercaptoethanol, and thiophenol; aldehydes such as acetaldehyde and propionaldehyde; ketones such as acetone and methyl ethyl ketone; halogenated hydrocarbons such as trichloroethylene and perchloroethylene; terpenes such as terpinolene, α-terpinene, β-terpinene, and γ-terpinene; non-conjugated dienes such as 1,4-cyclohexadiene, 1,4-cycloheptadiene, 1,4-cyclooctadiene, 1,4-heptadiene, 1,4-hexadiene, 2-methyl-1,4-pentadiene, 3,6-nonanedien-1-ol, and 9,12-octadecadienol; linolenic acids such as linolenic acid, γ-linolenic acid, methyl linoleate, ethyl linoleate, isopropyl linoleate, and linolenic anhydride; linoleic acids such as linoleic acid, methyl linoleate, ethyl linoleate, isopropyl linoleate, and linoleic anhydride; eicosapentaenoic acids such as eicosapentaenoic acid and ethyl eicosapentaenoate; and docosahexaenoic acids such as docosahexaenoic acid and ethyl docosahexaenoate.

The ratio of the amount of the additives used to the total amount of solids in the polymerizable composition in the present embodiment is generally 0.001% mass or more preferably 0.01% mass or more and is generally 30% by mass or less and preferably 10% by mass or less. When two or more additive are used in combination, the total amount of the additives is set so as to fall within the above range.

6-5. Compositional Ratio of Components in Polymerizable Composition

The contents of the components in the polymerizable composition of the invention can be freely set so long as they do not deviate from the scope of the invention. Preferably, the ratios of the components shown below in terms of their molar amounts per unit mass of the polymerizable composition fall within the following ranges.

The content of the polymerizable compounds including the compound of the invention is preferably 5 μmol/g or more, more preferably 10 μmol/g or more, and still more preferably 100 μmol/g or more. The content of the polymerizable compounds is preferably 2000 μmol/g or less, more preferably 1000 μmol/g or less, and still more preferably 500 μmol/g or less.

When the content of the polymerizable compounds is equal to or lower than the above lower limit, a holographic recording medium with sufficient diffraction efficiency is obtained. When the content is equal to or lower than the above upper limit, the compatibility with the resin matrix in the recording layer is maintained, and the degree of shrinkage of the recording layer due to recording tends to be small.

When the isocyanate and the polyol are used for the matrix resin in the polymerizable composition of the invention, the total content of the isocyanate and the polyol is generally 0.1% mass or more, preferably 10% mass or more, and still more preferably 35% mass or more and is generally 99.9% by mass or less and preferably 99% by mass or less. When the total content is equal to or more than the lower limit, the recording layer can be formed easily.

In this case, the ratio of the number of functional groups in the polyol that are reactive with the isocyanate to the number of isocyanate groups in the isocyanate is preferably 0.1 or more and more preferably 0.5 or more and is generally 10.0 or less and preferably 2.0 or less. When this ratio is within the above range, the number of unreacted functional groups is small, and the storage stability is improved.

In the polymerizable composition, it is preferable to determine the content of the urethane polymerization catalyst in consideration of the reaction rate of the isocyanate and the polyol, and the content is preferably 5% by mass or less, more preferably 4% by mass or less, and still more preferably 1% by mass or less. The amount of the urethane polymerization catalyst used is preferably 0.005% mass or more.

The total amount of additional components other than the above components may be 30% by mass or less and is preferably 15% by mass or less and more preferably 5% by mass.

6-6. Method for Producing Polymerizable Composition

In the present invention, no particular limitation is imposed on the method for producing the polymerizable composition containing the polymerizable compound, the matrix resin, and the photopolymerization initiator, and the order of mixing etc. can be appropriately adjusted. When the polymerizable composition contains a component other than the above components, any combination of these components may be mixed in any order.

The polymerizable composition when the isocyanate and the polyol are used for the matrix resin can be obtained, for example, by the following method, but the present invention is not limited thereto.

The polymerizable compound, the photopolymerization initiator, and components other than the isocyanate and the urethane polymerization catalyst are mixed together to prepare a photoreactive composition (solution A). A mixture of the isocyanate and the urethane polymerization catalyst is prepared as solution B.

Alternatively, the polymerizable compound, the photopolymerization initiator, and components other than the isocyanate may be mixed to prepare a photoreactive composition (solution A).

Preferably, each solution is subjected to dewatering and degassing. If the dewatering and degassing are insufficient, air bubbles are generated during the production of a holographic recording medium, and therefore a uniform recording layer may not be obtained. The dewatering and degassing may be performed by heating under reduced pressure so long as the components are not damaged.

Preferably, the polymerizable composition including a mixture of the solution A and solution B is produced immediately before molding of the holographic recording medium. In this case, a mixing technique using a conventional method may be used. When the solution A and the solution B are mixed, degassing may be optionally performed in order to remove residual gas. Preferably, the solution A and the solution B are subjected to a filtration process separately or simultaneously after mixing in order to remove foreign substances and impurities. It is more preferable to filter these solutions separately.

The isocyanate used for the matrix resin may be an isocyanate-functional prepolymer prepared by a reaction of an isocyanate having an excessive amount of isocyanate groups with the polyol. The polyol used for the matrix resin may be an isocyanate reactive prepolymer prepared by a reaction of a polyol containing an excessive amount of isocyanate reactive functional groups with the isocyanate.

6-7. Holographic Recording Medium of Invention

The holographic recording medium of the present invention that uses the polymerizable composition of the invention includes the recording layer and optionally includes a support and additional layers. Generally, the holographic recording medium includes the support, and the recording layer and the additional layers are stacked on the support to form the holographic recording medium. However, when the recording layer and the additional layers have the strength and durability required for the medium, the holographic recording medium may include no support. Examples of the additional layers include a protective layer, a reflecting layer, and an anti-reflection layer (anti-reflection film).

6-7-1. Recording Layer

The recording layer of the holographic recording medium of the invention is a layer formed from the polymerizable composition of the invention, and information is recorded in the recording layer. The information is generally recorded as a hologram. As described later in detail in a recording method section, the polymerizable compound (hereinafter referred to as a polymerizable monomer) contained in the recording layer partially undergoes a chemical change such as polymerization during holographic recording etc. Therefore, in the holographic recording medium after recording, part of the polymerizable monomer is consumed and present as a reacted compound such as a polymer.

No particular limitation is imposed on the thickness of the recording layer, and the thickness may be appropriately set in consideration of the recording method etc. The thickness is preferably 1 μm or more and more preferably 10 μm or more and is preferably 1 cm or less and more preferably 3 mm or less. When the thickness of the recording layer is equal to or more than the above lower limit, selectivity for holograms when multiple recording is performed on the holographic recording medium is high, and therefore the degree of multiple recording can tend to be increased. When the thickness of the recording layer is equal to or less than the above upper limit, the recording layer as a whole can be formed uniformly. Therefore, the holograms can have uniform diffraction efficiency, and multiple recording can tend to be performed with a high S/N ratio.

Preferably, the rate of shrinkage of the recording layer due to exposure to light during information recording or reproduction is 0.25% or less, from the viewpoint of recording reproducibility.

6-7-2. Support

No particular limitation is imposed on the details of the support so long as it has the strength and durability required for the holographic recording medium, and any support can be used.

No limitation is imposed on the shape of the support, and the support is generally formed into a flat plate or a film.

No limitation is imposed on the material forming the support, and the material may be transparent or may be opaque.

Examples of the transparent material for the support include: organic materials such as acrylic, polyethylene terephthalate, polyethylene naphthoate, polycarbonate, polyethylene, polypropylene, amorphous polyolefin, polystyrene, polycycloolefin, and cellulose acetate; and inorganic materials such as glass, silicon, and quartz. Of these, polycarbonate, acrylic, polyester, amorphous polyolefin, glass, etc. are preferred, and polycarbonate, acrylic, amorphous polyolefin, polycycloolefin, and glass are more preferred.

Examples of the opaque material for the support include: metals such as aluminum; and a coating prepared by coating the transparent support with a metal such as gold, silver, or aluminum or a dielectric such as magnesium fluoride or zirconium oxide.

No particular limitation is imposed on the thickness of the support. Preferably, the thickness is in the range of 0.05 mm or more and 1 mm or less. When the thickness of the support is equal to or more than the above lower limit, the mechanical strength of the holographic recording medium can be ensured, and warpage of the substrate can be prevented. When the thickness of the support is equal to or less than the above upper limit, advantages such as an increase in the transmission amount of light, a reduction in the weight of the holographic recording medium, and a rection in cost can be obtained.

The surface of the support may be subjected to surface treatment. The surface treatment is generally performed in order to improve the adhesion between the support and the recording layer. Examples of the surface treatment include corona discharge treatment performed on the support and the formation of an undercoat layer on the support in advance. Examples of the composition for the undercoat layer include halogenated phenols, partially hydrolyzed vinyl chloride-vinyl acetate copolymers, and polyurethane resins.

The surface treatment on the support may be performed for a purpose other than the improvement in adhesion. Examples of such surface treatment include: reflecting coating treatment in which a reflecting coating layer is formed using a metal material such as gold, silver, or aluminum; and dielectric coating treatment in which a dielectric layer formed of magnesium fluoride, zirconium oxide, etc. is formed. Such a layer may be formed as a single layer, or two or more layers may be formed.

The surface treatment may be performed for the purpose of controlling the gas and water permeability of the substrate. For example, when the support supporting the recording layer has the function of preventing permeation of gas and water, the reliability of the holographic recording medium can be improved.

The support may be disposed only on one of the upper and lower sides of the recording layer of the holographic recording medium of the present invention or may be disposed on both sides. When supports are disposed on both the upper and lower sides of the recording layer, at least one of the supports is made transparent so that it can transmit active energy rays (such as excitation light, reference light, and reproduction light).

When the holographic recording medium has the support on one side or both sides of the recording layer, a transmission hologram or a reflection hologram can be recorded. When a support having anti-reflection characteristics is used on one side of the recording layer, a reflection hologram can be recorded.

A pattern for data addressing may be provided on the support. In this case, no limitation is imposed on the patterning method. For example, irregularities may be formed on the support itself, or the pattern may be formed on the reflecting layer described later. The pattern may be formed using a combination of these methods.

6-7-3. Protective Layer

The protective layer is a layer for preventing deterioration of the recording-reproduction propertied of the recording layer. No limitation is imposed on the specific structure of the protective layer, and any known protective layer can be used. For example, a layer formed of a water-soluble polymer, an organic or inorganic material, etc. can be formed as the protective layer.

No particular limitation is imposed on the formation position of the protective layer. The protective layer may be formed, for example, on the surface of the recording layer or between the recording layer and the support or may be formed on the outer surface side of the support. The protective layer may be formed between the support and another layer.

6-7-4. Reflecting Layer

The reflecting layer is formed when the holographic recording medium formed is of the reflection type. In the reflection holographic recording medium, the reflecting layer may be formed between the support and the recording layer or may be formed on the outer side of the support. Generally, it is preferable that the reflecting layer is present between the support and the recording layer.

Any known reflecting layer may be used, and a thin metal film, for example, may be used.

6-7-5. Anti-Reflection Film

In each of the transmission and reflection holographic recording mediums, an anti-reflection film may be disposed on the side on/from which information light, reference light, and reproduction light are incident/emitted or between the recording layer and the support. The anti-reflection film improves the efficiency of utilization of light and prevents the occurrence of noise.

Any known anti-reflection film may be used.

6-7-6. Method for Producing Holographic Recording Medium

No limitation is imposed on the method for producing the holographic recording medium of the present invention. For example, the holographic recording medium can be produced by coating the support with the polymerizable composition of the invention without using a solvent to form the recording layer. Any known coating method can be used. Specific examples of the coating method include a spray method, a spin coating method, a wire bar method, a dipping method, an air knife coating method, a roll coating method, a blade coating method, and a doctor roll coating method.

When a recording layer with a large thickness is formed, a method in which the polymerizable composition is molded using a die, a method in which the polymerizable composition is applied to a release film and punched with a die, etc. may be used to form the recording layer. The holographic recording medium of the invention may be produced by mixing the polymerizable composition of the present invention with a solvent or an additive to prepare a coating solution, coating the support with the coating solution, and then drying the coating solution to form the recording layer. In this case also, any coating method can be used. For example, any of the above described methods can be used.

No limitation is imposed on the solvent used for the coating solution. It is generally preferable to use a solvent that can dissolve the component used sufficiently, provides good coating properties, and does not damage the support such as a resin substrate. One solvent may be used alone, or any combination of two or more solvents may be used at any ratio. No limitation is imposed on the amount of the solvent used. However, from the viewpoint of coating efficiency and handleability, it is preferable to prepare a coating solution having a solid concentration of about 1 to about 100% by mass.

Examples of the solvent include: ketone-based solvents such as acetone, methyl ethyl ketone, methyl isobutyl ketone, cyclohexanone, and methyl amyl ketone; aromatic-based solvents such as toluene and xylene; alcohol-based solvents such as methanol, ethanol, propanol, n-butanol, heptanol, hexanol, diacetone alcohol, and furfuryl alcohol; ketone alcohol-based solvents such as diacetone alcohol and 3-hydroxy-3-methyl-2-butanone; ether-based solvents such as tetrahydrofuran and dioxane; halogen-based solvents such as dichloromethane, dichloroethane, and chloroform; cellosolve-based solvents such as methyl cellosolve, ethyl cellosolve, butyl cellosolve, methyl cellosolve acetate, and ethyl cellosolve acetate; propylene glycol-based solvents such as propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate, and dipropylene glycol dimethyl ether; ester-based solvents such as ethyl acetate, butyl acetate, amyl acetate, butyl acetate, ethylene glycol diacetate, diethyl oxalate, ethyl pyruvate, ethyl-2-hydroxybutyrate ethylacetoacetate, methyl lactate, ethyl lactate, methyl 2-hydroxyisobutyrate, and methyl 3-methoxypropionate; perfluoroalkyl alcohol-based solvents such as tetrafluoropropanol, octafluoropentanol, and hexafluorobutanol; highly polar solvents such as dimethylformamide, dimethylacetamide, N-methylpyrrolidone, and dimethyl sulfoxide; chain hydrocarbon-based solvents such as n-hexane and n-octane; cyclic hydrocarbon-based solvents such as cyclohexane, methylcyclohexane, ethylcyclohexane, dimethylcyclohexane, n-butylcyclohexane, tert-butylcyclohexane, and cyclooctane; and mixtures of these solvents.

Examples of the holographic recording medium production method include: a production method in which the recording layer is formed by coating the support with the polymerizable composition fused by heat and cooling the polymerizable composition to solidify the composition; a production method in which the recording layer is formed by coating the support with the polymerizable composition in liquid form and subjecting the polymerizable composition to thermal polymerization to cure the composition; and a production method in which the recording layer is formed by coating the support with the polymerizable composition in liquid form and subjecting the polymerizable composition to photopolymerization to cure the composition.

The thus-produced holographic recording medium can be in the form of a self-supporting slab or disk and can be used for three-dimensional image display devices, diffraction optical elements, large-capacity memories, etc.

In particular, the holographic recording medium of the present invention that uses the polymerizable composition of the invention has a high total Δn and is useful also for light guide plates for AR glasses.

6-7-7. Applications of Holographic Recording Medium

<Large-Capacity Memory Applications>

Information is written (recorded)/read (reproduced) in/from the holographic recording medium of the present invention by irradiating the medium with light.

To record information, light capable of causing a chemical change of the polymerizable monomer, i.e., its polymerization and a change in concentration, is used as the object light (referred to also as recording light).

For example, when information is recorded as a volume hologram, the object light together with the reference light is applied to the recording layer to allow the object light to interfere with the reference light in the recording layer. In this case, the interfering light causes polymerization of the polymerizable monomer and a change in its concentration within the recording layer. Therefore, the interference fringes cause refractive index differences within the recording layer, and the information is recorded as a hologram through the interference fringes recorded in the recording layer.

To reproduce the volume hologram recorded in the recording layer, prescribed reproduction light (generally the reference light) is applied to the recording layer. The applied reproduction light is diffracted by the interference fringes. Since the diffracted light contains the same information as that in the recording layer, the information recorded in the recording layer can be reproduced by reading the diffracted light using appropriate detection means.

The wavelength ranges of the object light, the reproduction light, and the reference light can be freely set according to their applications and may be the visible range or the ultraviolet range. Preferred examples of such light include light from lasers with good monochromaticity and directivity such as: solid lasers such as ruby, glass, Nd-YAG, and Nd-$YVO_4$ lasers; diode lasers such as GaAs, InGaAs, and GaN lasers; gas lasers such as helium-neon, argon, krypton, excimer, and $CO_2$ lasers; and dye lasers including dyes.

No limitation is imposed on the amounts of irradiation with the object light, the reproduction light, and the reference light, and these amounts can be freely set so long as recording and reproduction are possible. If the amounts of irradiation are extremely small, the chemical change of the polymerizable monomer is too incomplete, and the heat resistance and mechanical properties of the recording layer may not be fully obtained. If the amounts of irradiation are extremely large, the components of the recording layer (the components of the polymerizable composition of the invention) may deteriorate. Therefore, the object light, the reproduction light, and the reference light are applied generally at 0.1 $J/cm^2$ or more and 20 $J/cm^2$ or less according to the chemical composition of the polymerizable composition of the invention used to form the recording layer, the type of photopolymerization initiator, the amount of the photopolymerization initiator mixed, etc.

Examples of the holographic recording method include a polarized collinear holographic recording method and a reference light incidence angle multiplexing holographic recording method. When the holographic recording medium of the present invention is used as a recording medium, good recording quality can be provided using any of the recording methods.

<AR Glass Light Guide Plate Applications>

Volume holograms are recorded in the holographic recording medium of the present invention in the same manner as in the large-capacity memory applications.

The volume holograms recorded in the recording layer are irradiated with prescribed reproduction light through the recording layer. The applied reproduction light is diffracted by the interference fringes. In this case, even when the wavelength of the reproduction light does not coincide with the wavelength of the recording light, diffraction occurs when the Bragg condition for the interference fringes is satisfied. Therefore, by recording interference fringes corresponding to the wavelengths and incident angles of reproduction light beams to be diffracted, the reproduction light beams in a wide wavelength range can be diffracted, and the color display range of AR glasses can be increased.

By recording interference fringes corresponding to the wavelength and diffraction angle of reproduction light, the reproduction light entering from the outside of the holographic recording medium can be guided to the inside of the holographic recording medium, and the reproduction light guided inside the holographic recording medium can be reflected, split, and expanded or reduced in size. Moreover, the reproduction light guided through the inside of the holographic recording medium can be emitted to the outside of the holographic recording medium. This allows the viewing angle of AR glasses to be increased.

The wavelength ranges of the object light and the reproduction light can be freely set according to their applications, and the object light and the reproduction light may be in the visible range or in the ultraviolet range. Preferred examples of the object light and the reproduction light include light from the above-described lasers. The reproduction light is not limited to light from a laser etc., and display devices such as liquid crystal displays (LCDs), organic electroluminescent displays (OLEDs), etc. can also be used preferably.

No limitation is imposed on the amounts of irradiation with the object light, the reproduction light, and the reference light, and these amounts can be freely set so long as recording and reproduction are possible. If the amounts of irradiation are extremely small, the chemical change of the polymerizable monomer is too incomplete, and the heat resistance and mechanical properties of the recording layer may not be fully obtained. If the amounts of irradiation are extremely large, the components of the recording layer (the components of the polymerizable composition of the invention) may deteriorate. Therefore, the object light, the reproduction light, and the reference light are applied generally at 0.1 J/cm$^2$ or more and 20 J/cm$^2$ or less according to the chemical composition of the polymerizable composition of the invention used to form the recording layer, the type of photopolymerization initiator, the amount of the photopolymerization initiator mixed, etc.

6-8. Performance Indicator of Holographic Recording Medium

The total Δn of diffraction efficiency over the entire multiple recording is used as the indicator of the performance of the holographic recording medium. For a transmission hologram, the diffraction efficiency of the hologram is given as the ratio of the intensity of diffracted light to the sum of the intensity of transmitted light and the intensity of the diffracted light. Δn is computed from the following formula in Coupled Wave Theory (H. Kogelnik, The Bell System Technical Journal (1969), 48, 2909-2947) using the obtained diffraction efficiency, and the total over the entire multiple recording is used as the total Δn.

$$\eta = \sin^2\left(\frac{\pi \cdot T \cdot \Delta n}{\lambda \cdot \cos\theta}\right) \quad \text{[Math. 1]}$$

$$\text{total}\Delta n = \sum \Delta n$$

Here, η is the diffraction efficiency, and T is the thickness of the medium. λ is the wavelength of the reference light, and θ is the incident angle of the reference light.

In large-capacity memories, a large total Δn is preferred because this means that a larger amount of information can be recorded per unit volume. In AR glass applications, a large total Δn is preferred because this means that an image projected from a projector can be delivered to the eyes without loss of brightness, because power consumption can be reduced, and because the viewing angle can be increased.

EXAMPLES

The present invention will be described in more detail by way of Examples. However, the present invention is not limited to the Examples so long as they do not depart from the scope of the invention.

Methods for synthesizing compounds will be described in detail using chemical formulas including the synthesis processes of the compounds.

[Materials Used]

Raw materials of compositions used in the Examples and Comparative Examples are as follows.

<Isocyanate>

DURANATE (registered trademark) TSS-100: hexamethylene diisocyanate-based polyisocyanate (NCO: 17.6%) (manufactured by Asahi Kasei Corporation)

<Polyol>

PLACCEL PCL-205U: polycaprolactone diol (molecular weight: 530) (manufactured by Daicel Corporation)

PLACCEL PCL-305: polycaprolactone triol (molecular weight: 550) (manufactured by Daicel Corporation)

<Photopolymerization Initiator>

HLI02: 1-(9-ethyl-6-cyclohexanoyl-9H-carbazol-3-yl)-1-(O-acetyloxime)glutaric acid methyl ester <Radical Scavenger>

TEMPOL: 4-hydroxy-2,2,6,6-tetramethylpiperidine-1-oxyl free radicals (manufactured by TOKYO CHEMICAL INDUSTRY Co., Ltd.)

<Urethane Polymerization Catalyst>

Octylic acid solution of bismuth tris(2-ethylhexanoate) (amount of effective component: 56% by weight)

Synthesis Example 1

A method described in JP2017-14213A was used. Specifically, the following synthesis method was used to produce bis(4-dibenzothiophenyl)disulfide (DBTDS) as a compound S-1 and then produce 4-dibenzothiophenethiol (DBTSH) as a compound S-2.

[Chem. 16]

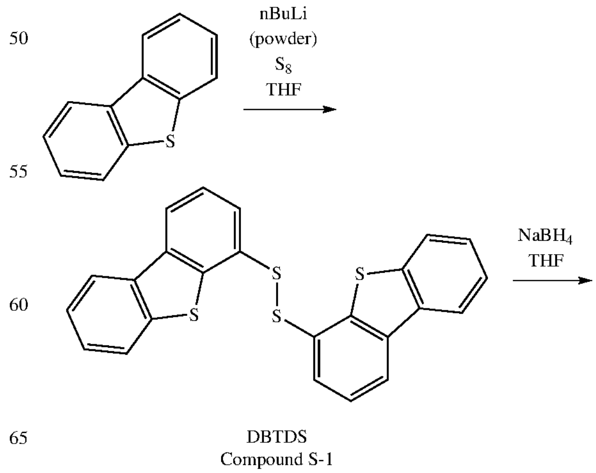

DBTDS
Compound S-1

-continued

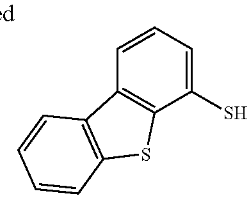

DBTSH
Compound S-2

20 g of dibenzothiophene was dissolved in 300 mL of THF. While the mixture was cooled to 0° C., 74.6 mL of a n-butyllithium hexane solution with a concentration of 1.6 M was added, and the resulting mixture was heated to 20° C. and stirred for 2 hours. The obtained brown reaction solution was cooled to −40° C., and 3.8 g of sulfur (a powder form, product of Wako Pure Chemical Industries, Ltd.) was added. The resulting reaction solution was stirred at −40° C. for 30 minutes, and 5 mL of water was added to the reaction mixture to stop the reaction.

The obtained solution was concentrated using an evaporator, and the obtained solid was washed with 100 mL of toluene for 39 minutes. The yellow solid was separated by filtration to thereby produce DBTDS used as the compound S-1.

The compound S-1 was dispersed in 200 mL of THF. Then 4.5 g of sodium borohydride was added, and the mixture was stirred at 50° C. for 1 hour. Then the reaction solution was filtrated. The resulting solution was concentrated using an evaporator, and 200 mL of toluene was added. The toluene solution was washed with water, 1N hydrochloric acid, a 1N aqueous sodium hydroxide solution, and the resulting solution was concentrated. The concentrate was subjected to recrystallization with hexane, and 9.4 g of DBTSH used as the compound S-2 was obtained (yield: 40%).

Several milliliters of deuterochloroform was added to an appropriate amount (about 10 mg) of the compound S-2 obtained to dissolve it. If insoluble matter was found, the mixture was filtered through a cotton plug. The filtrate was transferred to a special-purpose sample tube, and the sample tube was covered with a lid. This sample was used for measurement of resonance states of hydrogen using a 400 MHz nuclear magnetic resonance (NMR) apparatus. The attribution of each of the resonance lines to hydrogen in the compound was determined to confirm that the target compound was obtained. The measurement data is shown below. For each of the following target compounds, the same measurement was performed to confirm the target compound was obtained. The measurement data is shown below.

$^1$H NMR (400 MHz, $CDCl_3$, δ, ppm) 3.63 (s, 1H), 7.35 (Ar, 1H), 7.45 (Ar, 3H), 7.89 (Ar, 1H), 8.05 (Ar, 1H), 8.14 (Ar, 1H)

Synthesis Example 2

The following synthesis method was used to produce bis[2-(2-benzothiazolyl)phenyl]disulfide (MPBTD) as a compound S-3.

[Chem. 17]

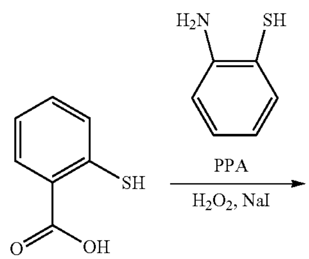

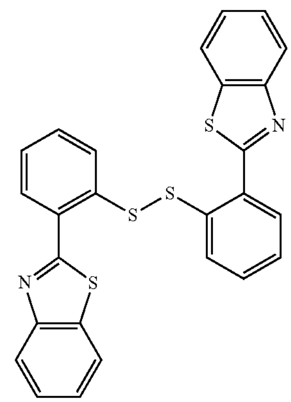

MPBTD
Compound S-3

170 g of thiosalicylic acid and 165 g of 2-aminobenzenethiol were dissolved in 1.1 L of polyphosphoric acid, and the mixture was allowed to react at 170° C. for 2 hours. The resulting mixture was cooled to 100° C. or lower, then poured into 3 L of water, and stirred vigorously. The mixture was stirred at room temperature for 2 hours, and the solid was separated by filtration. The obtained solid was poured into 3 L of an aqueous sodium hydrogencarbonate solution, and the mixture was stirred for 20 minutes. The solid was separated by filtration, poured into 3 L of water, subjected to suspension washing, and separated by filtration to thereby obtain 260 g of a crude product.

260 g of the crude product and 1.6 g of sodium iodide were dissolved in 5 L of THF. While the internal temperature was maintained at 15° C. or lower, 78 mL of a 30% aqueous hydrogen peroxide solution was slowly added dropwise to the mixture. The resulting mixture was stirred at 15° C. for 15 minutes, and LC analysis was performed to confirm completion of the reaction. 500 mL of saturated sodium sulfite was slowly added to stop the reaction, and then 8 L of water was added to dilute the mixture. The solid generated was separated by filtration and washed twice with 300 mL of desalted water to thereby obtain about 300 g of a crude product.

The crude product was dissolved in THF and purified by silica gel chromatography to thereby obtain 240 g of a pale yellow solid. The yellow solid was subjected to suspension washing with 500 mL of THF and washed twice with 20 mL of THF to thereby obtain 220 g of a white solid, i.e., MPBPD used as the compound S-3.

The NMR measurement data of the compound S-3 is as follows.

$^1$H NMR (400 MHz, $CDCl_3$, δ, ppm) 7.29 (td, 2H), 7.35 (td, 2H), 7.42 (td, 3H), 7.51 (td, 2H), 7.83 (dd, 2H), 7.90 (dd, 2H), 7.93 (dd, 2H), 8.13 (d, 2H)

Example 1

The following synthesis method was used to produce a compound M-1.

[Chem. 18]

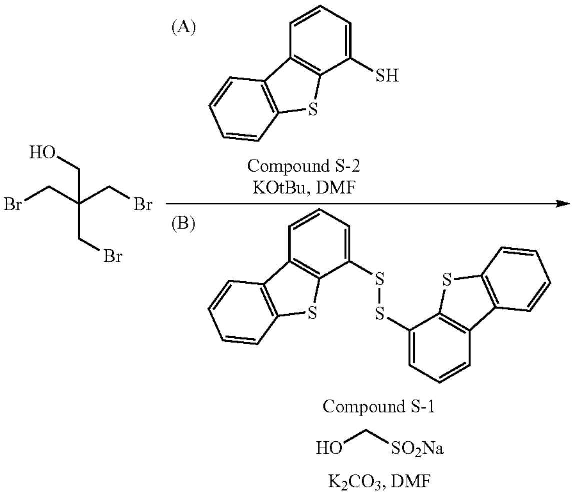

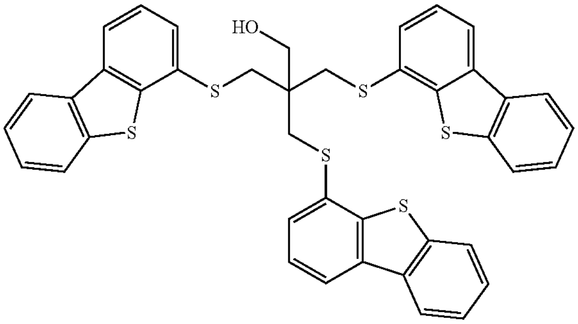

Compound S-4

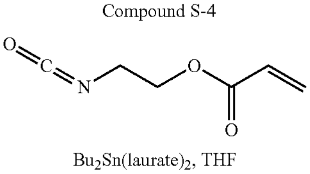

-continued

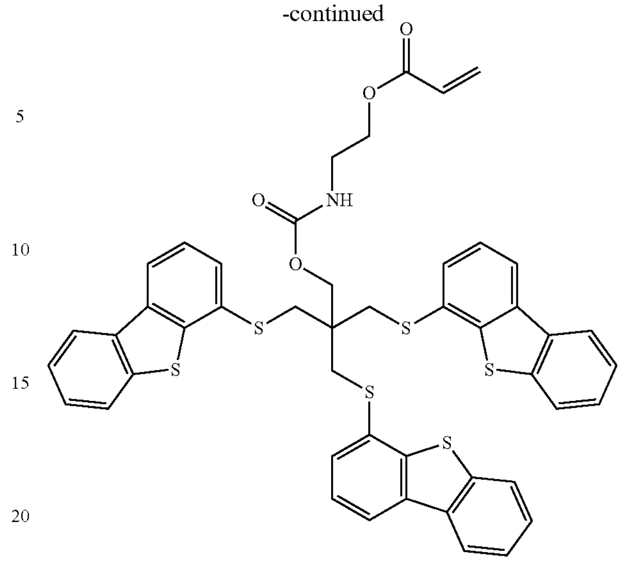

Compound M-1

A compound S-4 used as an intermediate was prepared by two routes (A) and (B).

Route (A): 20 g of the DBTSH (compound S-2) obtained in Synthesis Example 1 and 50 g of cesium carbonate were dissolved in 200 mL of methyl ethyl ketone (MEK). 9 g of pentaerythritoltribromide was added to the prepared solution, and the mixture was heated to 90° C. While the progress of the reaction was checked by LC analysis, the mixture was stirred for 5 hours. Water was added to the reaction solution, and then 100 mL of ethyl acetate was added to extract the organic layer. The obtained organic layer was extracted twice with 50 mL of water, and the aqueous layer generated was back-extracted twice with 100 mL of ethyl acetate. The organic layer obtained was dried over mirabilite and then concentrated. The crude product obtained by concentrating the organic layer was purified using a silica gel column (hexane/ethyl acetate) to thereby obtain 10 g of the compound S-4 (yield: 49%).

Route (B): 8.3 g of the DBTDS (compound S-1) obtained in Synthesis Example 1, 3.5 g of pentaerythritoltribromide, 14 g of potassium carbonate, and 10 g of sodium formaldehyde sulfoxylate (Rongalite) were suspended in 25 mL of N,N-dimethylformamide (DMF). Then the reaction mixture was heated to 100° C. While the progress of the reaction was checked by LC analysis, the mixture was stirred for 3 hours. Water was added to the reaction solution, and then 100 mL of ethyl acetate was added to extract the organic layer. The obtained organic layer was extracted twice with 60 mL of water, and the aqueous layer generated was back-extracted twice with 70 mL of ethyl acetate. The organic layer obtained was dried over mirabilite and then concentrated. The crude product obtained by concentrating the organic layer was subjected to suspension washing with a 2:1 solvent mixture of hexane:ethyl acetate to thereby obtain 4.8 g of the compound S-4 (yield: 61%).

The NMR measurement data of the compound S-4 is as follows.

$^1$H NMR (400 MHz, $CDCl_3$, δ, ppm) 3.38 (s, 6H), 3.75 (d, 2H), 7.22 (dd, 3H), 7.43 (Ar, 9H), 7.77 (Ar, 3H), 7.86 (dd, 3H), 8.02 (Ar, 3H)

The above-obtained compound S-4 (11 g) was dissolved in 55 mL of tetrahydrofuran (THF), and 190 mg of dibutyltin dilaurate was added. 2.55 g of 2-isocyanatoethyl acrylate (Karenz AOI manufactured by Showa Denko K.K.) was added to the prepared solution, and the resulting mixture was allowed to react at room temperature. After a lapse of 24 hours, an additional 0.4 g of 2-isocyanatoethyl acrylate was added, and the mixture was allowed to further react for 24 hours. 100 mL of ethyl acetate was added to the reaction solution, and the resulting mixture was concentrated to about 50 mL. Insoluble matter was removed, and the mixture was concentrated. The crude product obtained was purified using a silica gel column (hexane/ethyl acetate) to thereby obtain 7.6 g of the compound M-1 (yield: 58%).

The NMR measurement data of the compound M-1 is as follows.

$^1$H NMR (400 MHz, $CDCl_3$, δ, ppm) 3.19 (dt, 2H), 3.36 (s, 6H), 4.02 (m, 2H), 4.21 (s, 2H), 4.42 (m, 2H), 5.79 (dd, 1H), 6.03 (dd, 1H), 6.37 (d, 1H), 7.19 (Ar, 3H), 7.38 (Ar, 3H), 7.43 (Ar, 6H), 7.76 (Ar, 3H), 7.84 (Ar, 3H), 8.01 (Ar, 3H)

<Production of Holographic Recording Medium 1>

0.269 g of the compound M-1 used as the polymerizable monomer, 0.0097 g of a photopolymerization initiator HLI02, and 3.33 mg of the radical scavenger TEMPOL were dissolved in 2.53 g of DURANATE (registered trademark) TSS-100 to prepare solution A.

Separately, 1.73 g of PLACCEL PCL-205U and 0.74 g of PLACCEL PCL-305 (PLACCEL PCL-205U:PLACCEL PCL-305=70:30 (mass ratio)) were mixed, and 0.3 mg of an octylic acid solution of bismuth tris(2-ethylhexanoate) was dissolved in the mixture to thereby prepare solution B.

The solutions A and B were separately degassed at 45° C. under reduced pressure for 2 hours. Then 2.39 g of the solution A and 2.11 g of the solution B were mixed under stirring and further degassed in a vacuum for several minutes.

Then the vacuum degassed solution mixture was poured onto a microscope slide with 0.5 mm-thick spacer sheets placed on two opposite edges, and another microscope slide was placed thereon. Clips were used to fix the edges, and heating was performed at 80° C. for 24 hours to produce a holographic recording medium 1 as an evaluation sample. In this evaluation sample, a recording layer with a thickness of 0.5 mm was formed between the microscope slides used as covers.

In the holographic recording medium 1, the ratio of the number of isocyanate groups in the solution A to the number of isocyanate reactive groups in the solution B was 1.0. The holographic recording medium 1 contained 58.3 μmol/g of the polymerizable monomer, 3.63 μmol/g of the photopolymerization initiator, and 3.63 μmol/g of the radical scavenger.

<Production of Holographic Recording Medium 2>

0.568 g of the compound M-1 used as the polymerizable monomer, 0.0204 g of the photopolymerization initiator HLI02, and 7.04 mg of the radical scavenger TEMPOL were dissolved in 2.62 g of DURANATE (registered trademark) TSS-100 to prepare solution A.

Separately, 1.19 g of PLACCEL PCL-205U and 1.19 g of PLACCEL PCL-305 (PLACCEL PCL-205U:PLACCEL PCL-305=50:50 (weight ratio)) were mixed, and 0.3 mg of an octylic acid solution of bismuth tris(2-ethylhexanoate) was dissolved in the mixture to thereby prepare solution B.

The solutions A and B were separately degassed at 45° C. under reduced pressure for 2 hours. Then 2.58 g of the solution A and 1.91 g of the solution B were mixed under stirring and further degassed in a vacuum for several minutes.

Then the vacuum degassed solution mixture was poured onto a microscope slide with 0.5 mm-thick spacer sheets placed on two opposite edges, and another microscope slide was placed thereon. Clips were used to fix the edges, and heating was performed at 80° C. for 24 hours to produce a holographic recording medium 2 as an evaluation sample. In this evaluation sample, a recording layer with a thickness of 0.5 mm was formed between the microscope slides used as covers.

In the holographic recording medium 2, the ratio of the number of isocyanate groups in the solution A to the number of isocyanate reactive groups in the solution B was 1.0. The holographic recording medium 2 contained 116 μmol/g of the polymerizable monomer, 7.26 μmol/g of the photopolymerization initiator, and 7.26 μmol/g of the radical scavenger.

[Holographic Recording and Evaluation Method]

Each of the holographic recording mediums 1 and 2 produced as the evaluation samples was used to perform holographic recording and evaluate the holographic recording performance of each holographic recording medium using procedures described below.

Holographic recording was performed using a semiconductor laser with a wavelength of 405 nm. An exposure device shown in FIG. 1 was used to perform two-beam plane-wave holographic recording at an exposure power density per beam of 7.5 mW/cm$^2$. The medium was rotated from −18° to 18°, and angular multiple recording was performed in the same position. The diffraction efficiency for each multiple recording operation was measured. The obtained diffraction efficiency was used to compute Δn, and the total over the entire multiple recording was used as the total Δn.

Details will next be described.

(Holographic Recording)

FIG. 1 is a structural diagram showing the outline of the device used for holographic recording.

In FIG. 1, S represents a holographic recording medium sample, and M1 to M3 represent mirrors. PBS represents a polarizing beam splitter. L1 represents a recording laser light source emitting light with a wavelength of 405 nm (a single mode laser ("L1" in FIG. 1) manufactured by TOPTICA Photonics and capable of emitting light with a wavelength of about 405 nm). L2 represents a reproduction laser light source emitting light with a wavelength of 633 nm. PD1, PD2, and PD3 represent photodetectors. 1 represents an LED unit.

As shown in FIG. 1, a light beam with a wavelength of 405 nm was split using the polarizing beam splitter ("PBS" in the FIGURE) into two beams intersecting on a recording surface such that the angle therebetween was 37.3°. In this case, the light beam was split such that a bisector of the angle between the two beams was perpendicular to the recording surface, and the two beams obtained by splitting the light beam were applied such that the vibration planes of the electric field vectors of the two beams were perpendicular to a plane including the two intersecting beams.

After the holographic recording, a He—Ne laser capable of emitting light with a wavelength of 633 nm (V05-LHP151 manufactured by Melles Griot: "L2" in the FIGURE) was used to apply the light to the recording surface at an angle of 30.0°. The diffracted light was detected using a photo diode and a photosensor amplifier (S2281 and C9329: manufactured by Hamamatsu Photonics K.K., "PD1" in the FIGURE) to determine whether the holographic recording was correctly performed.

(Measurement of Diffraction Efficiency)

Multiple recording was performed while the sample was moved with respect to the optical axes such that the angle of the sample (the angle between the normal to the sample and a bisector of the interior angle of the two beams, i.e., incident light beams from the mirrors M1 and M2 in FIG. 1, at the intersection of the beams) was changed from −18° to 18°. Specifically, the multiple recording was performed 91 times while the angle of the sample was changed in steps of 0.4° or 121 times while the angle was changed in steps of 0.3°.

After the multiple recording, the LED unit (1 in the FIGURE, center wavelength: 405 nm) was turned on for a given period of time to completely consume the remaining initiator and the remaining monomer. This process is referred to as postexposure. The power of the LED was 100 $mW/cm^2$, and the irradiation was performed such that the integrated energy was 12 $J/cm^2$.

The diffraction efficiency of a hologram is given as the ratio of the intensity of the diffracted light to the sum of the intensity of the diffracted light and the intensity of the transmitted light. Light (wavelength: 405 nm) from the mirror M1 in FIG. 1 was directed to the sample, and the diffraction efficiency was measured at angles of −19° to 19°. Δn was computed from the following formula in Coupled Wave Theory (H. Kogelnik, The Bell System Technical Journal (1969), 48, 2909-2947) using the obtained diffraction efficiency, and the total over the entire multiple recording was used as the total Δn.

[Math. 2]

$$\eta = \sin^2\left(\frac{\pi \cdot T \cdot \Delta n}{\lambda \cdot \cos\theta}\right)$$

$$\text{total}\Delta n = \sum \Delta n$$

Here, η is the diffraction efficiency, and T is the thickness of the medium. λ is the wavelength of the reference light, and θ is the incident angle of the reference light (18.65°).

A plurality of samples prepared were used. The evaluation was performed a plurality of times under different irradiation energy conditions, i.e., while the irradiation energy at the beginning of irradiation was increased or decreased and the total irradiation energy was increased or decreased. A search for conditions under which the polymerizable monomer was almost completely consumed (the total Δn substantially reached equilibrium by the multiple recording) was performed in order to maximize the total Δn. The maximum value obtained was used as the total Δn of the medium.

(Measurement of Transmittance Before Recording and Transmittance after Recording)

The transmittance before recording of an evaluation sample was determined before recording by measuring the ratio of the power of the transmission light to the power of the incident light.

Moreover, the transmittance after recording of the evaluation sample subjected to postexposure was determined after recording by measuring the ratio of the power of the transmission light to the power of the incident light.

The results of the evaluation on the holographic recording mediums 1 and 2 using the methods described above are shown in Table 1 below.

Example 2

A compound M-2 was produced by the following synthesis method.

[Chem. 19]

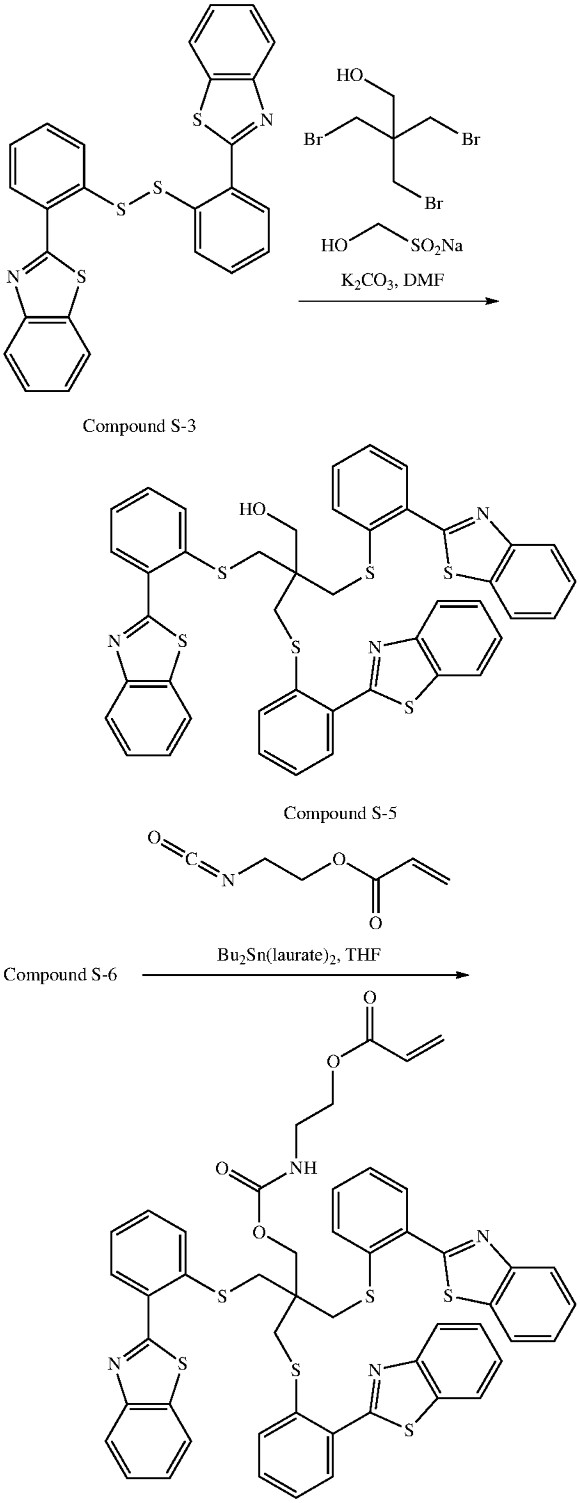

Compound S-3

Compound S-5

Compound S-6

Compound M-2

1.12 g of the compound S-3 (MPBTD) obtained in Synthesis Example 2, 500 mg of pentaerythritoltribromide, 640 mg of potassium carbonate, and 820 mg of sodium formaldehyde sulfoxylate (Rongalite) were suspended in 2.5 mL of N,N-dimethylformamide (DMF). The reaction mixture was heated to 80° C. While the progress of the reaction was checked by LC analysis, the mixture was stirred for 4 hours. The compound S-3 (190 mg) and 140 mg of Rongalite were further added, and the resulting mixture was further stirred at 80° C. for 2 hours. Water was added to the reaction solution, and then 50 mL of ethyl acetate was added to extract the organic layer. The obtained organic layer was extracted twice with 30 mL of water, and the aqueous layer generated was back-extracted twice with 50 mL of ethyl acetate. The organic layer obtained was dried over mirabilite and then concentrated. The crude product obtained by concentrating the organic layer was purified using a silica gel column (hexane/ethyl acetate) to thereby obtain 1.17 g of a compound S-5 (yield: 93%).

The NMR measurement data of the compound S-5 is as follows.

$^1$H NMR (400 MHz, $CDCl_3$, δ, ppm) 3.17 (s, 6H), 3.28 (t, 1H), 3.64 (d, 2H), 7.23 (Ar, 6H), 7.38 (Ar, 3H), 7.48 (Ar, 6H), 7.85 (Ar, 3H), 7.88 (Ar, 3H), 8.07 (Ar, 3H)

The above-obtained compound S-5 (1.8 g) was dissolved in 9 mL of tetrahydrofuran (THF), and 28 mg of dibutyltin dilaurate was added. 375 mg of 2-isocyanatoethyl acrylate (Karenz AOI manufactured by Showa Denko K.K.) was added to the prepared solution, and the mixture was allowed to react at room temperature. After a lapse of 24 hours, an additional 375 mg of 2-isocyanatoethyl acrylate was added, and the mixture was allowed to further react for 24 hours. A 0.1M aqueous sodium hydroxide solution was added to the reaction solution, and 50 mL of ethyl acetate was added to extract the organic layer. The obtained organic layer was extracted twice with 30 mL of water, and the aqueous layer generated was back-extracted twice with 50 mL of ethyl acetate. The resulting organic layer was dried over magnesium sulfate and concentrated at 25° C. or lower. The crude product obtained by concentrating the organic layer was purified using a silica gel column (hexane/ethyl acetate) to thereby obtain 0.7 g of the compound M-2 (yield: 33%).

The NMR measurement data of the compound M-2 is as follows.

$^1$H NMR (400 MHz, $CDCl_3$, δ, ppm) 3.27 (dt, 2H), 3.93 (s, 6H), 4.12 (t, 2H), 5.25 (t, 1H), 5.80 (dd, 1H), 6.10 (dd, 1H), 6.40 (d, 1H), 7.16 (Ar, 3H), 7.23 (Ar, 3H), 7.39 (Ar, 6H), 7.48 (Ar, 3H), 7.85 (Ar, 3H), 7.90 (Ar, 3H), 8.04 (Ar, 3H)

A holographic recording medium 1 was produced in the same manner as in Example 1 except that the compound M-2 was used as the polymerizable monomer, and evaluation of the holographic recording medium 1 was performed. The results are shown in Table 1 below.

Example 3

A compound M-3 was produced by the following synthesis method.

[Chem. 20]

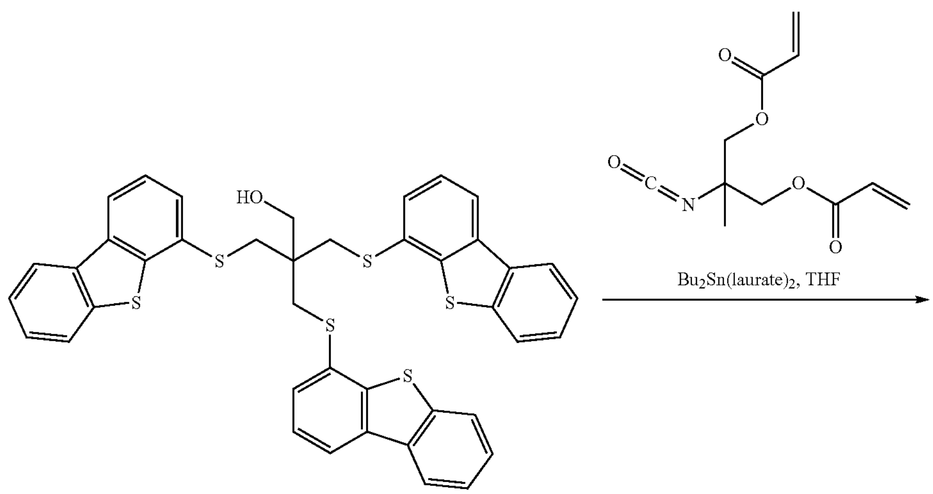

Compound S-4

-continued

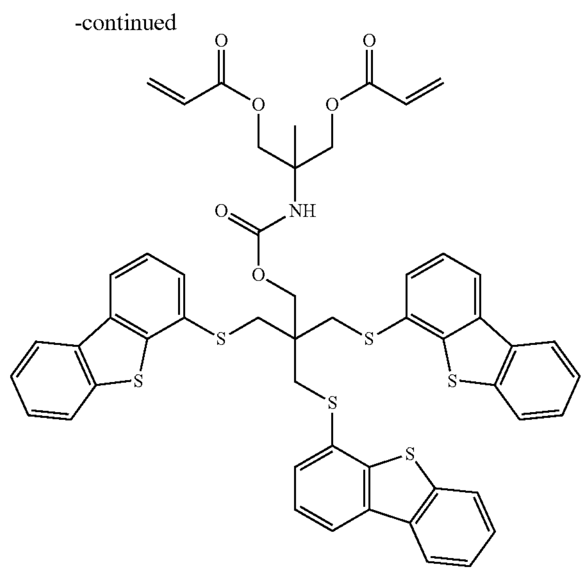

Compound M-3

The compound S-4 (1.4 g) obtained in Example 1 was dissolved in 10 mL of tetrahydrofuran, and 22 mg of dibutyltin dilaurate was added. 550 mg of 1,1-(bisacryloyloxymethyl)ethyl isocyanate (Karenz BEI manufactured by Showa Denko K.K.) was added to the prepared solution, and the mixture was allowed to react at room temperature. After a lapse of 24 hours, an additional 110 mg of 1,1-(bisacryloyloxymethyl)ethyl isocyanate was added, and the mixture was allowed to further react for 24 hours. A saturated aqueous sodium carbonate solution was added to the reaction solution, and then 50 mL of ethyl acetate was added to extract the organic layer. The organic layer obtained was extracted twice with 50 mL of water, and the aqueous layer generated was back-extracted twice with 50 mL of ethyl acetate. The resulting organic layer was dried over mirabilite and concentrated at 25° C. or lower. The crude product obtained by concentrating the organic layer was purified using a silica gel column (hexane/ethyl acetate) and further purified by a reversed-phase column to thereby obtain 1.5 g of the compound M-3 (yield: 81%).

The NMR measurement data of the compound M-3 is as follows.

$^1$H NMR (400 MHz, $CDCl_3$, δ, ppm) 1.23 (s, 3H), 3.39 (s, 6H), 4.09 (d, 2H), 4.20 (d, 2H), 4.22 (s, 2H), 4.63 (s, 1H), 5.76 (d, 2H), 6.02 (dd, 2H), 6.35 (d, 2H), 7.20 (Ar, 3H), 7.39 (Ar, 3H), 7.45 (Ar, 6H), 7.77 (Ar, 3H), 7.86 (Ar, 3H), 8.03 (Ar, 3H)

A holographic recording medium 2 was produced in the same manner as in Example 1 except that a mixture of the compound M-3 and a compound M-9 described later in Comparative Example 9 (molar ratio: 10/90) was used as the polymerizable monomer, and evaluation of the holographic recording medium 2 was performed. The results are shown in Table 1 below.

Example 4

A compound M-4 was produced by the following synthesis method.

[Chem. 21]

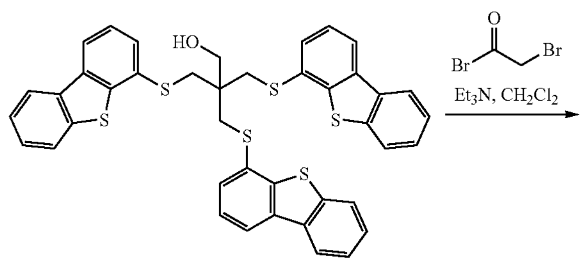

Compound S-4

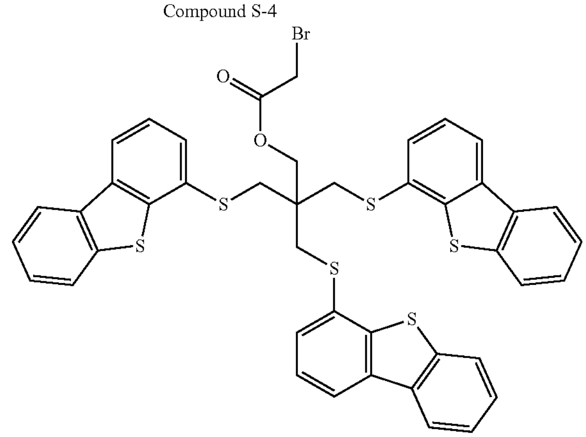

Compound S-6

Compound S-6

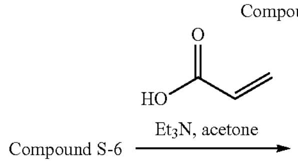

-continued

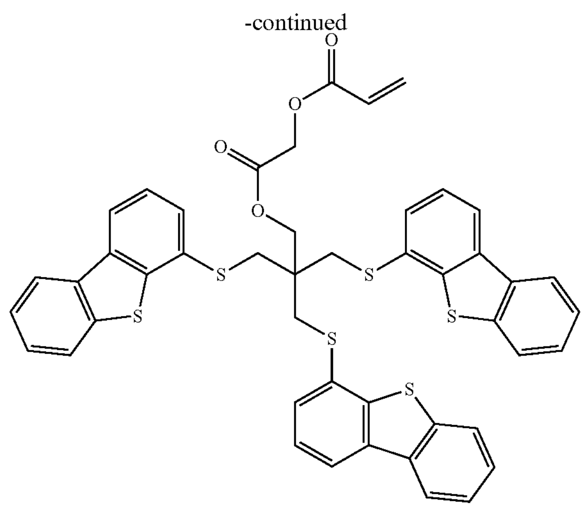

Compound M-4

The compound S-4 (3.0 g) obtained in Example 1 and triethylamine (3.5 mL) were dissolved in 15 mL of dichloromethane. The mixture was cooled to 0° C., and then 540 mg of bromoacetic acid bromide was slowly added dropwise. The mixture was stirred at room temperature for 1 hour and then cooled again to 0° C. An additional 540 mg of bromoacetic acid bromide was added dropwise to the resulting reaction mixture. The mixture was stirred at room temperature for 1 hour, and 20 mL of a saturated aqueous sodium hydrogencarbonate solution and 50 mL of ethyl acetate were added sequentially to perform an extraction operation. The organic layer obtained was extracted twice with 50 mL of water, and the aqueous layer generated was back-extracted twice with 50 mL of ethyl acetate. The resulting organic layer was dried over mirabilite and concentrated to thereby obtain 2.2 g of a crude product of a compound S-6.

The crude product was dissolved in 11 mL of acetone, and 1.6 mL of triethylamine was added. 500 mg of acrylic acid was slowly added to the mixture, and the resulting mixture was stirred at room temperature for 1 hour. Another 500 mg of acrylic acid was added, and the resulting mixture was further stirred for 1 hour. 20 mL of a saturated aqueous sodium hydrogencarbonate solution was added to the reaction mixture, and the resulting mixture was extracted with 50 mL of dichloromethane. The aqueous layer was further extracted with 50 mL of dichloromethane, and the resulting organic layer was washed with 60 mL of water. The organic layer was dried over mirabilite, concentrated, and purified using a silica gel column (hexane/ethyl acetate) to thereby obtain 440 mg of the compound M-4 (yield: 13%).

The NMR measurement data of the compound M-4 is as follows.

$^1$H NMR (400 MHz, $CDCl_3$, δ, ppm) 3.34 (s, 6H), 4.23 (s, 2H), 4.27 (s, 2H) 5.76 (dd, 1H), 6.00 (dd, 1H), 6.32 (d, 1H), 7.21 (Ar, 3H), 7.39 (Ar, 3H), 7.43 (Ar, 6H), 7.76 (Ar, 3H), 7.87 (Ar, 3H), 8.01 (Ar, 3H)

A holographic recording medium 1 was produced in the same manner as in Example 1 except that the compound M-4 was used as the polymerizable monomer, and evaluation of the holographic recording medium 1 was performed. The results are shown in Table 1 below.

Example 5

A compound M-5 was produced by the following synthesis method.

[Chem. 22]

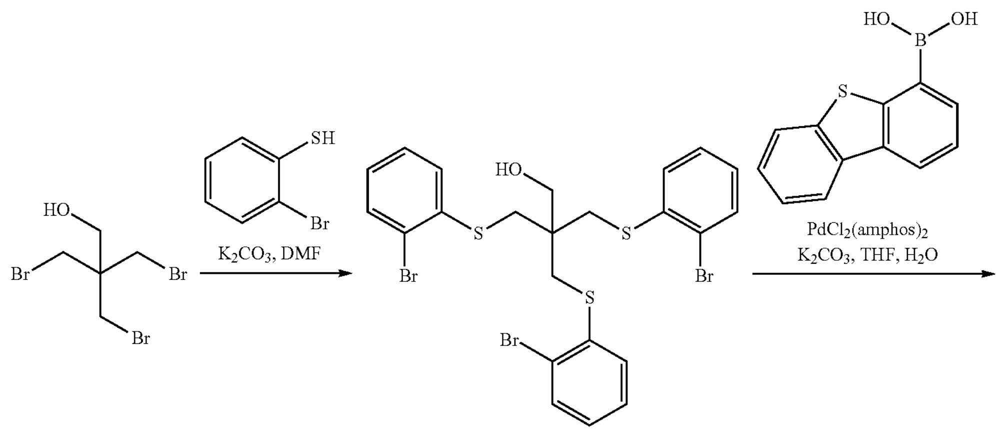

Compound S-7

-continued

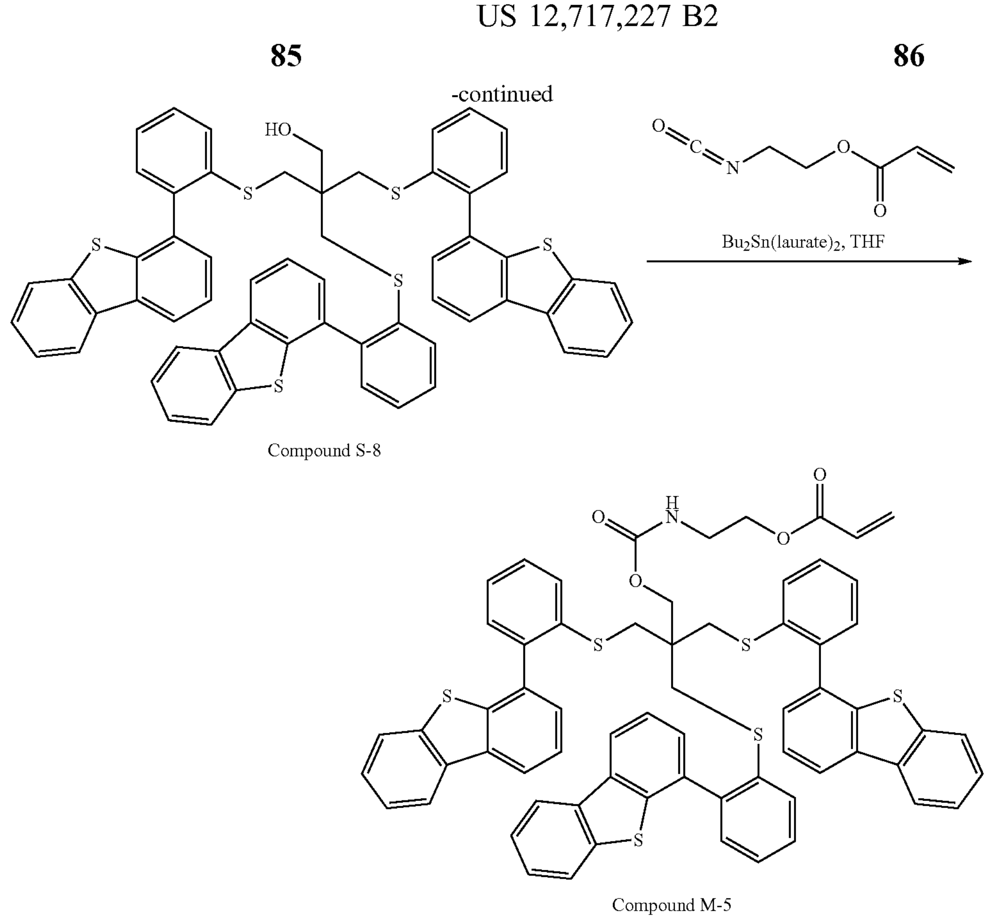

Compound S-8

Compound M-5

13.60 g of 2-bromobenzenethiol, 7.08 g of pentaerythritoltribromide, and 9.04 g of potassium carbonate were suspended in 21 mL of N,N-dimethylformamide (DMF). The reaction mixture was heated to 100° C. While the progress of the reaction was checked by LC analysis, the mixture was stirred for 4 hours. The resulting mixture was cooled to room temperature, extracted with ethyl acetate, and washed with water. The aqueous layer was back-extracted twice with ethyl acetate. The organic layer obtained was dried over mirabilite and then concentrated. The crude product obtained by concentrating the organic layer was purified using a silica gel column (hexane/ethyl acetate) to thereby obtain 13.2 g of a compound S-7 (yield: 93%).

The NMR measurement data of the compound S-7 is as follows.

$^1$H NMR (400 MHz, $CDCl_3$, δ, ppm) 3.23 (s, 6H), 3.79 (d, 2H), 6.98 (Ar, 3H), 7.19 (Ar, 3H), 7.33 (Ar, 3H), 7.47 (Ar, 3H)

The above-obtained compound S-7 (2.0 g), 3.5 g of dibenzothiophene-4-boronic acid, and 2.5 g of potassium carbonate were suspended in 20 mL of THF and 2.0 mL of water, and nitrogen gas was bubbled through the mixture to degas the mixture. 30 mg of dichlorobis[di-t-butyl(p-dimethylaminophenyl)phosphino]palladium (II) was added to the reaction solution, and nitrogen gas was further bubbled through the mixture for 10 minutes. The reaction solution was heated in a nitrogen atmosphere and stirred at reflux for 6 hours. The resulting mixture was cooled to room temperature, extracted with ethyl acetate, and washed with water. The aqueous layer was extracted twice with ethyl acetate. 0.4 g of activated carbon was added to the obtained organic layer, and the mixture was stirred for 30 minutes. The mixture was filtered through celite and concentrated. The crude product obtained was purified using a silica gel column (hexane/ethyl acetate) to thereby obtain 2.9 g of a compound S-8 (yield: 98%).

The NMR measurement data of the compound S-8 is as follows.

$^1$H NMR (400 MHz, $CDCl_3$, δ, ppm) 2.62 (s, 6H), 3.00 (d, 2H), 7.16 (Ar, 12H), 7.41 (Ar, 12H), 7.70 (Ar, 3H), 8.08 (Ar, 3H), 8.15 (Ar, 3H)

The above-obtained compound S-8 (2.9 g) was dissolved in 15 mL of tetrahydrofuran (THF), and 40 mg of dibutyltin dilaurate was added. 510 mg of 2-isocyanatoethyl acrylate (Karenz AOI manufactured by Showa Denko K.K.) was added to the prepared solution, and the mixture was allowed to react at room temperature. After a lapse of 24 hours, an additional 500 mg of 2-isocyanatoethyl acrylate was added, and the mixture was allowed to further react for 24 hours. Water was added to the reaction solution, and then 50 mL of ethyl acetate was added to extract the organic layer. The obtained organic layer was extracted twice with 30 mL of water, and the aqueous layer generated was back-extracted twice with 50 mL of ethyl acetate. The resulting organic layer was dried over magnesium sulfate and concentrated at 30° C. or lower. The crude product obtained by concentrating the organic layer was purified using a silica gel column (hexane/ethyl acetate) to thereby obtain 1.5 g of the compound M-5 (yield: 45%).

The NMR measurement data of the compound M-5 is as follows.

$^1$H NMR (400 MHz, $CDCl_3$, δ, ppm) 2.53 (s, 6H), 3.07 (m, 2H), 3.53 (s, 2H), 3.99 (t, 2H), 4.14 (dd, 1H), 5.81 (d, 1H), 6.10 (dd, 1H), 6.40 (d, 1H), 7.11 (Ar, 12H), 7.24 (Ar, 3H), 7.36 (Ar, 3H), 7.43 (Ar, 6H), 7.71 (Ar, 3H), 8.08 (Ar, 3H), 8.16 (Ar, 3H)

A holographic recording medium 1 was produced in the same manner as in Example 1 except that the compound M-5 was used as the polymerizable monomer, and evaluation of the holographic recording medium 1 was performed. The results are shown in Table 1 below.

Example 6

A compound M-6 was produced by the following synthesis method.

[Chem. 23]

Compound S-7

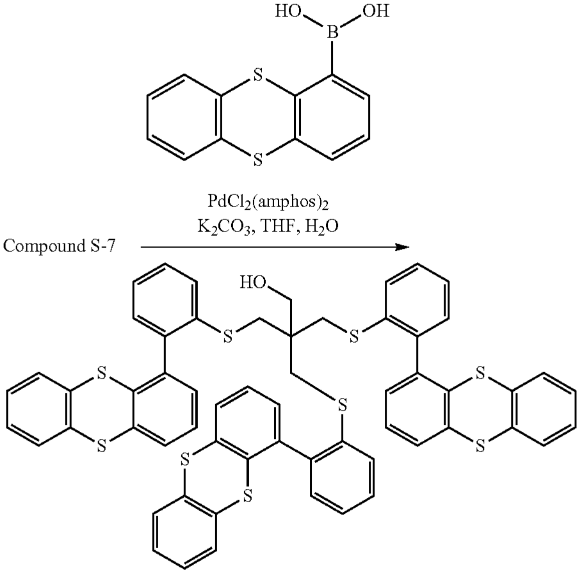

Compound S-9

Compound S-9

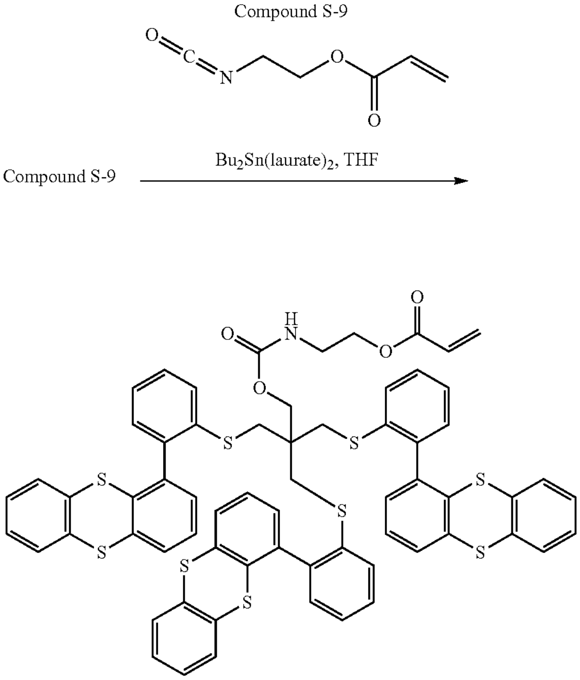

Compound M-6

The compound S-7 (2.0 g) obtained in Example 5, 2.7 g of thianthrene-1-boronic acid, and 2.5 g of potassium carbonate were suspended in 20 mL of THF and 2.0 mL of water, and nitrogen gas was bubbled through the mixture to degas the mixture. 30 mg of dichlorobis[di-t-butyl(p-dimethylaminophenyl)phosphino]palladium (II) was added to the reaction solution, and nitrogen gas was further bubbled through the mixture for 10 minutes. The reaction solution was heated in a nitrogen atmosphere and stirred at reflux for 6 hours. The resulting mixture was cooled to room temperature, extracted with ethyl acetate, and washed with water. The aqueous layer was extracted twice with ethyl acetate. 0.4 g of activated carbon was added to the obtained organic layer, and the mixture was stirred for 30 minutes. The mixture was filtered through celite and concentrated. The crude product obtained was purified using a silica gel column (hexane/ethyl acetate) to thereby obtain 2.2 g of a compound S-9 (yield: 68%).

The NMR measurement data of the compound S-9 is as follows.

$^1$H NMR (400 MHz, $CDCl_3$, δ, ppm) 2.57 (m, 6H), 2.98 (d, 2H), 6.99 (Ar, 6H), 7.07 (Ar, 3H), 7.14 (Ar, 12H), 7.22 (Ar, 6H), 7.44 (Ar, 6H)

The above-obtained compound S-9 (1.1 g) was dissolved in 7.5 mL of tetrahydrofuran (THF), and 10 mg of dibutyltin dilaurate was added. 290 mg of 2-isocyanatoethyl acrylate (Karenz AOI manufactured by Showa Denko K.K.) was added to the prepared solution, and the mixture was allowed to react at room temperature. After a lapse of 24 hours, an additional 300 mg of 2-isocyanatoethyl acrylate was added, and the mixture was allowed to further react for 24 hours. Water was added to the reaction solution, and 50 mL of ethyl acetate was added to extract the organic layer. The obtained organic layer was extracted twice with 30 mL of water, and the aqueous layer generated was back-extracted twice with 50 mL of ethyl acetate. The resulting organic layer was dried over magnesium sulfate and concentrated at 30° C. or lower. The crude product obtained by concentrating the organic layer was purified using a silica gel column (hexane/ethyl acetate) to thereby obtain 600 mg of the compound M-6 (yield: 50%).

The NMR measurement data of the compound M-6 is as follows.

$^1$H NMR (400 MHz, $CDCl_3$, δ, ppm) 2.49 (m, 6H), 3.23 (m, 2H), 3.53 (s, 2H), 4.08 (t, 2H), 4.52 (dd, 1H), 5.82 (d, 1H), 6.08 (dd, 1H), 6.40 (d, 1H), 7.10 (Ar, 27H), 7.44 (Ar, 6H)

A holographic recording medium 1 was produced in the same manner as in Example 1 except that the compound M-6 was used as the polymerizable monomer, and evaluation of the holographic recording medium 1 was performed. The results are shown in Table 1 below.

Example 7

A compound M-7 was produced by the following synthesis method.

[Chem. 24]

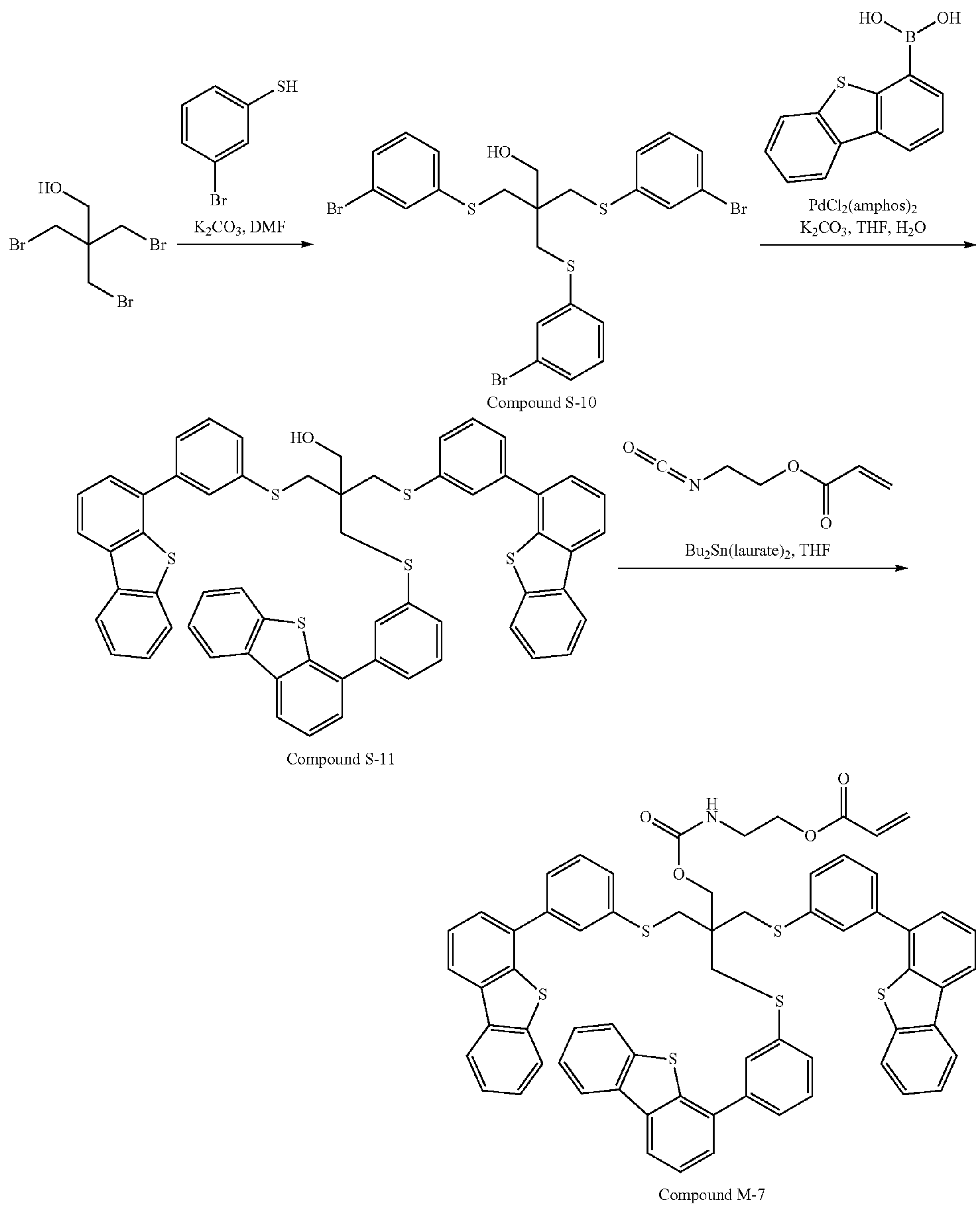

Compound S-10

Compound S-11

Compound M-7

4.80 g of 3-bromobenzenethiol, 2.50 g of pentaerythritol-tribromide, and 3.19 g of potassium carbonate were suspended in 13 mL of N,N-dimethylformamide (DMF). Then the reaction mixture was heated to 100° C. While the progress of the reaction was checked by LC analysis, the mixture was stirred for 4 hours. The resulting mixture was cooled to room temperature, extracted with ethyl acetate, and washed with water. The aqueous layer was back-extracted twice with ethyl acetate. The organic layer obtained was dried over mirabilite and then concentrated. The crude product obtained by concentrating the organic layer was purified using a silica gel column (hexane/ethyl acetate) to thereby obtain 5.0 g of a compound S-10 (yield: 100%).

The NMR measurement data of the compound S-10 is as follows.

$^1H$ NMR (400 MHz, $CDCl_3$, δ, ppm) 3.15 (s, 6H), 3.66 (d, 2H), 7.09 (Ar, 3H), 7.25 (Ar, 6H), 7.45 (Ar, 3H)

The above-obtained compound S-10 (2.3 g), 3.2 g of dibenzothiophene-4-boronic acid, and 2.9 g of potassium carbonate were suspended in 23 mL of THF and 3 mL of water, and nitrogen gas was bubbled through the mixture to degas the mixture. 70 mg of dichlorobis[di-t-butyl(p-dimethylaminophenyl)phosphino]palladium (II) was added to the reaction solution, and nitrogen gas was further bubbled through the mixture for 10 minutes. The reaction solution was heated in a nitrogen atmosphere and stirred at reflux for 6 hours. The resulting mixture was cooled to room temperature, extracted with ethyl acetate, and washed with water. The aqueous layer was extracted twice with ethyl acetate. 0.5 g of activated carbon was added to the organic layer obtained, and the mixture was stirred for 30 minutes. The mixture was filtered through celite and concentrated, and the crude product obtained was purified using a silica gel column (hexane/ethyl acetate) to thereby obtain 2.9 g of a compound S-11 (yield: 87%).

The NMR measurement data of the compound S-11 is as follows.

$^1$H NMR (400 MHz, $CDCl_3$, δ, ppm) 3.37 (s, 6H), 3.82 (d, 2H), 7.28 (Ar, 3H), 7.34 (Ar, 3H), 7.41 (Ar, 15H), 7.71 (Ar, 6H), 8.05 (Ar, 3H), 8.11 (Ar, 3H)

The above-obtained compound S-11 (2.9 g) was dissolved in 14.5 mL of tetrahydrofuran (THF), and 40 mg of dibutyltin dilaurate was added. 850 mg of 2-isocyanatoethyl acrylate (Karenz AOI manufactured by Showa Denko K.K.) was added to the prepared solution, and the mixture was allowed to react at room temperature. After a lapse of 24 hours, an additional 400 mg of 2-isocyanatoethyl acrylate was added, and the mixture was allowed to further react for 24 hours. Water was added to the reaction solution, and then 100 mL of ethyl acetate was added to extract the organic layer. The organic layer obtained was extracted twice with 50 mL of water, and the aqueous layer generated was back-extracted twice with 50 mL of ethyl acetate. The resulting organic layer was dried over magnesium sulfate and concentrated at 30° C. or lower. The crude product obtained by concentrating the organic layer was purified using a silica gel column (hexane/ethyl acetate) to thereby obtain 1.1 g of the compound M-7 (yield: 33%).

The NMR measurement data of the compound M-7 is as follows.

$^1$H NMR (400 MHz, $CDCl_3$, δ, ppm) 3.22 (m, 2H), 3.37 (s, 6H), 3.99 (t, 2H), 4.30 (s, 2H), 4.70 (dd, 1H), 5.62 (d, 1H), 5.82 (dd, 1H), 6.23 (d, 1H), 7.27 (Ar, 3H), 7.38 (Ar, 18H), 7.71 (Ar, 6H), 8.05 (Ar, 3H), 8.11 (Ar, 3H)

A holographic recording medium 1 was produced in the same manner as in Example 1 except that the compound M-7 was used as the polymerizable monomer, and evaluation of the holographic recording medium 1 was performed. The results are shown in Table 1 below.

Example 8

A compound M-8 was produced by the following synthesis method.

[Chem. 25]

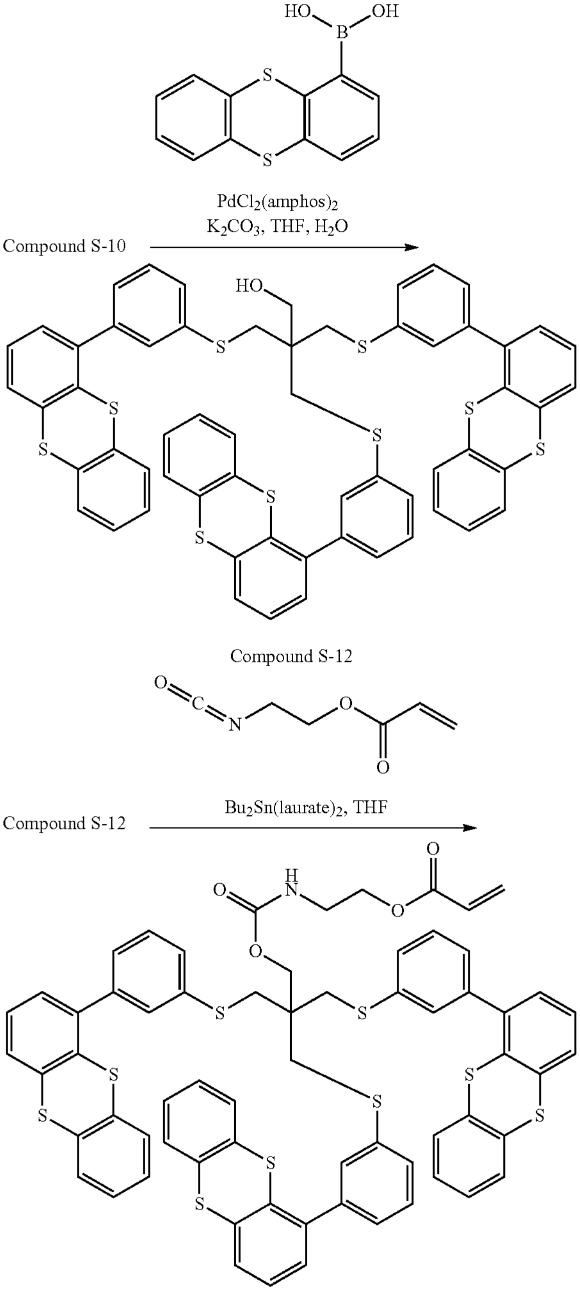

Compound S-10

Compound S-12

Compound S-12

Compound M-8

The compound S-10 (1.0 g) obtained in Example 7, 1.6 g of thianthrene-1-boronic acid, and 2.9 g of potassium phosphate were suspended in 14 mL of toluene, 7 mL of ethanol, and 7 mL of water, and nitrogen gas was bubbled through the mixture to degas the mixture. 30 mg of dichlorobis[di-t-butyl(p-dimethylaminophenyl)phosphino]palladium (II) was added to the reaction solution, and nitrogen gas was further bubbled through the mixture for 10 minutes. The reaction solution was heated in a nitrogen atmosphere and stirred at reflux for 6 hours. The resulting mixture was cooled to room temperature, extracted with ethyl acetate, and washed with water. The aqueous layer was extracted twice with ethyl acetate. 0.5 g of activated carbon was added to the organic layer obtained, and the mixture was stirred for 30 minutes. The mixture was filtered through celite and concentrated. The crude product obtained was purified using a silica gel column (hexane/ethyl acetate) to thereby obtain 1.6 g of a compound S-12 (yield: 98%).

The NMR measurement data of the compound S-12 is as follows.

$^1$H NMR (400 MHz, $CDCl_3$, δ, ppm) 3.27 (s, 6H), 3.73 (d, 2H), 7.01 (Ar, 9H), 7.09 (Ar, 6H), 7.19 (Ar, 6H), 7.31 (Ar, 6H), 7.38 (Ar, 6H)

The above-obtained compound S-12 (1.6 g) was dissolved in 8.0 mL of tetrahydrofuran (THF), and 20 mg of dibutyltin dilaurate was added. 650 mg of 2-isocyanatoethyl acrylate (Karenz AOI manufactured by Showa Denko K.K.) was added to the prepared solution, and the mixture was allowed to react at room temperature. After a lapse of 24 hours, another 650 mg of 2-isocyanatoethyl acrylate was added, and the mixture was allowed to further react for 24 hours. Water was added to the reaction solution, and 60 mL of ethyl acetate was added to extract the organic layer. The obtained organic layer was extracted twice with 30 mL of water, and the aqueous layer generated was back-extracted twice with 50 mL of ethyl acetate. The resulting organic layer was dried over magnesium sulfate and concentrated at 30° C. or lower. The crude product obtained by concentrating the organic layer was purified using a silica gel column (hexane/ethyl acetate) to thereby obtain 1.0 g of the compound M-8 (yield: 54%).

The NMR measurement data of the compound M-8 is as follows.

$^1$H NMR (400 MHz, $CDCl_3$, δ, ppm) 3.23 (m, 2H), 3.35 (s, 6H), 4.00 (t, 2H), 4.29 (s, 2H), 4.89 (dd, 1H), 5.68 (d, 1H), 5.86 (dd, 1H), 6.26 (d, 1H), 7.07 (Ar, 9H), 7.19 (Ar, 12H), 7.34 (Ar, 6H), 7.45 (Ar, 6H)

A holographic recording medium 1 was produced in the same manner as in Example 1 except that the compound M-8 was used as the polymerizable monomer, and evaluation of the holographic recording medium 1 was performed. The results are shown in Table 1 below.

Comparative Example 1

A compound M-9 was produced by the following synthesis method.

[Chem. 26]

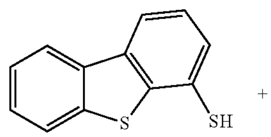

+

-continued

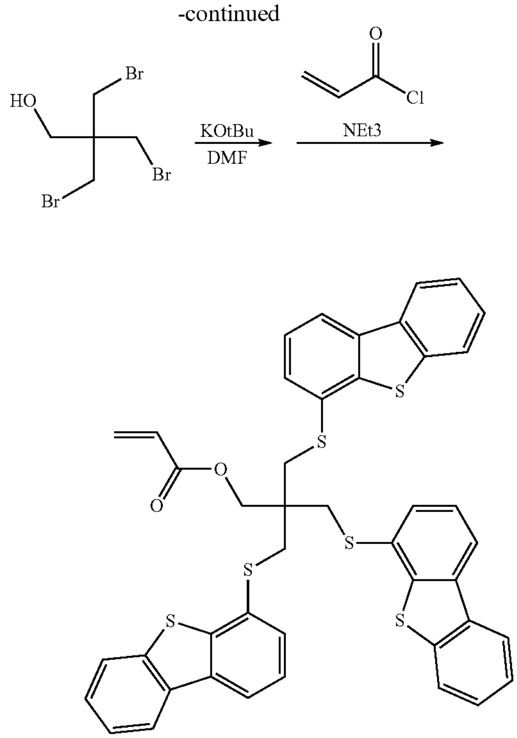

Compound M-9

5 g of the compound S-2 (DBTSH) obtained in Synthesis Example 1 and 2.7 g of potassium tert-butoxide were dissolved in 50 mL of N,N-dimethylformamide (DMF). 2.25 g of pentaerythritoltribromide was added to the prepared solution, and the mixture was heated to 80° C. While the progress of the reaction was checked by LC analysis, the mixture was stirred for 5 hours. The reaction solution was cooled to 0° C., and 1.3 mL of triethylamine and 0.68 mL of acryloyl chloride were added. The mixture was heated to 20° C. and stirred for 3 hours. 50 mL of water was added to the reaction solution, and 150 mL of ethyl acetate was added to extract the organic layer. The organic layer obtained was washed with 1N hydrochloric acid and a 1N aqueous sodium hydroxide solution and concentrated. The crude product obtained by concentrating the organic layer was purified using a silica gel column (hexane/ethyl acetate) to thereby obtain 2.3 g of the compound M-9 (yield: 43%).

The NMR measurement data of the compound M-9 is as follows.

$^1$H NMR (400 MHz, $CDCl_3$, δ, ppm) 3.41 (s, 6H), 4.23 (s, 2H), 5.46 (d, 1H), 5.67 (dd, 1H), 6.01 (d, 1H), 7.17 (Ar, 3H), 7.38 (Ar, 9H), 7.76 (Ar, 3H), 7.83 (Ar, 3H), 8.05 (Ar, 3H)

Holographic recording mediums 1 and 2 were produced in the same manner as in Example 1 except that the compound M-9 was used as the polymerizable monomer, and evaluation of the holographic recording mediums 1 and 2 was performed. The results are shown in Table 1 below.

TABLE 1

| | Polymerizable monomer | Evaluation sample | Numbers of times of multiple recording | Total Δn | Transmittance before recording % | Transmittance after recording % |
|---|---|---|---|---|---|---|
| Example 1 | M-1 | Holographic recording medium 1 | 91 | 0.0175 | 69 | 86 |
| | | Holographic recording medium 2 | 121 | 0.0269 | 48 | 82 |
| Example 2 | M-2 | Holographic recording medium 1 | 91 | 0.0180 | 69 | 86 |
| Example 3 | M-3/M-9 (molar ratio: 10/90) | Holographic recording medium 2 | 121 | 0.0260 | 48 | 82 |
| Example 4 | M-4 | Holographic recording medium 1 | 91 | 0.0140 | 69 | 86 |
| Example 5 | M-5 | Holographic recording medium 1 | 91 | 0.0187 | 70 | 84 |
| Example 6 | M-6 | Holographic recording medium 1 | 91 | 0.0213 | 68 | 85 |
| Example 7 | M-7 | Holographic recording medium 1 | 91 | 0.0209 | 64 | 81 |
| Example 8 | M-8 | Holographic recording medium 1 | 91 | 0.0211 | 67 | 84 |
| Comparative Example 1 | M-9 | Holographic recording medium 1 | 91 | 0.0123 | 69 | 86 |
| | | Holographic recording medium 2 | 121 | 0.0191 | 48 | 82 |

In the holographic recording mediums 1, the molar concentrations of the polymerizable monomer, the photopolymerization initiator, and the additive in the polymerizable compositions were the same, and only the types of polymerizable monomers were changed.

In Comparative Example 1, the total Δn was 0.0123. In Examples 1, 2 and 4 to 8, the total Δn's were 0.0175, 0.0180, 0.0140, 0.0187, 0.0213, 0.0209, and 0.0211, respectively, and were larger by a factor of about 1.1 to about 1.7 than that in Comparative Example 1.

As described above, in the optical element applications such as light guide plates for AR glasses, the higher the total Δn, the brighter the projected image, and the wider the viewing angle. For example, an increase in Δn by a factor of 1.7 (0.0123→0.0213) corresponds to an increase in diffraction efficiency by a factor of 2.1 and means that the brightness of the projected image is increased by a factor of 2.1. This means that, at the same projected image brightness, the power consumption is reduced by a factor of 0.5 or the usable time of the battery is extended by a factor of 2.1.

In the memory applications, an increase in the total Δn can increase the recording capacity.

Therefore, when the holographic recording mediums are used for these applications, the compounds of the invention used in the Examples are superior to the compound in the Comparative Example.

In the holographic recording mediums 2, the mixing ratio of the polyols in the polymerizable composition was different from that in the holographic recording mediums 1, and the molar concentrations of the polymerizable monomer, the photopolymerization initiator, and the additive were 2 times larger than those in the holographic recording mediums 1.

In Comparative Example 1 in which only the compound M-9 was used as the polymerizable monomer, the total Δn was 0.0191.

In Example 1 in which the compound M-1 was used, the total Δn was 0.0269. In Example 3 in which a mixture of the compound M-3 and the compound M-9 at a molar ratio of 10:90 was used as the polymerizable monomer, the total Δn was 0.0260, which is larger by a factor of about 1.4 than that in Comparative Example 1.

Therefore, although the above compounds of the invention differ in the mixing ratio of the polyols and the concentrations of the polymerizable monomer, the photopolymerization initiator, and the radical scavenger, the compounds of the invention are more suitable for holographic recording mediums than the compound in the Comparative Example.

[Refractive Index]

The refractive index of each of the compounds used as the monomers in the Examples and Comparative Example was measured by the following method.

A test solution having a prescribed sample concentration was prepared by dissolving a sample in a solution mixture of 3-phenoxybenzyl acrylate and trimethylolpropane trimethacrylate at a mass ratio of 4:1. Specifically, two test solutions with sample concentrations of 10% by mass and 20% by mass were prepared. The refractive index of each test solution was measured using a Kalnew precision refractometer (product name: KPR-2000 manufactured by Shimadzu Corporation). The temperature of the test solution was 23° C., and the measurement wavelength was the d line (587.6 nm) of a helium lamp. A calibration curve representing the correlation between the sample concentration and the refractive index was produced based on the measurement results. Using the obtained calibration curve, the refractive index at a sample concentration of 100% by mass was determined and used as the refractive index of the sample.

TABLE 2

| | Compound | Refractive index |
|---|---|---|
| Example 1 | M-1 | 1.679 |
| Example 2 | M-2 | 1.685 |
| Example 3 | M-3 | 1.666 |
| Example 5 | M-5 | 1.692 |
| Example 6 | M-6 | 1.672 |
| Example 7 | M-7 | 1.691 |
| Example 8 | M-8 | 1.679 |
| Comparative Example 1 | M-9 | 1.720 |

[Estimated Values of Refractive Indexes]

The refractive index of each of the compounds used as the polymerizable monomers in the Examples and Comparative Example after curing was estimated. Software, Polymer-Desgin Tools Version 1.1 manufactured by DTW Associates, Inc., was used to estimate the refractive index at 25° C. and 589 nm using a Bicerano method. The values determined are shown in Table 3 below.

The values obtained were equivalent to the above measurement values.

TABLE 3

| | Compound | Estimated refractive index value after curing |
|---|---|---|
| Example 1 | M-1 | 1.699 |
| Example 2 | M-2 | 1.676 |
| Example 4 | M-4 | 1.702 |
| Comparative Example 1 | M-9 | 1.719 |

The refractive index of each of the compounds in the Examples is slightly lower than that of the compound in the Comparative Example. However, the total Δn of each of the holographic recording mediums in the Examples is higher, as described above. As can be seen from these results, the polymerizability of the compounds of the invention is superior to that of the compound in the Comparative Example.

In the compound M-1 in the invention, the tri(thiodibenzothiophene) group is bonded through a urethane bond. In the compounds M-4 in the invention, the tri(thiodibenzothiophene) group is bonded through an ester bond. Therefore, the spatial distance between the acrylate group and the tri(thiodibenzothiophene) group is large. In this case, the acrylate group is not susceptible to steric hindrance, and this may be the reason that good polymerizability is obtained. The reason that the polymerizability of the compounds M-2, M-3 and M-5 to M-8 is good may be the same as above.

In the compound M-9 in the Comparative Example in which the tri(thiodibenzothiophene) group is bonded through an ethyl group, the acrylate group is susceptible to steric hindrance, and this may be the reason that the polymerizability is low.

Although the present invention has been described in detail by way of the specific modes, it is apparent for those skilled in the art that various changes can be made without departing from the spirit and scope of the present invention.

The present application is based on Japanese Patent Application No. 2019-208980 filed on Nov. 19, 2019, the entire contents of which are incorporated herein by reference.

REFERENCE SIGNS LIST

S holographic recording medium
M1, M2, M3 mirror
L1 semiconductor laser light source for recording light
L2 laser light source for reproduction light
PD1, PD2, PD3 photodetector
PBS polarizing beam splitter
1 LED unit

The invention claimed is:

1. A compound represented by formula (1):

(1)

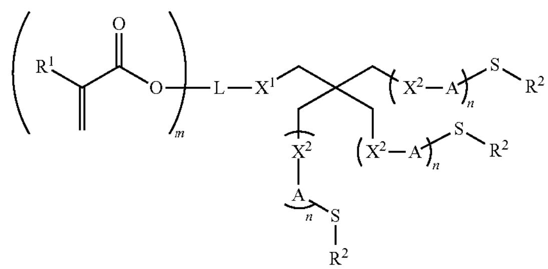

wherein $R^1$ represents a hydrogen atom or a methyl group; $R^2$ represents a phenyl group having a dibenzothiophenyl group, a thianthrenyl group, or a benzothiazolyl group as a substituent; $X^1$ represents a (thio) carbonate bond, a (thio) urethane bond, or a (thio) urea bond; L represents an (m+1)-valent linking group optionally having a substituent; m represents an integer of 1 to 3; and n represents 0.

2. The compound according to claim 1, wherein L is a hydrocarbon group having 1 to 8 carbon atoms and optionally having a substituent.

3. The compound according to claim 2, wherein L is an aliphatic hydrocarbon group having 1 to 8 carbon atoms and optionally having a substituent.

4. The compound according to claim 3, wherein L is a chain aliphatic hydrocarbon group having 1 to 8 carbon atoms and optionally having a substituent.

5. The compound according to claim 1, wherein $X^1$ represents a urethane bond.

6. The compound according to claim 1, wherein m represents 2 or 3.

7. The compound according to claim 1, wherein m represents 1.

8. A polymerizable composition comprising: the compound according to claim 1; and a polymerization initiator.

9. A holographic recording medium comprising the polymerizable composition according to claim 8.

10. A polymer obtained by polymerizing the polymerizable composition according to claim 8.

11. An optical material comprising the polymer according to claim 10.

12. An optical component comprising the polymer according to claim 10.

13. A large-capacity memory comprising the holographic recording medium according to claim 9.

14. An optical element obtained by recording a hologram in the holographic recording medium according to claim 9.

15. An augmented reality glass comprising the optical element according to claim 14.

* * * * *